(12) United States Patent
Lo et al.

(10) Patent No.: US 7,901,884 B2
(45) Date of Patent: Mar. 8, 2011

(54) MARKERS FOR PRENATAL DIAGNOSIS AND MONITORING

(75) Inventors: Yuk Ming Dennis Lo, Kowloon (HK); Rossa Wai Kwun Chiu, New Territories (HK); Stephen Siu Chung Chim, Quarry Bay (HK); Chunming Ding, New Territories (HK); Shengnan Jin, New Territories (HK); Tracy Yuen Han Lee, Tsuen Wan (HK); Fiona Miu Fun Lun, New Territories (HK)

(73) Assignee: The Chinese University of Hong Kong, Shatin N.T. (HK)

( * ) Notice: Subject to any disclaimer, the term of this patent is extended or adjusted under 35 U.S.C. 154(b) by 805 days.

(21) Appl. No.: 11/784,499

(22) Filed: Apr. 6, 2007

(65) Prior Publication Data

US 2007/0275402 A1 Nov. 29, 2007

Related U.S. Application Data

(60) Provisional application No. 60/797,456, filed on May 3, 2006.

(51) Int. Cl.
*C07H 21/04* (2006.01)
*C12Q 1/68* (2006.01)

(52) U.S. Cl. .......... 435/6; 435/91.1; 435/91.2; 536/23.1; 536/24.3

(58) Field of Classification Search .................. None
See application file for complete search history.

(56) References Cited

U.S. PATENT DOCUMENTS

2003/0044388 A1 3/2003 Dennis et al.
2003/0211522 A1 11/2003 Landes et al.

FOREIGN PATENT DOCUMENTS

WO WO 2004/065629 A1 8/2004
WO WO 2005/118852 A2 12/2005

OTHER PUBLICATIONS

Tong et al. Clinical Chemistry, vol. 56, No. 1, 2010.*
Illanes et al. (Prenatal Diagnosis, vol. 26, No. 13, pp. 1213-1218, 2006).*
Pao et al. (Human Molecular Genetics, vol. 10, No. 9, pp. 903-910).*
Cameron et al. (Blood, vol. 94, No. 7, pp. 2445-2451, Oct. 1999).*
Leung, Tse N., et al., "Increased Maternal Plasma Fetal DNA Concentrations in Women Who Eventually Develop Preclampsia" *Clinical Chemistry*, 2001, vol. 47, No. 1, pp. 137-139.
Lo, Dennis Y.M. "Fetal DNA in Maternal Plasma: Biology and Diagnostic Applications," *Clinical Chemistry*, 2000, vol. 46, No. 12, pp. 1903-1906.
Lo, Dennis Y.M., et al., "Presence of fetal DNA in maternal plasma and serum," *The Lancet*, 1997, vol. 350, pp. 485-487.
Lo, Dennis Y.M., et al., "Quantitative Abnormalities of Fetal DNA in Maternal Serum in Preeclampsia," *Clinical Chemistry*, 1999, vol. 45, No. 2, pp. 184-188.
Lui, Yanni Y.N., et al., "Predominant Hematopoietic Origin of Cell-free DNA in Plasma and Serum after Sex-mismatched Bone Marrow Transplantation," *Clinical Chemistry*, 2002, vol. 48, No. 3, pp. 421-427.
Ng, Enders K.O., et al., "mRNA of placental origin is readily detectable in maternal plasma" *PNAS*, 2003, vol. 100, No. 8, pp. 4748-4753.
Poon, Leo L.M., et al., "Differential DNA Methylation between Fetus and Mother as a Strategy for Detecting Fetal DNA in Maternal Plasma," *Clinical Chemistry*, 2002, vol. 48, No. 1, pp. 35-41.
Sekizawa, Akihiko., et al., "Cell-free Fetal DNA is Increased in Plasma of Women with Hyperemesis Gravidarium," *Clinical Chemistry*, 2001, vol. 47, No. 12, pp. 2164-2165.

* cited by examiner

*Primary Examiner* — Jeanine A Goldberg
(74) *Attorney, Agent, or Firm* — Kilpatrick Townsend & Stockton LLP

(57) ABSTRACT

This application provides the use of novel fetal markers for prenatal diagnosis and monitoring of certain pregnancy-related conditions. More specifically, the invention resides in the discovery that certain CpG islands located on fetal chromosome 21 demonstrate a methylation profile that is distinct from that of the corresponding CpG islands located on maternal chromosome 21. This application also provides kits for diagnosing or monitoring of the relevant conditions.

27 Claims, 35 Drawing Sheets

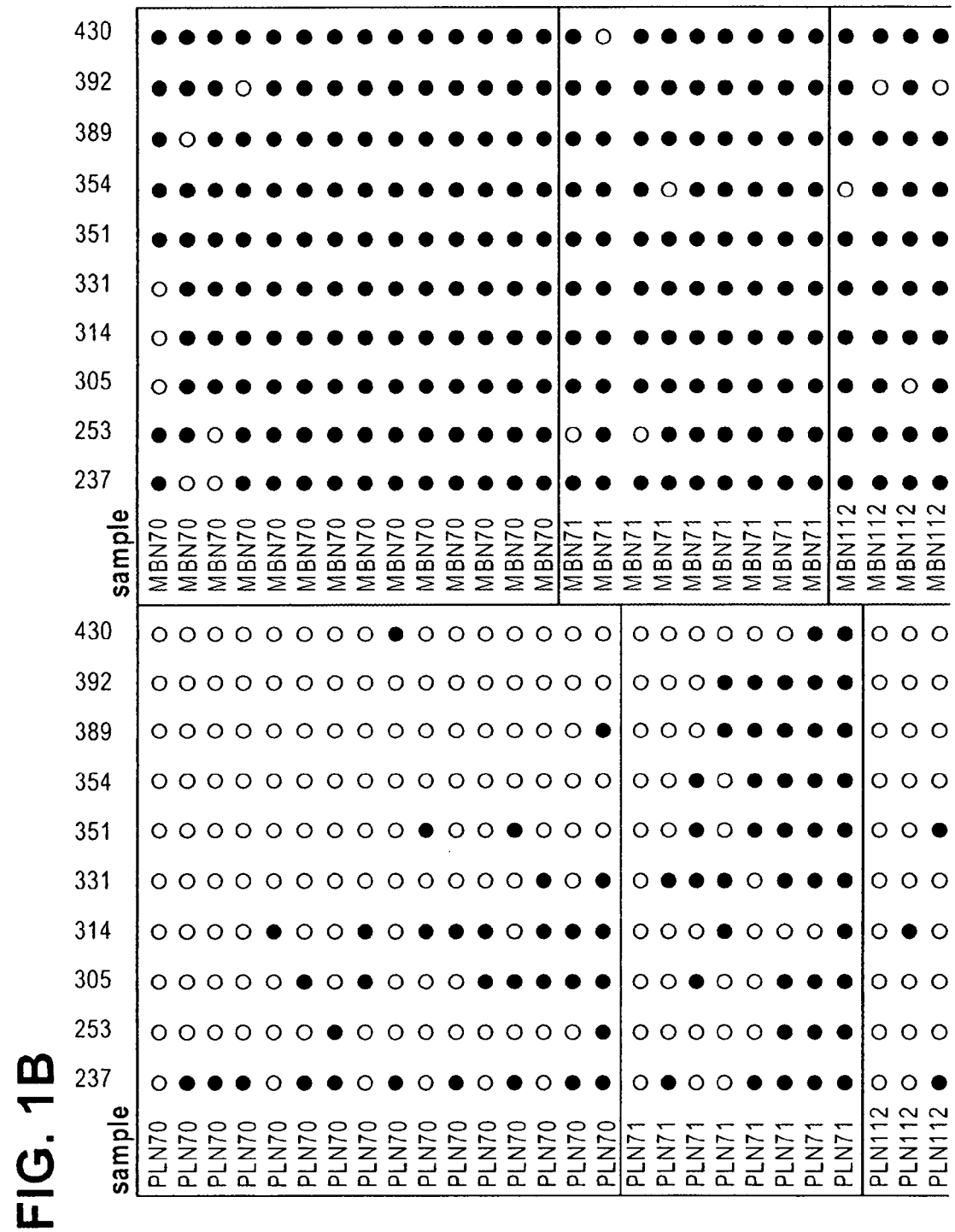

FIG. 1B (cont.)

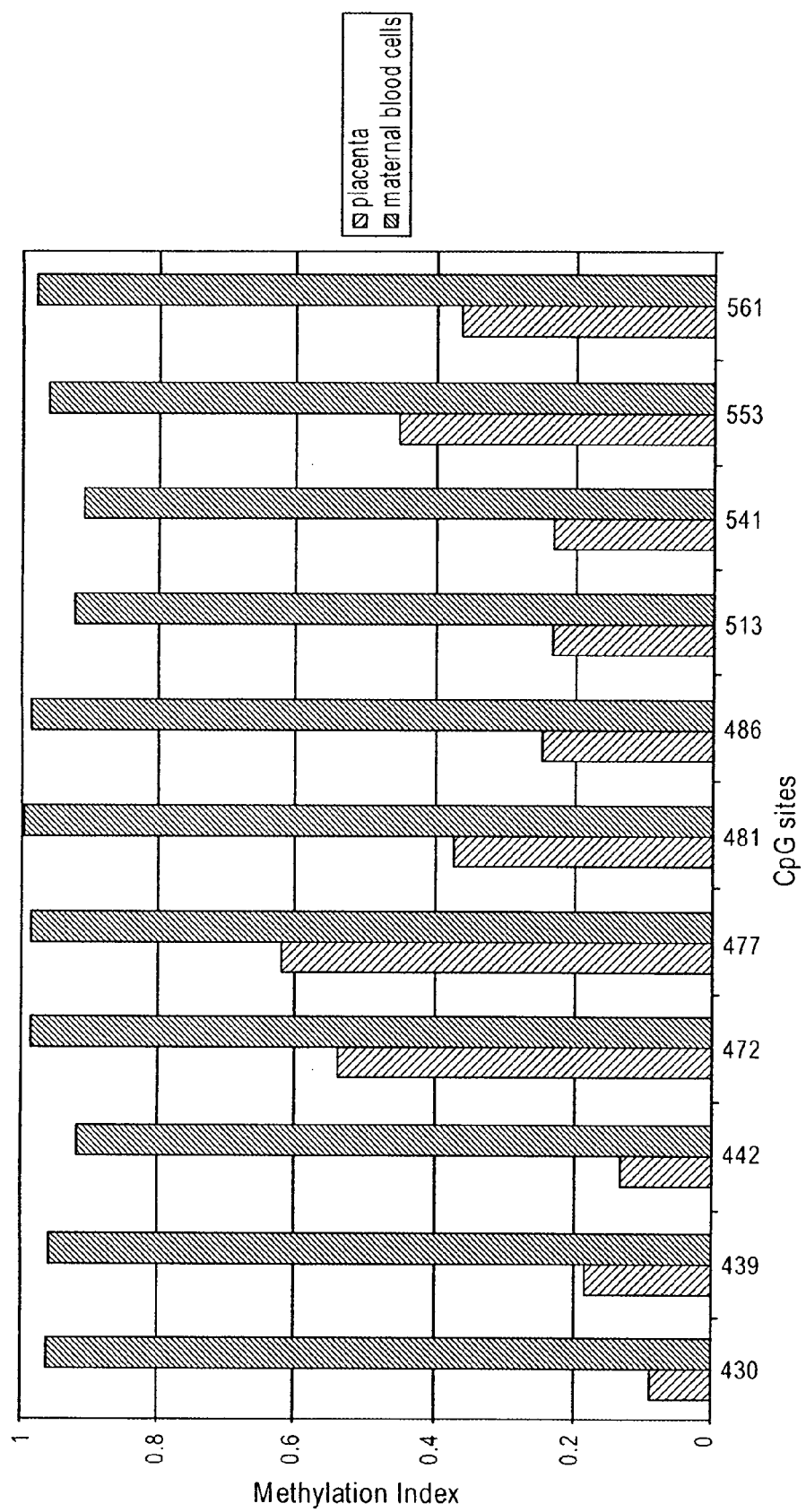

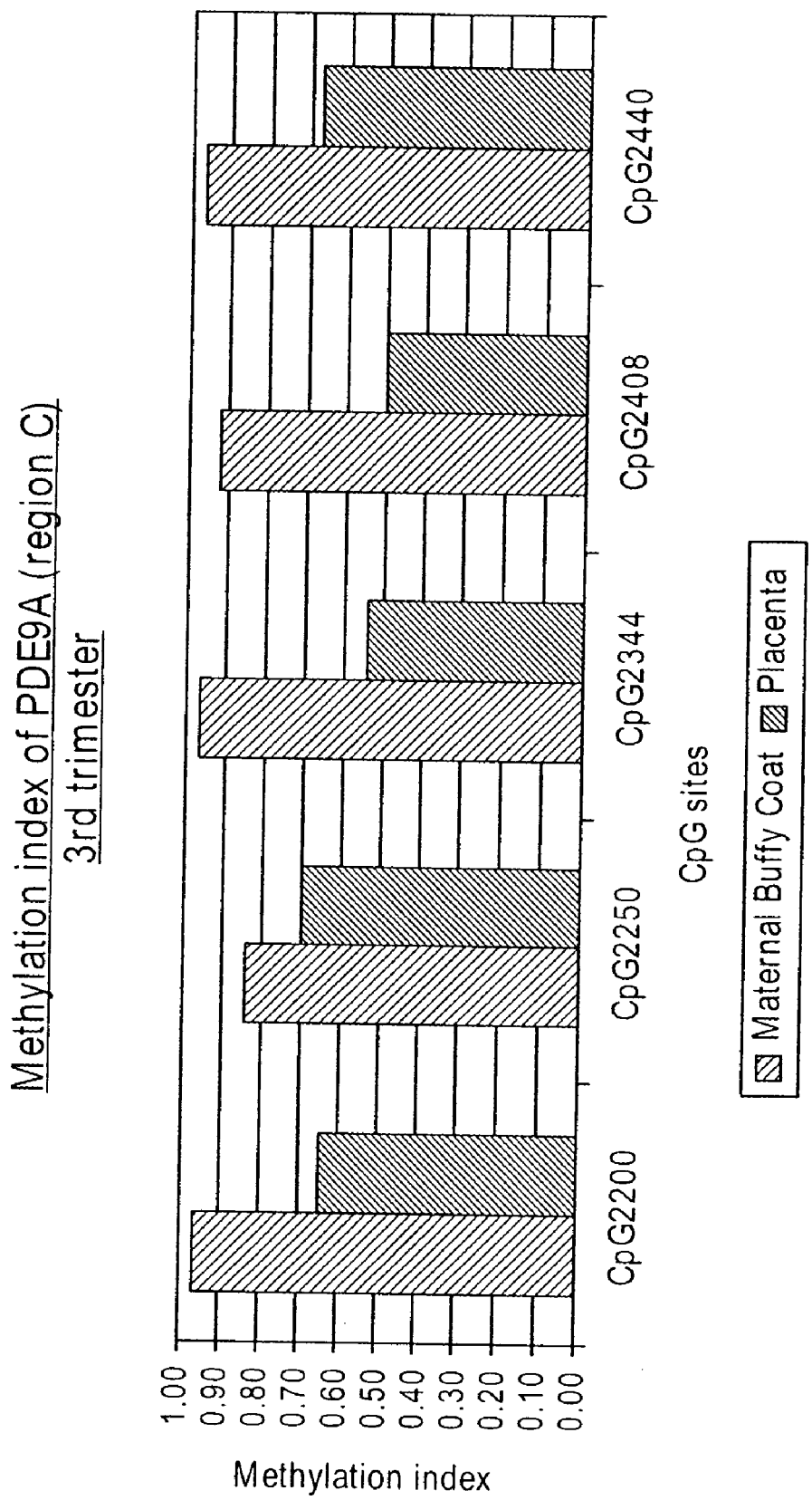

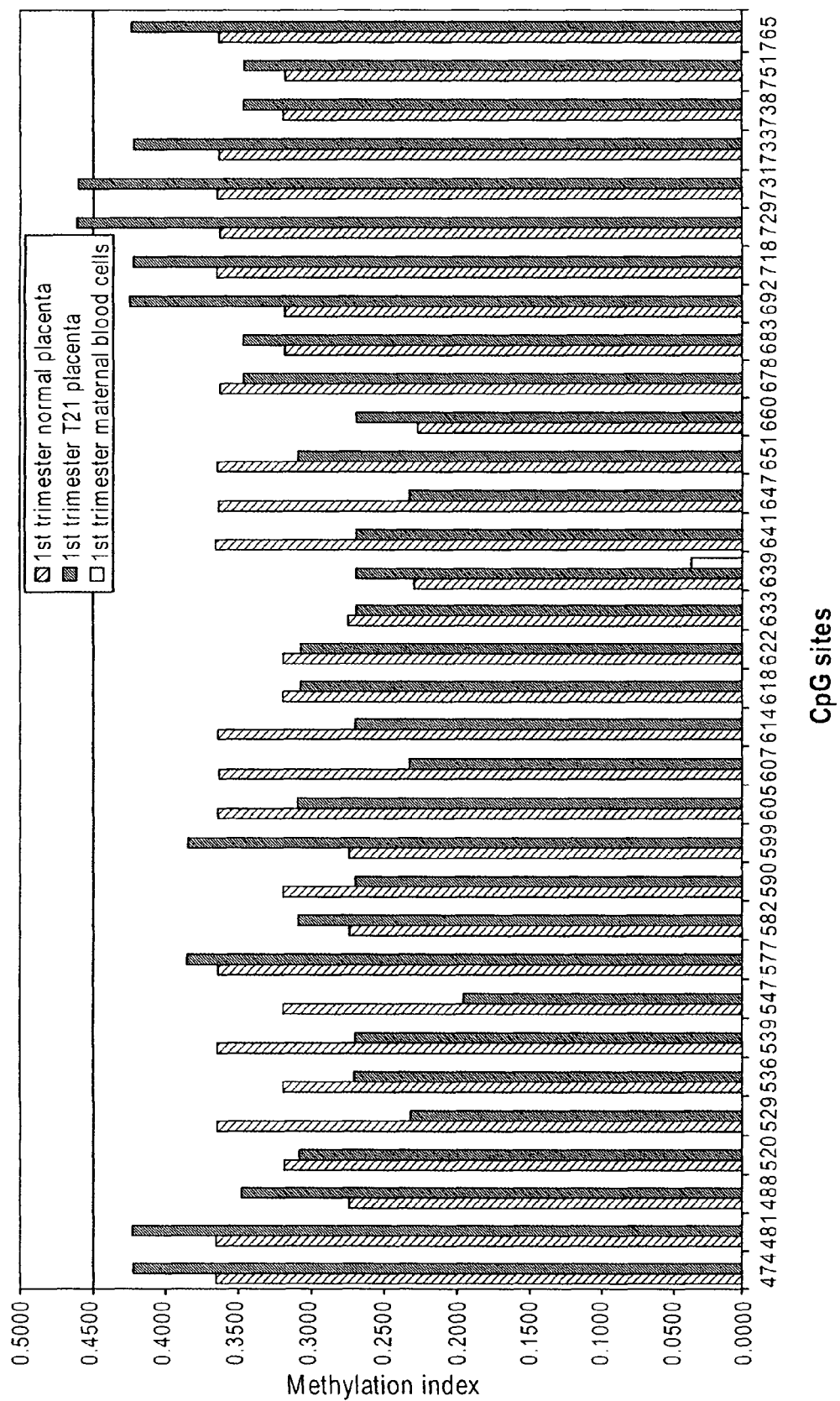

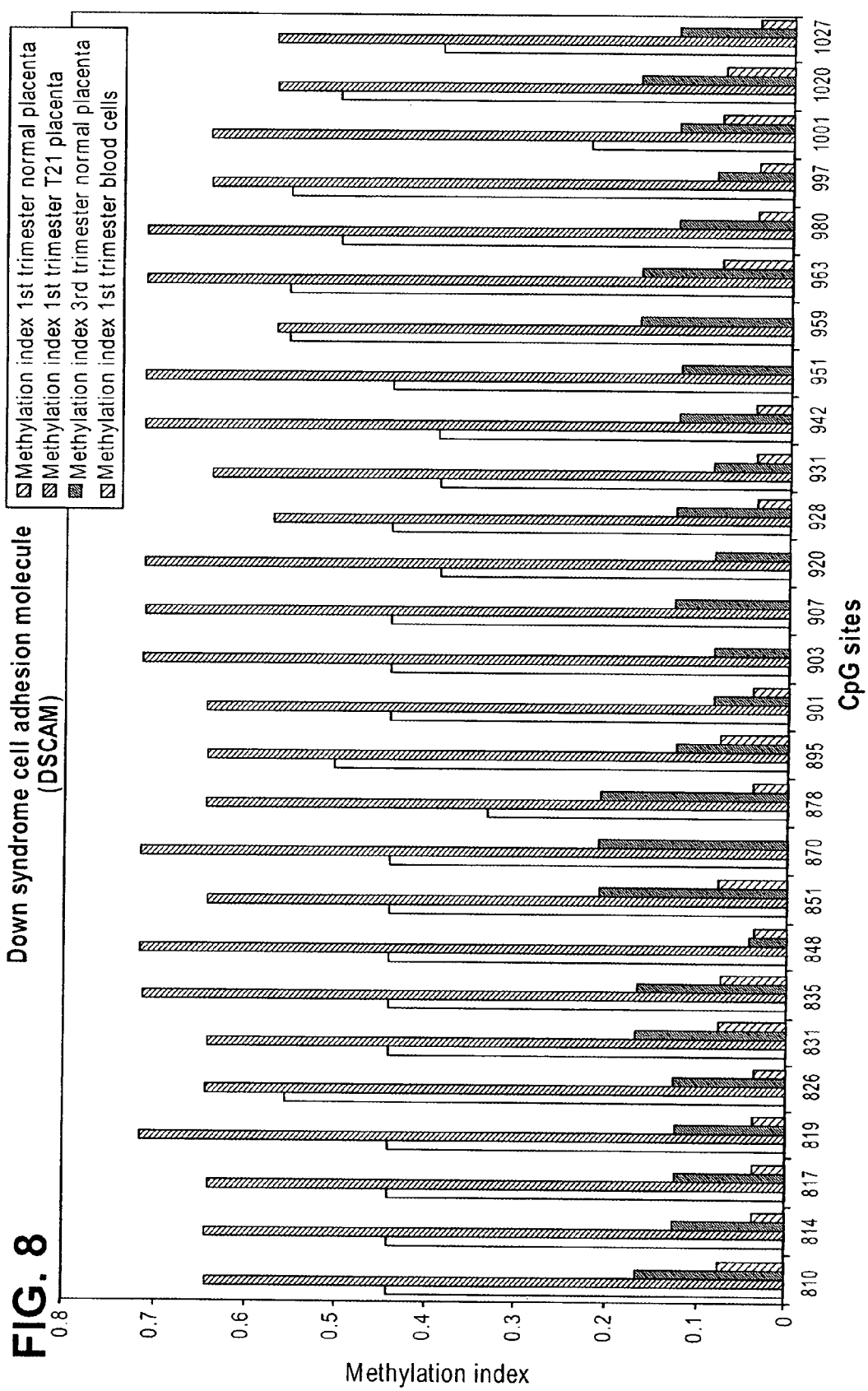

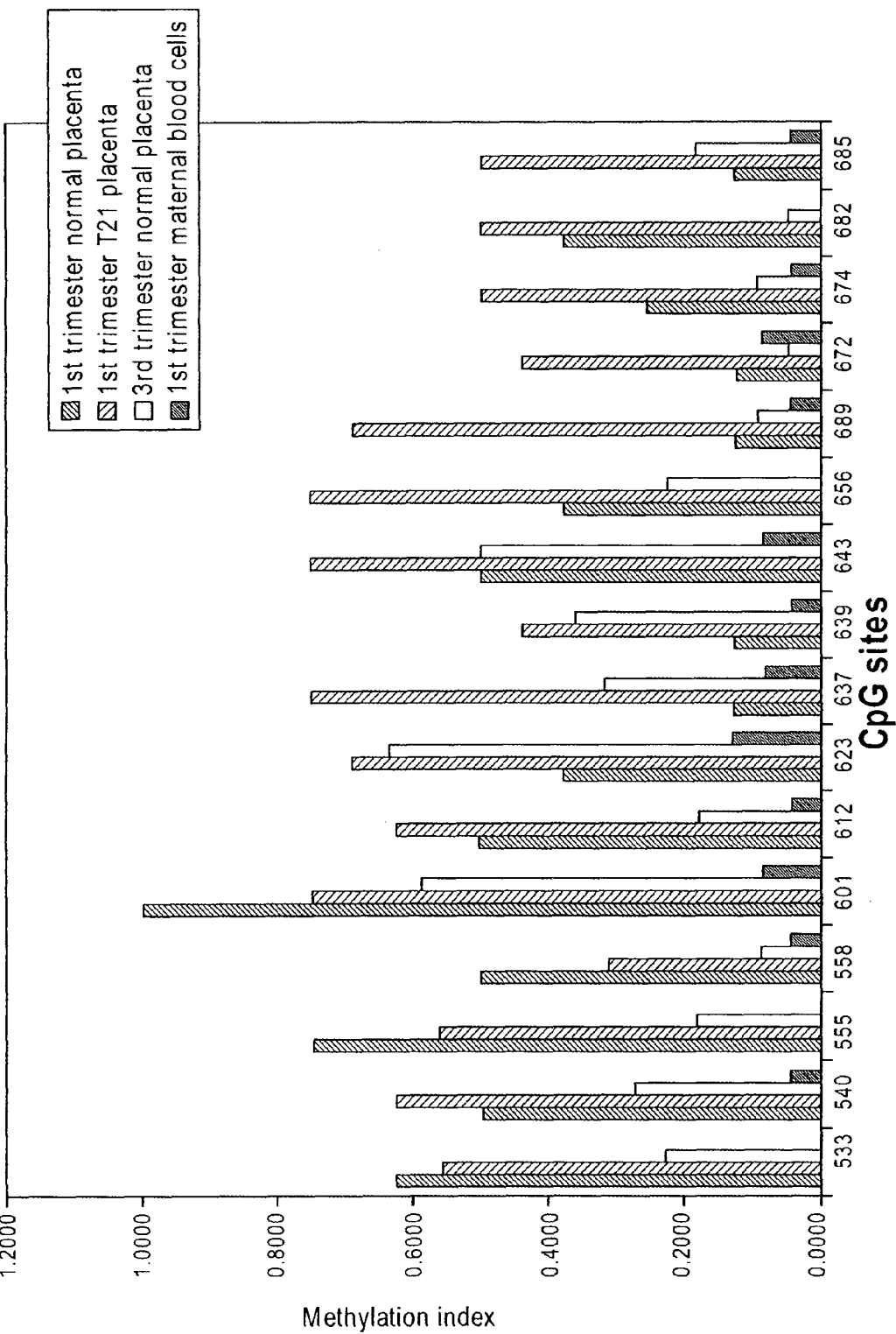

FIG. 10

| Specimen | | MBN114 | | | PLN114 | | | | MBN118 | | | | | | PLN118 | | | | |
|---|---|---|---|---|---|---|---|---|---|---|---|---|---|---|---|---|---|---|---|
| Clones | | 1 | 2 | 4 | 1 | 4 | 7 | | 2 | 3 | 4 | 6 | 7 | | 1 | 2 | 3 | 5 | 7 |
| CpG1375 | | O | O | O | O | O | O | | O | O | O | O | O | | O | O | O | O | O |
| CpG1364 | | O | O | O | O | O | O | | O | O | O | O | O | | O | O | O | O | O |
| CpG1358 | | O | O | O | O | O | O | | O | O | O | O | O | | O | O | O | O | O |
| CpG1342 | | O | O | O | O | O | O | | O | O | O | O | O | | O | O | O | O | O |
| CpG1331 | | O | O | O | O | O | O | | O | O | O | O | O | | O | O | O | O | O |
| CpG1329 | | O | O | O | O | O | O | | O | O | O | O | O | | O | O | O | O | O |
| CpG1313 | | O | O | O | O | O | O | | O | O | O | O | O | | O | O | O | O | O |
| CpG1307 | | O | O | O | O | O | O | | O | O | O | O | O | | O | O | O | O | O |
| CpG1297 | | O | O | O | O | O | O | | O | O | O | O | O | | O | ● | O | O | O |
| CpG1293 | | O | O | O | O | O | O | | O | O | O | O | O | | O | ● | O | O | O |
| CpG1289 | | O | O | O | O | O | O | | O | O | O | O | O | | O | ● | O | O | O |
| CpG1287 | | O | O | O | O | O | O | | O | O | O | O | O | | O | ● | O | O | O |
| CpG1285 | | O | O | O | O | O | O | | O | O | O | O | O | | O | ● | O | O | O |
| CpG1260 | | O | O | O | O | O | O | | O | O | O | O | O | | O | O | O | O | O |
| CpG1246 | | O | O | O | O | O | O | | O | O | O | O | O | | O | O | O | O | O |
| CpG1186 | | O | O | O | O | O | O | | O | O | O | O | O | | O | O | O | O | O |
| CpG1184 | | O | O | O | O | O | O | | O | O | O | O | O | | O | O | O | O | O |
| CpG1179 | | O | O | O | O | O | O | | O | O | O | O | O | | O | O | O | O | O |

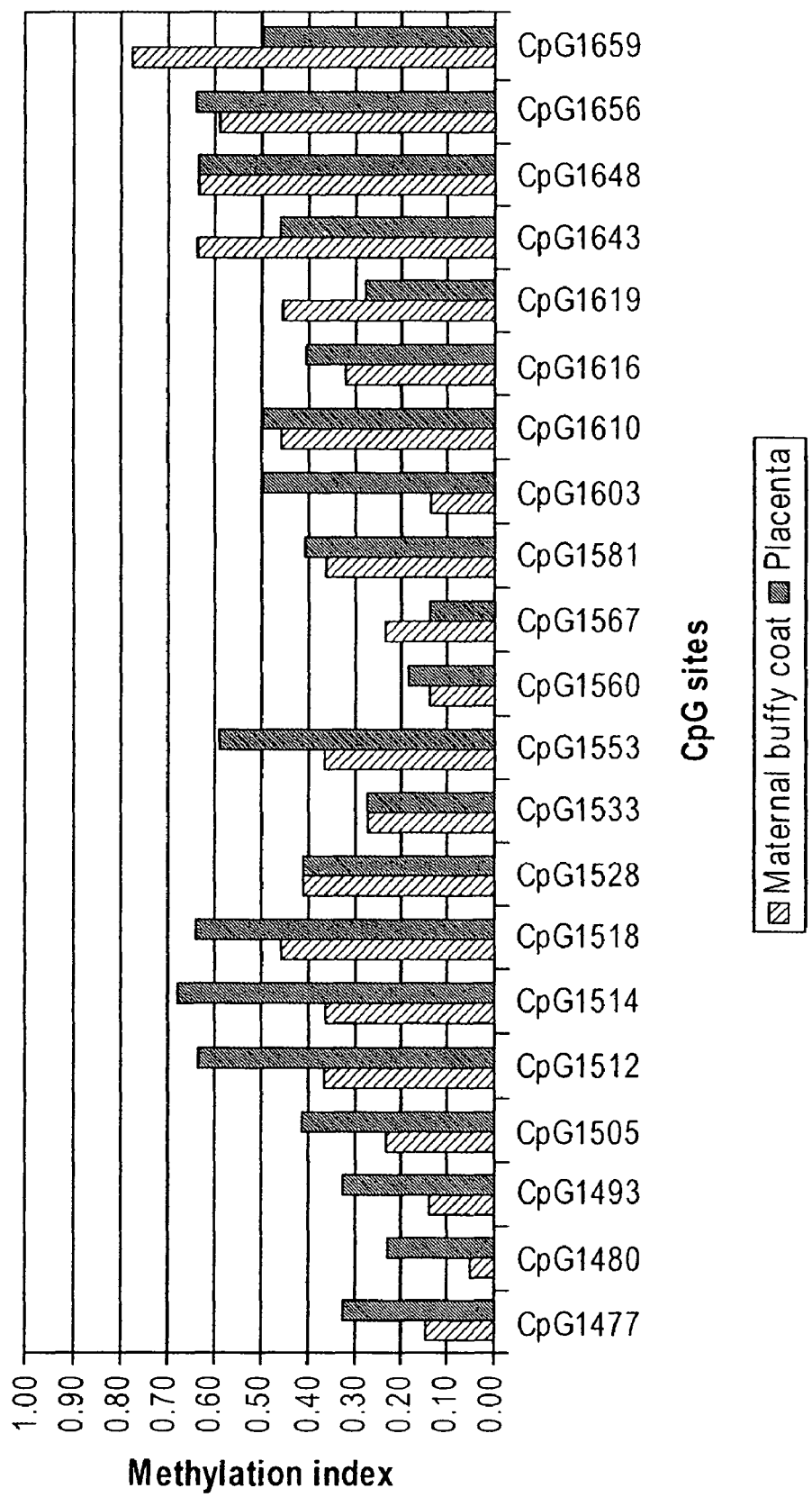

FIG. 12

```
421 CTTCACCTGCGGGGACCCCGGGCGAGCCCCTCAGGTGCCACAGGCAGGGACACGCCTCGCT
    :||::|::||+:::++|||:::++|||:::|:||||::|:|||||+|||+:|++:|++:|
421 TTTTATTTGCGGGGATTTCGGCGGAGTTTTTTAGGTGTTATAGGTAGGGATACGTTTCGTT
              430     439 442                        472   477
                                     TGTTATAGGTAGGGATATGTTTTGTT>    Forward primer 481 CGATGCGTCACACCATGTGGCCACCAGAGCTGCGGGAAAATGCTGGGACCCCTGCATTTC
    ++|||::|::|:||:|:::||||:::|:||+|+|||::||||:::|:|||||::|||||:
481 CGATGCGTTATATTATGTGGTTATTAGAGTTGCGGGAAAATGTTGGGGATTTTGTATTTT
       481    486                              513
    >TGACGT                                                         Forward primer 541 CGTTTCAGGTGGCGAACAAGCGCCCCTCACAGAACTGCAGGTAGAGACGGGCCCGGGGCA
    ++|::||::||||+||+::||:|||::||||||||::|::||||||+||||||::++||:|
541 CGTTTTAGGTGGCGAATAAGCGTTTTTTATAGAATTGTAGGTAGAATTGTAGGTAGAGA
      541    553    561                              588     594
              TGgATAAGTGTTTTTTATAGAATTGTAGGTAGAGA                  Reverse primer
    GTTTTAGGTGGTGGATAAGT                                            Extension primer
```

FIG. 17

MARKERS FOR PRENATAL DIAGNOSIS AND MONITORING

RELATED APPLICATIONS

This application claims priority to U.S. Provisional Patent Application No. 60/797,456, filed May 3, 2006, the contents of which are hereby incorporated by reference in the entirety.

BACKGROUND OF THE INVENTION

Early detection of pregnancy-related conditions, including potential complications during pregnancy or delivery and genetic defects of the fetus is of crucial importance, as it allows early medical intervention necessary for the safety of both the mother and the fetus. Prenatal diagnosis has been routinely conducted using cells isolated from the fetus through procedures such as chorionic villus sampling (CVS) or amniocentesis. These conventional methods are, however, invasive and present an appreciable risk to both the mother and the fetus despite most careful handling (Tabor et al., *Lancet* 1:1287-1293, 1986).

Alternatives to these invasive approaches have been developed for prenatal screening, e.g., to detecting fetal abnormalities, following the discoveries that several types of fetal cells can be found in maternal circulation (Johansen et al., *Prenat. Diagn.* 15:921-931, 1995) and more importantly, circulating cell-free fetal DNA can be detected in maternal plasma and serum (Lo et al., *Lancet* 350:485-487, 1997). The amount of fetal DNA in maternal blood has been shown to be sufficient for genetic analysis without complex treatment of the plasma or serum, in contrast to alternative methods requiring steps for isolating and enriching fetal cells. Fetal rhesus D (RhD) genotyping (Lo et al., *N. Engl. J. Med.* 339:1734-1738, 1998), fetal sex determination (Costa et al., *N. Engl. J. Med.* 346:1502, 2002), and diagnosis of several fetal disorders (Amicucci et al., *Clin. Chem.* 46:301-302, 2000; Saito et al., *Lancet* 356: 1170, 2000; and Chiu et al., *Lancet* 360:998-1000, 2002) have since been achieved by detecting fetal DNA in maternal plasma or serum using a polymerase chain reaction (PCR)-based technique.

In addition, quantitative abnormalities of fetal DNA in maternal plasma/serum have been reported in preeclampsia (Lo et al., *Clin. Chem.* 45:184-188, 1999 and Zhong et al., *Am. J. Obstet. Gynecol.* 184:414-419, 2001), fetal trisomy 21 (Lo et al., *Clin. Chem.* 45:1747-1751, 1999 and Zhong et al., *Prenat. Diagn.* 20:795-798, 2000) and hyperemesis gravidarum (Sekizawa et al., *Clin. Chem.* 47:2164-2165, 2001). Detection of fetal nucleic acid in maternal blood for prenatal genetic analysis is also disclosed in U.S. Pat. No. 6,258,540.

Fetal RNA present in maternal blood has also been established as a diagnostic tool for pregnancy-associated conditions. For instance, U.S. patent application Ser. No. 09/876,005 discloses non-invasive techniques based on detection of fetal RNA in maternal blood; U.S. patent application Ser. No. 10/759,783 further discloses that the amount of certain mRNA species (e.g., hCG-β, hCRH, hPL, KISS1, TPFI2, and PLAC1) present in maternal blood can be used as markers for diagnosing, monitoring, or predicting pregnancy-related disorders such as preeclampsia, fetal chromosomal aneuploidy, and preterm labor.

Although the stability of DNA provides an advantage for fetal DNA-based diagnosis, one major limitation does exist for this approach: both fetal and maternal DNA is present in the acellular portion of a pregnant woman's blood, e.g., serum or plasma. Thus, there is a need to distinguish fetal DNA from maternal DNA to ensure accurate diagnosis. It was first disclosed in U.S. patent application Ser. No. 09/944,951, published as 20030044388, that fetal and maternal DNA may be distinguished by their different methylation profiles. Landes et al. in U.S. Patent Application Publication No. 20030211522 also proposed differential methylation markers may be used for prenatal diagnosis. In the present disclosure, a number of human genomic DNA sequences located on chromosome 21 are identified for the first time as loci containing regions differentially methylated in genomic DNA originated from a fetus or from an adult (e.g., a pregnant women). Thus, these differentially methylated genomic loci allow proper identification or quantification of fetal and maternal DNA and therefore reliable diagnosis of prenatal conditions.

BRIEF SUMMARY OF THE INVENTION

In the first aspect of this invention, a method is provided for detecting or monitoring a pregnancy-associated disorder in a woman pregnant with a fetus. The method comprises the following steps: (a) obtaining a biological sample from the woman, wherein the sample is whole blood, serum, plasma, urine, or saliva; (b) determining the methylation status of a CpG-containing genomic sequence in the sample, wherein the genomic sequence from the fetus and the genomic sequence from the woman are differentially methylated, thereby distinguishing the genomic sequence from the woman and the genomic sequence from the fetus in the sample, wherein the genomic sequence is at least 15 nucleotides in length, comprising at least one cytosine, and is within a region on chromosome 21, and wherein the region consists of (1) a genomic locus selected from the group consisting of CGI137, phosphodiesterase 9A (PDE9A), homo sapiens protein phosphatase 1, regulatory (inhibitor) subunit 2 pseudogene 2 (PPP1R2P2), Similarity to Fem1A (*Caenorhabditis elegans*), CGI009, carbonyl reductase 1 (CBR1), Down Syndrome cell adhesion molecule (DSCAM), and chromosome 21 open reading frame 29 (C21orf29), Holocarboxylase Synthetase (HLCS), and CGI132; and (2) a DNA sequence of no more than 10 kb upstream and/or downstream from the locus; (c) determining the level of the genomic sequence from the fetus; and (d) comparing the level of the genomic sequence from the fetus with a standard control, wherein an increase or decrease from the standard control indicates the presence or progression of a pregnancy-associated disorder.

In some embodiments, the genomic sequence from the woman is methylated and the genomic sequence from the fetus is unmethylated. In other embodiments, the genomic sequence from the woman is unmethylated and the genomic sequence from the fetus is methylated.

In some embodiments, step (b) is performed by treating the sample with a reagent that differentially modifies methylated and unmethylated DNA. For example, the reagent may comprise bisulfite; or the reagent may comprise one or more enzymes that preferentially cleave methylated DNA; or the reagent may comprise one or more enzymes that preferentially cleave unmethylated DNA. In some embodiments, step (b) is performed by methylation-specific PCR.

In the second aspect of this invention, a method is provided for detecting or monitoring a pregnancy-associated disorder in a woman pregnant with a fetus. The method comprises the steps of: (a) obtaining DNA in a biological sample from the woman, wherein the sample is whole blood, serum, plasma, urine, or saliva; (b) treating the DNA from step (a) with bisulfite; and (c) performing an amplification reaction using the DNA from step (b) and two primers to amplify a CpG-containing genomic sequence, wherein the genomic sequence is at least 15 nucleotides in length, comprises at least one cytosine, and is within a region on chromosome 21, and wherein the region consists of (1) a genomic locus selected from the group consisting of CGI137, phosphodiesterase 9A (PDE9A), homo sapiens protein phosphatase 1, regulatory (inhibitor) subunit 2pseudogene 2 (PPP1R2P2), Similarity to Fem1A (*Caenorhabditis elegans*), CGI009, carbonyl reductase 1 (CBR1), Down Syndrome cell adhesion molecule (DSCAM), chromosome 21 open reading frame 29 (C21orf29), Holocarboxylase Synthetase (HLCS), and CGI132; and (2) a DNA sequence of no more than 10 kb upstream and/or downstream from the locus; and wherein at least one of the two primers binds differentially to the genomic sequence from the fetus; and (d) comparing the level of the amplified portion of the genomic sequence from step (c) with a standard control, wherein an increase or decrease from the standard control indicates the presence or progression of a pregnancy-associated disorder.

In some embodiments, the amplification reaction is a polymerase chain reaction (PCR), such as a methylation-specific PCR. In other embodiments, the amplification reaction is a nucleic acid sequence based amplification, a strand displacement reaction, or a branched DNA amplification reaction.

This method, as well as the method described in the first aspect of this invention, is suitable for detecting or monitoring conditions such as preeclampsia, preterm labor, hyperemesis gravidarum, ectopic pregnancy, a chromosomal aneuploidy (e.g., trisomy 21), and intrauterine growth retardation.

In the third aspect of this invention, a method is provided for detecting and monitoring a pregnancy-associated disorder. The method comprises the steps of: (a) obtaining DNA in a biological sample from the woman, wherein the sample is whole blood, serum, plasma, urine, or saliva; (b) treating the DNA from step (a) with a reagent that differentially modifies methylated and unmethylated DNA; (c) determining the nucleotide sequence of a CpG-containing genomic sequence from step (b), wherein the genomic sequence is at least 15 nucleotides in length, comprises at least one cytosine, and is within a region on chromosome 21, and wherein the region consists of (1) a genomic locus selected from the group consisting of CGI137, phosphodiesterase 9A (PDE9A), homo sapiens protein phosphatase 1, regulatory (inhibitor) subunit 2 pseudogene 2 (PPP1R2P2), Similarity to Fem1A (*Caenorhabditis elegans*), CGI009, carbonyl reductase 1 (CBR1), Down Syndrome cell adhesion molecule (DSCAM), chromosome 21 open reading frame 29 (C21orf29), Holocarboxylase Synthetase (HLCS), and CGI132; and (2) a DNA sequence of no more than 10 kb upstream and/or downstream from the locus; and (d) comparing the profile of the nucleotide sequence from step (c) with a standard control, wherein a change in the profile from the standard control indicates the presence or progression of a pregnancy-associated disorder.

In some embodiments, the reagent comprises bisulfite; or the reagent may comprise one or more enzymes that preferentially cleave methylated DNA; or the reagent may comprise one or more enzymes that preferentially cleave unmethylated DNA.

In some embodiments, the method may further comprise an amplification step of using the DNA from step (b) and two primers to amplify the genomic sequence. For instance, the amplification step can be performed by PCR, such as methylation-specific PCR. In some embodiments, step (c) is performed by mass spectrometry. In other embodiments, step (c) is performed by primer extension. Other possible means for carrying out step (c) includes polynucleotide hybridization, by real-time PCR, and by electrophoresis.

In the fourth aspect of this invention, a method is provided for detecting trisomy 21 in a fetus in a pregnant woman. The method comprises the steps of: (a) obtaining a biological sample from the woman, wherein the sample is whole blood, serum, plasma, urine, or saliva; (b) treating the sample from step (a) with a reagent that differentially modifies methylated and unmethylated DNA; (c) analyzing the alleles of a CpG-containing genomic sequence, wherein the genomic sequence is at least 15 nucleotides in length, comprises at least one cytosine, and is within a region on chromosome 21, and wherein the region consists of (1) a genomic locus selected from the group consisting of CGI137, phosphodiesterase 9A (PDE9A), homo sapiens protein phosphatase 1, regulatory (inhibitor) subunit 2 pseudogene 2 (PPP1R2P2), Similarity to Fem1A (*Caenorhabditis elegans*), CGI009, carbonyl reductase 1 (CBR1), Down Syndrome cell adhesion molecule (DSCAM), chromosome 21 open reading frame 29 (C21orf29), Holocarboxylase Synthetase (HLCS), and CGI132; and (2) a DNA sequence of no more than 10 kb upstream and/or downstream from the locus; and (d) determining the ratio of the alleles, wherein a deviation from that of a woman carrying a fetus not having trisomy 21 indicates trisomy 21 in the fetus.

In some embodiments, the reagent comprises bisulfite. In other embodiments, the reagent comprises one or more enzymes that preferentially cleave methylated DNA. In the alternative, the reagent may comprise one or more enzymes that preferentially cleave unmethylated DNA.

In some embodiments, the method further comprises an amplification step following step (b) to amplify the methylated or unmethylated genomic sequence. The amplification step may be performed by PCR, such as methylation-specific PCR.

There are various possibilities in performing step (c) of the claimed method. For example, step can be performed by mass spectrometry, by a primer extension assay, by real-time PCR, by polynucleotide hybridization, or electrophoresis.

In some embodiments of this method, the two different alleles of the genomic sequence on chromosome 21 from the fetus comprise a single nucleotide polymorphism, an insertion-deletion polymorphism, or a simple tandem repeat polymorphism.

In the fifth aspect of this invention, a method is provided for detecting or monitoring a pregnancy-associated disorder in a woman pregnant with a fetus. The method comprises the steps of: (a) obtaining a biological sample from the woman, wherein the sample is whole blood, serum, plasma, urine, or saliva; (b) determining the level of a CpG-containing genomic sequence in the sample, wherein the genomic sequence is at least 15 nucleotides in length, comprises at least one unmethylated cytosine, and is within a region on chromosome 21, and wherein the region consists of (1) a genomic locus selected from the group consisting of CGI137, phosphodiesterase 9A (PDE9A), homo sapiens protein phosphatase 1, regulatory (inhibitor) subunit 2 pseudogene 2 (PPP1R2P2), and Similarity to Fem1A (*Caenorhabditis elegans*), and (2) a DNA sequence of no more than 10 kb upstream and/or downstream from the locus; and (c) comparing the level of the genomic sequence with a standard control, wherein an increase or decrease from the standard control indicates the presence or progression of a pregnancy-associated disorder.

In some embodiments, step (b) comprises treating DNA present in the blood sample with a reagent that differentially modifies methylated and unmethylated cytosine. This reagent may comprise bisulfite, or it may comprise one or more enzymes that preferentially cleave DNA comprising methylated cytosine, or it may comprise one or more enzymes that preferentially cleave DNA comprising unmethylated cytosine.

In some embodiments, step (b) comprises an amplification reaction, such as a polymerase chain reaction (PCR), especially a methylation-specific PCR. The amplification reaction may also be a nucleic acid sequence based amplification, a strand displacement reaction, a branched DNA amplification reaction. In some embodiments, the level of the genomic DNA sequence is determined by way of electrophoresis or polynucleotide hybridization.

The method is suitable for detecting or monitoring a number of pregnancy-associated disorders, including preeclampsia, preterm labor, hyperemesis gravidarum, ectopic pregnancy, trisomy 21, and intrauterine growth retardation.

In the sixth aspect of this invention, a method for detecting or monitoring a pregnancy-associated disorder in a woman pregnant with a fetus. The method comprises the steps of: (a) obtaining a biological sample from the woman, wherein the sample is whole blood, serum, plasma, urine, or saliva; (b) determining the level of a CpG-containing genomic sequence in the sample, wherein the genomic sequence is at least 15 nucleotides in length, comprises at least one methylated cytosine, and is within a region on chromosome 21, and wherein the region consists of (1) a genomic locus selected from the group consisting of CGI009, carbonyl reductase 1 (CBR1), Down Syndrome cell adhesion molecule (DSCAM), chromosome 21 open reading frame 29 (C21orf29), Holocarboxylase Synthetase (HLCS), and CGI132, and (2) a DNA sequence of no more than 10 kb upstream and/or downstream from the locus; and (c) comparing the level of the genomic sequence with a standard control, wherein an increase or decrease from the standard control indicates the presence or progression of a pregnancy-associated disorder.

In some embodiments, step (b) comprises treating DNA present in the blood sample with a reagent that differentially modifies methylated and unmethylated cytosine. This reagent may comprise bisulfite, or it may comprise one or more enzymes that preferentially cleave DNA comprising methylated cytosine, or it may comprise one or more enzymes that preferentially cleave DNA comprising unmethylated cytosine.

In some embodiments, step (b) comprises an amplification reaction, such as a polymerase chain reaction (PCR), especially a methylation-specific PCR. The amplification reaction may also be a nucleic acid sequence based amplification, a strand displacement reaction, a branched DNA amplification reaction. In some embodiments, the level of the genomic DNA sequence is determined by way of electrophoresis or polynucleotide hybridization.

The method is suitable for detecting or monitoring a number of pregnancy-associated disorders, including preeclampsia, preterm labor, hyperemesis gravidarum, ectopic pregnancy, trisomy 21, and intrauterine growth retardation.

In practicing the present invention within all aspects mentioned above, a CpG island may be used as the CpG-containing genomic sequence in some cases, whereas in other cases the CpG-containing genomic sequence may not be a CpG island.

BRIEF DESCRIPTION OF THE DRAWINGS

FIG. 7. Box plot of the methylation indices among all of the sequenced clones for the placenta and maternal blood cell samples for each of the studied CpG sites within Carbonyl reductase 1. Across the x-axis, the individual CpG sites are designated with their nucleotide positions relative to chr21: 36,363,538 (+1) of the Human May 2004 (hg17) assembly of the UCSC Genome Browser.

FIG. 8. Box plot of the methylation indices among all of the sequenced clones for the placenta and maternal blood cell samples for each of the studied CpG sites within Down syndrome cell adhesion molecule. Across the x-axis, the individual CpG sites are designated with their nucleotide positions relative to chr21: 41,139,872 (+1) of the Human May 2004 (hg17) assembly of the UCSC Genome Browser.

FIG. 9. Box plot of the methylation indices among all of the sequenced clones for the placenta and maternal blood cell samples for each of the studied CpG sites within C21orf29. Across the x-axis, the individual CpG sites are designated with their nucleotide positions relative to chr21: 44,953,288 (+1) of the Human May 2004 (hg17) assembly of the UCSC Genome Browser.

FIG. 10. Cloning and bisulfite sequencing of CGI111 among paired placental tissues and maternal blood cells. Individual CpG sites are numbered across the first row, with nucleotide positions defined relative to chr21: 44,699,072 (+1) of the Human May 2004 (hg17) assembly of the UCSC Genome Browser. Each subsequent row depicts the methylation status across the CpG sites in a single DNA molecule isolated by cloning. Filled and unfilled circles represent methylated and unmethylated CpG sites, respectively. Clones from placental tissue samples are labeled with a prefix "PLN," while that from maternal blood cells are labeled with a prefix "MBN." Placenta and maternal blood cells from the same pregnant individual are identified by identical sample number following the "PLN" or "MBN."

FIG. 11. Box plot of the methylation indices among all of the sequenced clones for the placenta and maternal blood cell samples for each of the studied CpG sites within CGI121. Across the x-axis, the individual CpG sites are designated with their nucleotide positions relative to chr21: 45,262,112 (+1) of the Human May 2004 (hg17) assembly of the UCSC Genome Browser.

FIG. 12. Illustration of the homogeneous MassEXTEND assay targeting the unmethylated form of CGI137. The nucleotide sequence spanning the amplified region is shown. The original DNA sequence (SEQ ID NO:1) is aligned above the bisulfite-converted sequence (SEQ ID NO:2). CpG sites are identified by the "++" sign. The CpG sites are additionally numbered and the numbering corresponds to that in FIGS. 1A and 2A and Table 2A. Cytosine residues which are not part of a CpG dinucleotide are identified by a ":" sign. The depicted bisulfite-converted sequence is based on the assumption that all CpG sites are methylated. Alignments for the forward, extension and reverse primers (SEQ ID NOS:3-5) are shown below the bisulfite-converted sequence.

DEFINITIONS

Figure 1A:
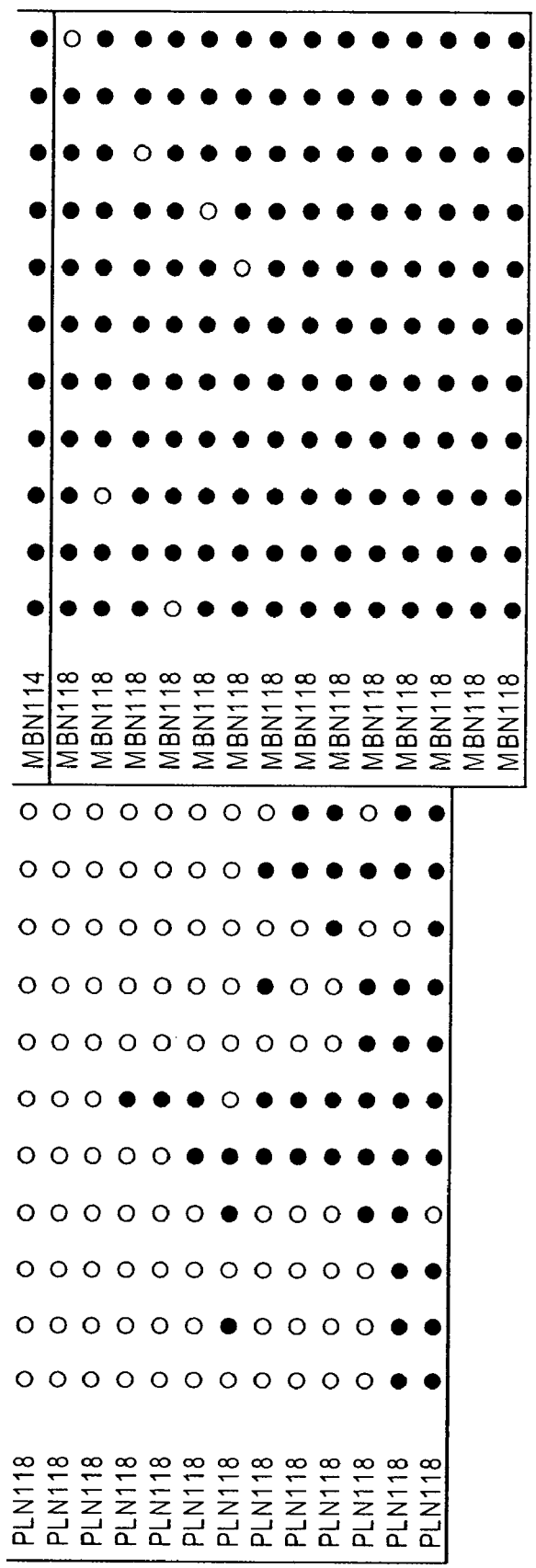
FIG. 1. Cloning and bisulfite sequencing of CGI137 (A). region A and (B). region B among paired placental tissues and maternal blood cells. Individual CpG sites are numbered across the first row, with nucleotide positions defined relative to chr21:46,249,636 (+1) of the Human May 2004 (hg17) assembly of the UCSC Genome Browser. Each subsequent row depicts the methylation status across the CpG sites in a single DNA molecule isolated by cloning. Filled and unfilled circles represent methylated and unmethylated CpG sites, respectively. Clones from placental tissue samples are labeled with a prefix "PLN," while those from maternal blood cells are labeled with a prefix "MBN." Placenta and maternal blood cells from the same pregnant individual are identified by identical sample number following the "PLN" or "MBN."

The term "pregnancy-associated disorder," as used in this application, refers to any condition or disease that may affect a pregnant woman, the fetus the woman is carrying, or both the woman and the fetus. Such a condition or disease may manifest its symptoms during a limited time period, e.g., during pregnancy or delivery, or may last the entire life span of the fetus following its birth. Some examples of a pregnancy-associated disorder include ectopic pregnancy, preeclampsia, preterm labor, and fetal chromosomal abnormalities such as trisomy 21.

A "CpG-containing genomic sequence" as used herein refers to a segment of DNA sequence at a defined location in the genome of an individual such as a human fetus or a pregnant woman. Typically, a "CpG-containing genomic sequence" is at least 15 nucleotides in length and contains at least one cytosine. Preferably, it can be at least 30, 50, 80, 100, 150, 200, 250, or 300 nucleotides in length and contains at least 2, 5, 10, 15, 20, 25, or 30 cytosines. For any one "CpG-containing genomic sequence" at a given location, e.g., within a region centering around a given genetic locus on chromosome 21 (such as a CpG island CGI137, PDE9A, CGI009, etc.), nucleotide sequence variations may exist from individual to individual and from allele to allele even for the same individual. Typically, such a region centering around a defined genetic locus (e.g., a CpG island) contains the locus as well as upstream and/or downstream sequences. Each of the upstream or downstream sequence (counting from the 5' or 3' boundary of the genetic locus, respectively) can be as long as 10 kb, in other cases may be as long as 5 kb, 2 kb, 1 kb, 500 bp, 200 bp, or 100 bp. Furthermore, a "CpG-containing genomic sequence" may encompass a nucleotide sequence transcribed or not transcribed for protein production, and the nucleotide sequence can be a protein-coding sequence, a non protein-coding sequence (such as a transcription promoter), or a combination thereof.

A "CpG island" in this application describes a segment of DNA sequence found in a genome that has a minimal length, a minimal GC content, and a minimal ratio of observed CpG frequency/expected CpG frequency (OCF/ECF). Yamada et al. (Genome Research 14:247-266, 2004) have described a set of standards for determining a CpG island: it must be at least 400 nucleotides in length, has a greater than 50% GC content, and an OCF/ECF ratio greater than 0.6. Others (Takai et al., *Proc. Natl. Acad. Sci. U.S.A.* 99:3740-3745, 2002) have defined a CpG island less stringently as a sequence at least 200 nucleotides in length, having a greater than 50% GC content, and an OCF/ECF ratio greater than 0.6. The concept of a "CpG island" on chromosome 21, as used in this application, is one that fits the CpG island profiles provided by any one of the currently available computational programs designed for scanning chromosomes based on the above stated criteria, encompassing results obtained when using window sizes of 100, 200, or 300 nucleotides and shift or step sizes of 1, 2, or 3 nucleotides in the screening process. The individual CpG islands named in this disclosure are further defined by their corresponding genomic contig accession number, version and region at GenBank, chromosomal location relative to the chromosome 21 sequence of the Human May 2004 (hg17) assembly of the UCSC Genome Browser (genome.ucsc.edu), and their capability to be amplified by PCR primers under given conditions, as indicated in Table 1 of this specification.

The term "epigenetic state" or "epigenetic status" as used herein refers to any structural feature at a molecular level of a nucleic acid (e.g., DNA or RNA) other than the primary nucleotide sequence. For instance, the epigenetic state of a genomic DNA may include its secondary or tertiary structure determined or influenced by, e.g., its methylation pattern or its association with cellular proteins.

The term "methylation profile" or "methylation status," when used in this application to describe the state of methylation of a genomic sequence, refers to the characteristics of a DNA segment at a particular genomic locus relevant to methylation. Such characteristics include, but are not limited to, whether any of the cytosine (C) residues within this DNA sequence are methylated, location of methylated C residue(s), percentage of methylated C at any particular stretch of residues, and allelic differences in methylation due to, e.g., difference in the origin of the alleles. The term "methylation profile" or "methylation status" also refers to the relative or absolute concentration of methylated C or unmethylated C at any particular stretch of residues in a biological sample.

The term "single nucleotide polymorphism" or "SNP" as used herein refers to the polynucleotide sequence variation present at a single nucleotide residue within different alleles of the same genomic sequence. This variation may occur within the coding region or non-coding region (i.e., in the promoter region) of a genomic sequence, if the genomic sequence is transcribed during protein production. Detection of one or more SNP allows differentiation of different alleles of a single genomic sequence.

The term "blood" as used herein refers to a blood sample or preparation from a pregnant woman or a woman being tested for possible pregnancy. The term encompasses whole blood or any fractions of blood, such as serum and plasma as conventionally defined.

The term "bisulfite" as used herein encompasses all types of bisulfites, such as sodium bisulfite, that are capable of chemically converting a cytosine (C) to a uracil (U) without chemically modifying a methylated cytosine and therefore can be used to differentially modify a DNA sequence based on the methylation status of the DNA.

As used herein, a reagent that "differentially modifies" methylated or non-methylated DNA encompasses any reagent that modifies methylated and/or unmethylated DNA in a process through which distinguishable products result from methylated and non-methylated DNA, thereby allowing the identification of the DNA methylation status. Such processes may include, but are not limited to, chemical reactions (such as a C→U conversion by bisulfite) and enzymatic treatment (such as cleavage by a methylation-dependent endonuclease). Thus, an enzyme that preferentially cleaves or digests methylated DNA is one capable of cleaving or digesting a DNA molecule at a much higher efficiency when the DNA is methylated, whereas an enzyme that preferentially cleaves or digests unmethylated DNA exhibits a significantly higher efficiency when the DNA is not methylated.

The term "nucleic acid" or "polynucleotide" refers to deoxyribonucleic acids (DNA) or ribonucleic acids (RNA) and polymers thereof in either single-or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used in this application, an "increase" or a "decrease" refers to a detectable positive or negative change in quantity from an established standard control. An increase is a positive change preferably at least 10%, more preferably 50%, still more preferably 2-fold, even more preferably at least 5-fold, and most preferably at least 10-fold of the control value. Similarly, a decrease is a negative change preferably at least 10%, more preferably 50%, still more preferably at least 80%, and most preferably at least 90% of the control. Other terms indicating quantitative changes or differences from a comparative basis, such as "more" or "less," are used in this application in the same fashion as described above.

A "polynucleotide hybridization method" as used herein refers to a method for detecting the presence and/or quantity of a polynucleotide based on its ability to form Watson-Crick base-pairing, under appropriate hybridization conditions, with a polynucleotide probe of a known sequence. Examples of such hybridization methods include Southern blotting and Northern blotting.

"Primers" as used herein refer to oligonucleotides that can be used in an amplification method, such as a polymerase chain reaction (PCR), to amplify a nucleotide sequence based on the polynucleotide sequence corresponding to a particular genomic sequence, e.g., one located within the CpG island CGI137, PDE9A, or CGI009 on chromosome 21, in various methylation status. At least one of the PCR primers for amplification of a polynucleotide sequence is sequence-specific for the sequence.

"Standard control" as used herein refers to a sample comprising a genomic sequence of a predetermined amount or methylation profile (which may include multiple different and separable characteristics related to methylation) suitable for the use of a method of the present invention, in order for comparing the amount or methylation status of a particular genomic sequence, e.g., one located within the CpG island CGI137, PDE9A, or CGI009 on chromosome 21, that is present in a test sample. A sample serving as a standard control provides an average amount or methylation profile of a gene of interest that is typical for a defined time (e.g., first trimester) during pregnancy in the blood of an average, healthy pregnant woman carrying a normal fetus, both of who are not at risk of developing any pregnancy-associated disorders or complications.

The term "average," as used in the context of describing a pregnant woman, refers to the fact that the woman is free of at least one condition of relevance, such as having a chromosomally abnormal fetus, or suffering from a pregnancy-associated condition (e.g., ectopic pregnancy, preeclampsia or preterm labor). The term "average," when used in other context, refers to certain characteristics, such as the methylation profile of a particular genomic sequence (e.g., one located within the CpG island CGI137, PDE9A, or CGI009 on chromosome 21) of both maternal and fetal origins found in the woman's blood, that are representative of a randomly selected group of healthy women who are pregnant with chromosomally normal fetuses and not susceptible to any pregnancy-related diseases or conditions. This selected group should comprise a sufficient number of women such that the average amount or methylation profile of the genomic sequence of interest among these women reflects, with reasonable accuracy, the corresponding profile in the general population of healthy pregnant women with healthy fetuses. In addition, the selected group of women generally has a similar gestational age to that of a woman whose blood is tested for indication of a potential pregnancy-associated disorder. The preferred gestational age for practicing the present invention may vary depends on the disorder that is being screened for. For example, a pregnant woman is screened for the risk of preeclampsia preferably during the second trimester of the pregnancy, whereas fetal chromosomal aneuploidy is preferably screened for and diagnosed as early as possible. Moreover, the preferred gestational age for testing may also depend on the gene of interest in testing.

The term "preeclampsia" as used herein refers to a condition that occurs during pregnancy, the main symptom of which is various forms of high blood pressure often accompanied by the presence of proteins in the urine and edema (swelling). Preeclampsia, sometimes called toxemia of pregnancy, is related to a more serious disorder called "eclampsia," which is preeclampsia together with seizures. These conditions usually develop during the second half of pregnancy (after 20 weeks), though they may develop shortly after birth or before 20 weeks of pregnancy.

The term "preterm labor" or "premature labor" as used herein refers to the condition where labor that begins more than three weeks before the full gestation period of about 40 weeks, which often leads to premature birth if not treated.

The term "hyperemesis gravidarum" refers to extreme, persistent nausea and vomiting during pregnancy, particularly during the first trimester. The nausea and vomiting may lead to dehydration and prevent necessary weight gain for the pregnancy.

An "ectopic pregnancy" refers to an abnormal pregnancy in which a fertilized egg has implanted outside the uterus. Although in most cases of ectopic pregnancy the egg settles in the fallopian tubes, this term also encompasses abnormal pregnancies where the fertilized egg is implanted in a woman's ovary, abdomen, or cervix.

DETAILED DESCRIPTION OF THE INVENTION

I. Introduction

The presence of fetal DNA in maternal plasma was first reported in 1997 and offers the possibility for non-invasive prenatal diagnosis simply through the analysis of a maternal blood sample (Lo et al., *Lancet* 350:485-487, 1997). To date, numerous potential clinical applications have been developed. In particular, quantitative abnormalities of fetal DNA concentrations in maternal plasma have been found to be associated with a number of pregnancy-associated disorders, including preeclampsia, preterm labor, antepartum hemorrhage, invasive placentation, fetal Down syndrome, and other fetal chromosomal aneuploidies. Hence, fetal DNA analysis in maternal plasma has been suggested as a potential marker for the monitoring of fetomaternal well-being.

However, fetal DNA co-exists with background maternal DNA in maternal plasma. Hence, most reported applications have relied on the detection of Y-chromosome sequences as these are most conveniently distinguishable from maternal DNA. Such an approach limits the applicability of the existing assays to only 50% of all pregnancies, namely those with male fetuses. Thus, there is much need for the development of gender-independent fetal DNA markers for maternal plasma detection.

It was previously demonstrated that fetal and maternal DNA can be distinguished by their differences in methylation status (U.S. Patent Application Publication No. 20030044388). Methylation is an epigenetic phenomenon, which refers to processes that alter a phenotype without involving changes in the DNA sequence. By exploiting the difference in the DNA methylation status between the paternally-and maternally-inherited alleles at H19, a locus exhibiting genomic imprinting (differential methylation and hence differential expression of two alleles of a single gene, related to the parental origin of a particular allele), one (Y. M. D. Lo) of the present inventors and his group first demonstrated the feasibility of using epigenetic markers to detect fetal-derived maternally-inherited DNA sequence from maternal plasma (Poon et al., *Clin. Chem.* 48:35-41, 2002). Landes et al. have also proposed the use of epigenetic markers for non-invasive prenatal diagnosis (U.S. Patent Application Publication No. 20030211522).

The present inventors have recently demonstrated that placenta-derived RNA can be detected in maternal plasma (Ng et al., *Proc. Natl. Acad. Sci. USA* 100:4748-4753, 2003). On the other hand, it has been shown that plasma DNA in normal individuals is predominantly derived from hematopoietic cells (Lui et al., *Clin. Chem.* 48:421-427, 2002). Thus, it has been hypothesized that the predominant source of maternal DNA is derived from peripheral blood cells while the placenta is a possible source of fetal DNA release into maternal plasma. Hence, one strategy for the development of a generic fetal-specific DNA marker for detection in maternal plasma is to identify a gene that is differentially methylated between the placenta and the maternal peripheral blood cells.

The present inventors demonstrated, for the first time, that a number of genomic sequences located at specific genomic loci on chromosome 21 are differentially methylated between the fetal DNA from the fetus (e.g., from the placenta) and the maternal DNA from the mother's peripheral blood cells. This discovery thus provides a new approach for distinguishing fetal and maternal genomic DNA and new methods for non-invasive prenatal diagnosis.

II. General Methodology

Practicing this invention utilizes routine techniques in the field of molecular biology. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984).

Purification of oligonucleotides is performed using any art-recognized strategy, e.g., native acrylamide gel electrophoresis or anion-exchange high performance liquid chromatography (HPLC) as described in Pearson & Reanier, *J. Chrom.* 255: 137-149 (1983).

The genomic sequences of the present invention, e.g., those located within the CpG islands on chromosome 21 such as CGI137, PDE9A, and CGI009, and the polynucleotide sequence of synthetic oligonucleotides can be verified using, e.g., the chain termination method for sequencing double-stranded templates of Wallace et al., *Gene* 16: 21-26 (1981).

III. Acquisition of Blood Samples and Extraction of DNA

The present invention relates to analyzing the epigenetic status of fetal DNA found in maternal blood as a non-invasive means to detect the presence and/or to monitor the progress of a pregnancy-associated condition or disorder. Thus, the first steps of practicing this invention are to obtain a blood sample from a pregnant woman and extract DNA from the sample.

A. Acquisition of Blood Samples

A blood sample is obtained from a pregnant woman at a gestational age suitable for testing using a method of the present invention. The suitable gestational age may vary depending on the disorder tested, as discussed below. Collection of blood from a woman is performed in accordance with the standard protocol hospitals or clinics generally follow. An appropriate amount of peripheral blood, e.g., typically between 5-50 ml, is collected and may be stored according to standard procedure prior to further preparation.

B. Preparation of Blood Samples

The analysis of fetal DNA found in maternal blood according to the present invention may be performed using, e.g., the whole blood, serum, or plasma. The methods for preparing serum or plasma from maternal blood are well known among those of skill in the art. For example, a pregnant woman's blood can be placed in a tube containing EDTA or a specialized commercial product such as Vacutainer SST (Becton Dickinson, Franklin Lakes, N.J.) to prevent blood clotting, and plasma can then be obtained from whole blood through centrifugation. On the other hand, serum may be obtained with or without centrifugation-following blood clotting. If centrifugation is used then it is typically, though not exclusively, conducted at an appropriate speed, e.g., 1,500-3,000× g. Plasma or serum may be subjected to additional centrifugation steps before being transferred to a fresh tube for DNA extraction.

In addition to the acellular portion of the whole blood, DNA may also be recovered from the cellular fraction, enriched in the buffy coat portion, which can be obtained following centrifugation of a whole blood sample from the woman and removal of the plasma.

C. Extraction of DNA

There are numerous known methods for extracting DNA from a biological sample including blood. The general methods of DNA preparation (e.g., described by Sambrook and Russell, *Molecular Cloning: A Laboratory Manual* 3d ed., 2001) can be followed; various commercially available reagents or kits, such as QiaAmp DNA Mini Kit or QiaAmp DNA Blood Mini Kit (Qiagen, Hilden, Germany), GenomicPrep™ Blood DNA Isolation Kit (Promega, Madison, Wis.), and GFX™ Genomic Blood DNA Purification Kit (Amersham, Piscataway, N.J.), may also be used to obtain DNA from a blood sample from a pregnant woman. Combinations of more than one of these methods may also be used.

IV. Methylation-Specific Chemical Modification of DNA

Upon being extracted from a blood sample of a pregnant woman, the DNA is treated with a reagent capable of chemically modifying DNA in a methylation differential manner, i.e., different and distinguishable chemical structures will result from a methylated cytosine (C) residue and an unmethylated C residue following the treatment. Typically, such a reagent reacts with the unmethylated C residue(s) in a DNA molecule and converts each unmethylated C residue to a uracil (U) residue, whereas the methylated C residues remain unchanged. This C→U conversion allows detection and comparison of methylation status based on changes in the primary sequence of the nucleic acid. An exemplary reagent suitable for this purpose is bisulfite, such as sodium bisulfite. Methods for using bisulfite for chemical modification of DNA are well known in the art (see, e.g., Herman et al., *Proc. Natl. Acad. Sci. USA* 93:9821-9826, 1996) and will not be discussed in detail here.

As a skilled artisan will recognize, any other reagents that are unnamed here but have the same property of chemically (or through any other mechanism) modifying methylated and unmethylated DNA differentially can be used for practicing the present invention. For instance, methylation-specific modification of DNA may also be accomplished by methylation-sensitive restriction enzymes, some of which typically cleave an unmethylated DNA fragment but not a methylated DNA fragment, while others (e.g., methylation-dependent endonuclease McrBC) cleave DNA containing methylated cytosines but not unmethylated DNA. In addition, a combination of chemical modification and restriction enzyme treatment, e.g., combined bisulfite restriction analysis (COBRA), may be used for practicing the present invention.

V. Polynucleotide Sequence Amplification and Determination

Following the chemical modification of DNA in a methylation-differential manner, the treated DNA is then subjected to sequence-based analysis, such that one or more of the genomic sequences of the present invention (e.g., those located within the CpG islands on chromosome 21 such as CGI137, PDE9A, and CGI009) from the fetal DNA may be distinguished from their counterparts from the maternal DNA, and that fetal genomic sequence methylation profile may be determined and compared to a standard control. Furthermore, once it is determined that one particular genomic sequence of fetal origin is hypermethylated or hypomethylated compared to the maternal counterpart, the amount of this fetal genomic sequence can be determined based on its specific methylation status. Subsequently, this amount can be compared to a standard control value and serve as an indication for the potential of certain pregnancy-associated disorder.

A. Amplification of Nucleotide Sequences

An amplification reaction is optional prior to sequence analysis for a genomic sequence after methylation specific modification. In some embodiments of this invention, the amplification is performed to preferentially amplify a CpG-containing genomic sequence on chromosome 21 that has a particular methylation pattern, such that only the genomic sequence from one particular source, e.g., from the placenta or other tissues of the fetus, is detected and analyzed.

A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of a target polynucleotide sequence (e.g., a CpG-containing genomic sequence on chromosome 21 where the fetal and maternal sequence is differentially methylated) is typically used in practicing the present invention, one of skill in the art will recognize that the amplification of a genomic sequence found in a maternal blood sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to qualitatively demonstrate the presence of a particular genomic sequence of this invention, which represents a particular methylation pattern, or to quantitatively determine the amount of this particular genomic sequence in the maternal blood. For a review of branched-DNA signal amplification for direct quantitation of nucleic acid sequences in clinical samples, see Nolte, *Adv. Clin. Chem.* 33:201-235, 1998.

B. Determination of Polynucleotide Sequences

Techniques for polynucleotide sequence determination are also well established and widely practiced in the relevant research field. For instance, the basic principles and general techniques for polynucleotide sequencing are described in various research reports and treatises on molecular biology and recombinant genetics, such as Wallace et al., supra; Sambrook and Russell, supra, and Ausubel et al., supra. DNA sequencing methods routinely practiced in research laboratories, either manual or automated, can be used for practicing the present invention. Additional means suitable for detecting changes (e.g., C→U) in a polynucleotide sequence for practicing the methods of the present invention include but are not limited to mass spectrometry, primer extension, polynucleotide hybridization, real-time PCR, and electrophoresis.

VI. Establishing a Standard Control

In order to establish a standard control for practicing the method of this invention, a group of healthy pregnant women carrying healthy fetuses are first selected. These women are of similar gestational age, which is within the appropriate time period of pregnancy for screening of conditions such as preeclampsia, fetal chromosomal aneuploidy, and preterm labor using the methods of the present invention. Similarly, a standard control is established using samples from a group of healthy non-pregnant women.

The healthy status of the selected pregnant women and the fetuses they are carrying are confirmed by well established, routinely employed methods including but not limited to monitoring blood pressure of the women, recording the onset of labor, and conducting fetal genetic analysis using CVS and amniocentesis.

Furthermore, the selected group of healthy pregnant women carrying healthy fetuses must be of a reasonable size, such that the average amount of a genomic sequence of this invention that originated from the fetus in the maternal blood or the methylation profile of the fetal genomic sequence in the maternal blood obtained from the group can be reasonably regarded as representative of the normal or average amount or methylation profile among the general population of healthy women carrying healthy fetuses. Preferably, the selected group comprises at least 10 women.

A standard control for a fetal genomic sequence methylation profile may reflect multiple different and separable aspects of the methylation status of this particular genomic sequence. For example, one aspect of a methylation profile is whether any given C residue is methylated or not; another aspect is the number of methylated C bases within a particular genomic sequence; a further aspect of the profile is the percentage(s) of methylated C at any given locations. Additional aspects of a methylation profile may include, but are not limited to, the allelic difference in methylation, the ratio of differentially methylated alleles, and the like. Fetal genomic sequence methylation profile may also vary depending on the tissue type, e.g., placental or other fetal tissue. Thus, separate standard controls may be established for different fetal tissues used in testing.

Once an average level or methylation profile is established for a particular fetal genomic sequence present in the maternal blood based on the individual values found in each woman of the selected healthy control group, this average or median or representative value or profile is considered a standard control. Any blood sample that contains a similar amount of the fetal genomic sequence or a similar methylation profile of the fetal genomic sequence can thus be used as a standard control. Furthermore, a solution containing a genomic DNA sequence in the average or median or representative amount or of the average or median or representative methylation profile can also be artificially assembled and serve as a standard control. In addition, separate standard controls may also be established for different aspects of the methylation profile of a genomic sequence of the fetal origin.

EXAMPLES

The following examples are provided by way of illustration only and not by way of limitation. Those of skill in the art will readily recognize a variety of non-critical parameters that could be changed or modified to yield essentially the same or similar results.

Example 1

We aimed to identify epigenetic markers that are fetal-specific in maternal blood. Previous data suggest that fetal DNA molecules in maternal plasma are predominantly derived from the placenta (Chim et al., *Proc Natl Acad Sci U S A.*, 102:14753-14758; Masuzaki et al., *J Med Genet* 41, 289-292, 2004; Flori et al., *Hum Reprod* 19, 723-724, 2004), while the background DNA in maternal plasma may originate from maternal blood cells (Lui et al., *Clin Chem* 48, 421-427, 2002). Hence, to identify fetal epigenetic markers, the methylation profiles of genetic loci were assessed in both placental tissues and maternal blood cells with an aim to identify loci that demonstrate differential methylation between the two tissue types. Such markers can be used for prenatal diagnosis and monitoring of pregnancy-related conditions.

Materials and Methods

Identification of CpG-containing genomic sequences DNA methylation refers to the addition of a methyl group to the fifth carbon position of cytosine residues in CpG dinucleotides. Clusters of such CpG dinucleotides on chromosome 21q were computationally identified through the Genome Browser of the UCSC Genome Bioinformatics Site (website: genome.ucsc.edu/,followed by cgi-bin/hgGateway) (Yamada et al., *Genome Res* 14, 247-266, 2004). The CpG sites were further subselected based on the criteria: a stretch of DNA sequence of at least 400 bp in length with a minimal guanine and cytosine content of 50%, and a minimal ratio of observed CpG frequency/expected CpG frequency of at least 0.6. After CpG containing genomic sequences are identified, we also branched out to CpG sites further up- and downstream to the previously identified genomic region, e.g., PDE9A regions A and C.

Subject recruitment and sample collection Placental tissues and corresponding blood samples were collected from women in the first and third trimesters of pregnancy. Placental tissues were collected from the third-trimester subjects after cesarean delivery and from the first trimester subjects after termination of pregnancy. Maternal blood (10 mL) was collected into EDTA blood tubes prior to the onset of labor or the performance of any obstetrics procedures. The blood samples were centrifuged at 1600×g for 10 min at 4° C. The buffy coat portion was obtained after careful removal of plasma and stored separately at −20° C. The placental tissues were rinsed in phosphate buffered saline and stored in plain polypropylene tubes at −80° C.

Bisulfite sequencing DNA was extracted from the placental tissues and maternal buffy coat by using the QIAamp DNA Mini Kit and QIAamp DNA Blood Mini Kit (Qiagen, Hilden, Germany), respectively, according to the manufacturer's instructions. For each sample, 1 μg DNA was subjected to bisulfite conversion, which converts unmethylated cytosine residues to uracil but leaves methylated cytosine residues unchanged, by the CpGenome DNA Modification Kit (Intergen, Burlington, Mass.) according to manufacturer's instructions. The bisulfite converted DNA was then subjected to PCR amplification with pairs of primers flanking the CpG sites (Table 1). Some CpG-containing genomic sequences are investigated by two or three PCRs, namely regions A, B and C. Primers were designed not to bind to any potentially methylated cytosine residues. These primers are shown by way of illustration and should not be seen to limit the range of primers which can be used for this purpose. Reagents supplied in the TaqMan PCR Core Reagent Kit (Applied Biosystems, Foster City, Calif.) were used. Reagent compositions for each PCR are detailed in Table 1. Typically, PCRs were performed in a final reaction volume of 25 μl, with $MgCl_2$, primers, TaqGold, 1× Buffer II, 200 μM of each dNTP, with or without dimethylsulfoxide (DMSO) or betaine. The thermal profile consisted of an initial denaturation step of 95° C. for 10 min followed by 40 cycles of 95° C. for 1 min, a range of annealing temperatures between 55 to 65 °C. for 1 min (Table 1), 72° C. for 1 min, and a final extension of 72° C. for 10 min. To analyze methylation status at the resolution of a single molecule, the PCR product was TA-cloned into a plasmid vector using the pGEM-T Easy Vector System (Promega, Madison, Wis.). The inserts from the positive recombinant clones were analyzed by cycle sequencing using the BigDye Terminator Cycle Sequencing v1.1 kit (Applied Biosystems) as per the manufacturer's instructions. After purification by genCLEAN columns (Genetix), 8 μl of the samples were added to 12 μl of Hi-Di formamide and run on a 3100 DNA Analyzer (Applied Biosystems).

TABLE 1

Identity, location, primer sequences and PCR reaction conditions of the studied genomic sequences on chromosome 21. The respective regions on genomic contigs (accession number, version, start and end nucleotide numbers) deposited at GenBank of the National Center for Biotechnology Information and chromosomal locations (chromosome, start and end nucleotide numbers) on the Human May 2004 (hg17) assembly of the UCSC genome browser (available at genome.ucsc.edu web site) are shown in the second and third columns, respectively.

| Sequence name | Region on genomic contig | Chromosomal location | F-primer (5'-3') | SEQ ID NO: | R-primer (5'-3') |
|---|---|---|---|---|---|
| CGI137 region A | NT_011515.11: 2742901-2743142 | chr21:46, 249, 993-46, 250, 234 | GGTTGGGTTG GAGGAGGGTAGT | 6 | ACCCCRAACCC RTCTCTACCTACAA |
| CGI137 region B | NT_011515.11: 2742666-2743001 | chr21:46, 249, 758-46, 250, 093 | AAGGGGAGTTGAGA TATTGTAGGGTTAT | 8 | AACACCTAAA AAACTCRCCRAAA |
| PDE9A region A | NT_030188.4: 1099474-1099776 | chr21:42, 978, 102-42, 978, 404 | GTTTTTAGGGAGG GGGTATTTYGAGT | 10 | AATCTATTTTCTATATTTC ACTATTTCCAAATAAAA |
| PDE9A region B | NT_030188.4: 1100569-1100940 | chr21:42, 979, 197-42, 979, 568 | GTATGTATTAATTAAATG AAAAGATGAGTTTGTGAT | 12 | CRAAAAACCCCTT ATAAAAAACCRA |
| PDE9A region C | NT_030188.4: 1101439-1101851 | chr21:42, 980, 067-42, 980, 479 | GGTGGTTGTGTGT GTTTGGTTTTTAGT | 14 | ACCCAAAAATAC CCCAAACCATAAA |
| PPP1R2P2 region A | NT_011512.10: 22921010-22921356 | chr21:36, 181, 010-36, 181, 356 | AGGTTTTTTAGTG GGGAAAAAATGGT | 16 | CRAAACTTCCRACTCT TAACTCAAAATAACTA |
| PPP1R2P2 region B | NT_011512.10: 22921311-22921479 | chr21:36, 181, 311-36, 181, 479 | GATTTTAYGTYGA GTAGTTATTTGAGTTAAG | 18 | AACTCCTCRTCC ACACTCCRTA |
| Similarity to Fem1A (C. elegans) region A | NT_011512.10: 796376-796709 | chr21:14, 056, 376-14, 056, 709 | AGGTTAATGATTTGTATATT TAAAAGTTTTTAGGATATTT | 20 | ACCAAATACTCCAC CACRTCCAAATAA |
| Similarity to Fem1A (C. elegans) region B | NT_011512.10: 796679-796961 | chr21:14, 056, 679-14, 056, 961 | AYGGTTATTTGGA YGTGGTGGAGTATT | 22 | CCRATTAACCACCTC CAAATTAACCTAATA |
| CGI009 | NT_011512.10: 12596247-12596458 | chr21:25, 856, 247-25, 856, 458 | AAAAAGGYGTTTGG TYGGTTATGAGTTAT | 24 | AAACTAAAATCR ACRTACCTACAA |
| CBR1 | NT_011512.10: 23103970-23104340 | chr21:36, 363, 970-36, 364, 340 | GTTAYGTGGGTAGTTAATAG TTAGTAGTTAGAGATTAGTT | 26 | CAAACCRATACCC TTATTACCTCCAA |
| DSCAM | NT_011512.10: 27880652-27880936 | chr21:41, 140, 652-41, 140, 936 | YGYGYGTTGYGTTT TTGTATATTTGTTTT | 28 | CAAAAAAAATTAACAAA AAATCCATATAACTAAAA |
| C21orf29 | NT_011515.11: 1446687-1446915 | chr21:44, 953, 779-44, 954, 007 | AGTTTGGTAGTTATTTG AATAGTTAAATGAGTT | 30 | AACTTTCTCATCCTA CTCCCTAAATCTATA |
| CGI111 | NT_011515.11: 1193113-1193374 | chr21:44, 700, 205-44, 700, 466 | TTTTTTTAGGTAG TTGAAAGAAAAGG | 32 | CCTCCCTCCT CAAAATAAAC |
| CGI121 | NT_011515.11: 1756431-1756699 | chr21:45, 263, 523-45, 263, 791 | TTTTTAGATATTTT TGGGTTTAAGGTT | 34 | AAATCCACCTA CCCAAACACC |
| KIAA0656 region A | NT_011512.10: 1097983-1098273 | chr21:14, 357, 983-14, 358, 273 | TTGGTGGTYGYGAAG TGTTTTTGTTAGTATT | 36 | ACCTCTCAAACCRAA TAAACCTAACAAAAC |
| KIAA0656 region B | NT_011512.10: 1098230-1098519 | chr21:14, 358, 230-14, 358, 519 | GYGYGYGTTTAAYGG TTTTGTTAGGTTTAT | 38 | CATAATAATAACTTC TCAAACCCCAATCA |
| HSF2BP region A | NT_011515.11: 394974-395324 | chr21:43, 902, 066-43, 902, 416 | TAYGGAGTAGAGAAGAGA GTGATTATTTATTTAYGT | 40 | CRACAACRACCA TAAACRAAACRA |
| HSF2BP region B | NT_011515.11: 395238-395572 | chr21:43, 902, 330-43, 902, 664 | GTTTAAATAYGTTG GYGTYGGTTAGGGT | 42 | TTACATCAAAAACTAACT TTCCTTCTACTTTACAA |
| COL6A1 region A | NT_011515.11: 2740284-2740642 | chr21:46, 247, 376-46, 247, 734 | GTTYGGTYGGGAG GTTTTGTGATATT | 44 | AACTACRAAACRAAAT AAACAACCRTTAACATA |

TABLE 1-continued

Identity, location, primer sequences and PCR reaction conditions of the studied genomic sequences on chromosome 21. The respective regions on genomic contigs (accession number, version, start and end nucleotide numbers) deposited at GenBank of the National Center for Biotechnology Information and chromosomal locations (chromosome, start and end nucleotide numbers) on the Human May 2004 (hg17) assembly of the UCSC genome browser (available at genome.ucsc.edu web site) are shown in the second and third columns, respectively.

| | | | | | | |
|---|---|---|---|---|---|---|
| COL6A1 region B | NT_011515.11: 2740579-2740899 | chr21:46, 247, 671-46, 247, 991 | TYGGTTTATTGYGGT TGTATTATTAGGGTT | | 46 | TCCATAACATCGA CGACACTAACCAA |

| | | | PCR conditions | | | | |
|---|---|---|---|---|---|---|---|
| Sequence name | SEQ ID NO: | MgCl$_2$ (mM) | Primer (nM) | DMSO (%) | Betaine (M) | TaqGold (U) | Annealing temperature (° C.) |
| CGI137 region A | 7 | 2 | 200 | 0 | 0 | 1 | 62 |
| CGI137 region B | 9 | 3 | 200 | 0 | 0 | 1 | 60 |
| PDE9A region A | 11 | 3 | 200 | 0 | 0 | 1.25 | 60 |
| PDE9A region B | 13 | 3 | 400 | 0 | 0 | 0.625 | 55 |
| PDE9A region C | 15 | 3 | 200 | 0 | 0 | 1.25 | 60 |
| PPP1R2P2 region A | 17 | 3 | 300 | 0 | 0 | 1.25 | 62 |
| PPP1R2P2 region B | 19 | 3 | 100 | 0 | 0 | 1.25 | 60 |
| Similarity to Fem1A (*C. elegans*) region A | 21 | 4 | 100 | 0 | 0 | 1.25 | 65 |
| Similarity to Fem1A (*C. elegans*) region B | 23 | 4 | 100 | 0 | 0 | 1.25 | 65 |
| CGI009 | 25 | 3 | 200 | 0 | 0 | 1 | 60 |
| CBR1 | 27 | 1.5 | 400 | 0 | 0 | 1 | 60 |
| DSCAM | 29 | 3 | 200 | 0 | 0 | 1 | 60 |
| C21orf29 | 31 | 3 | 200 | 0 | 0 | 1 | 57 |
| CGI111 | 33 | 2 | 200 | 3 | 0 | 1.25 | 52 |
| CGI121 | 35 | 3 | 400 | 0 | 1 | 1.25 | 60 |
| KIAA0656 region A | 37 | 2 | 300 | 0 | 0 | 1.25 | 66 |
| KIAA0656 region B | 39 | 2 | 400 | 0 | 0 | 1.25 | 65 |
| HSF2BP region A | 41 | 3 | 400 | 5 | 0 | 1.25 | 55 |
| HSF2BP region B | 43 | 4 | 400 | 0 | 0 | 1.25 | 65 |
| COL6A1 region A | 45 | 3 | 600 | 0 | 0 | 1.25 | 60 |
| COL6A1 region B | 47 | 4 | 200 | 0 | 0 | 1.25 | 65 |

Data comparison and statistical analysis A CpG site was scored as methylated if the sequence was cytosine; scored as unmethylated if it was occupied by a thymine residue (deoxy counterpart of uracil). The proportion of methylated cytosine residue for each CpG site was determined among the placental tissues as well as the maternal blood samples. The distribution of methylated and unmethylated cytosines was compared between the placental tissues and maternal buffy coat for each CpG site by chi-square analysis. P-value of <0.05 is considered as statistically significantly different. Statistical analysis was performed using the Sigma Stat 3.0 software (SPSS).

Results and Discussion

Among the CpG-containing genomic sequences identified from the computational search, 13 loci were the focus of the present investigation. The names, chromosomal location and GenBank Accession numbers of these loci are listed in Table 1. For each of the studied loci, bisulfite sequencing was performed on placental tissues and maternal blood cells.

Figure 1B:
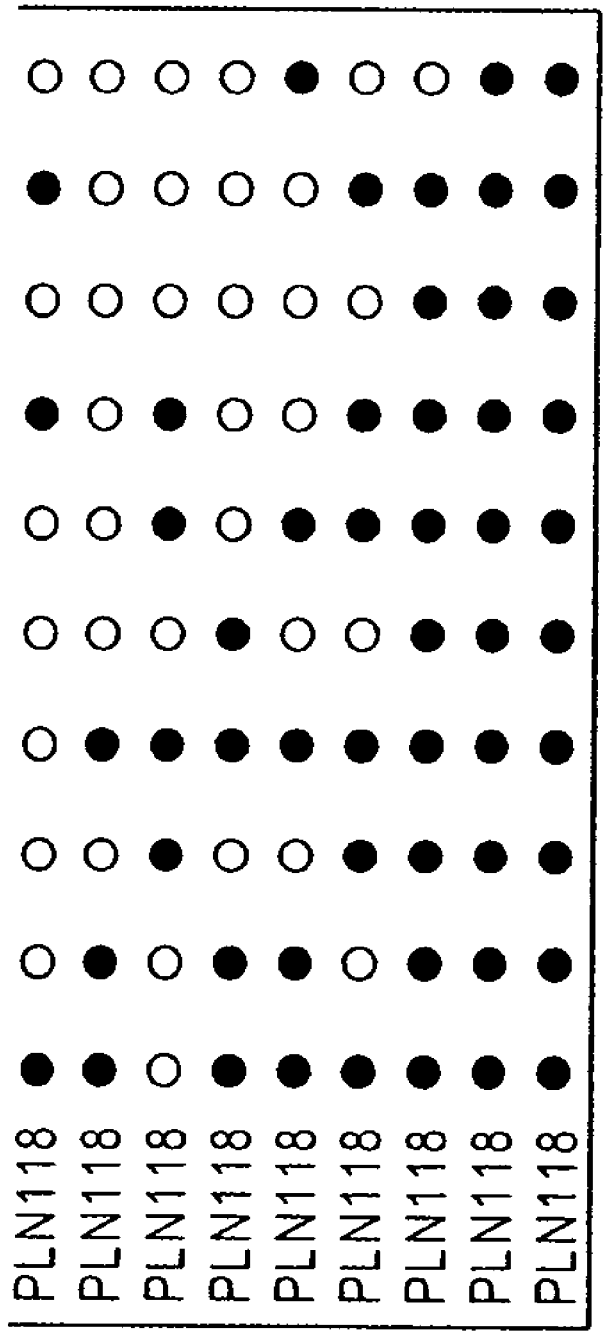
Figure 2B:
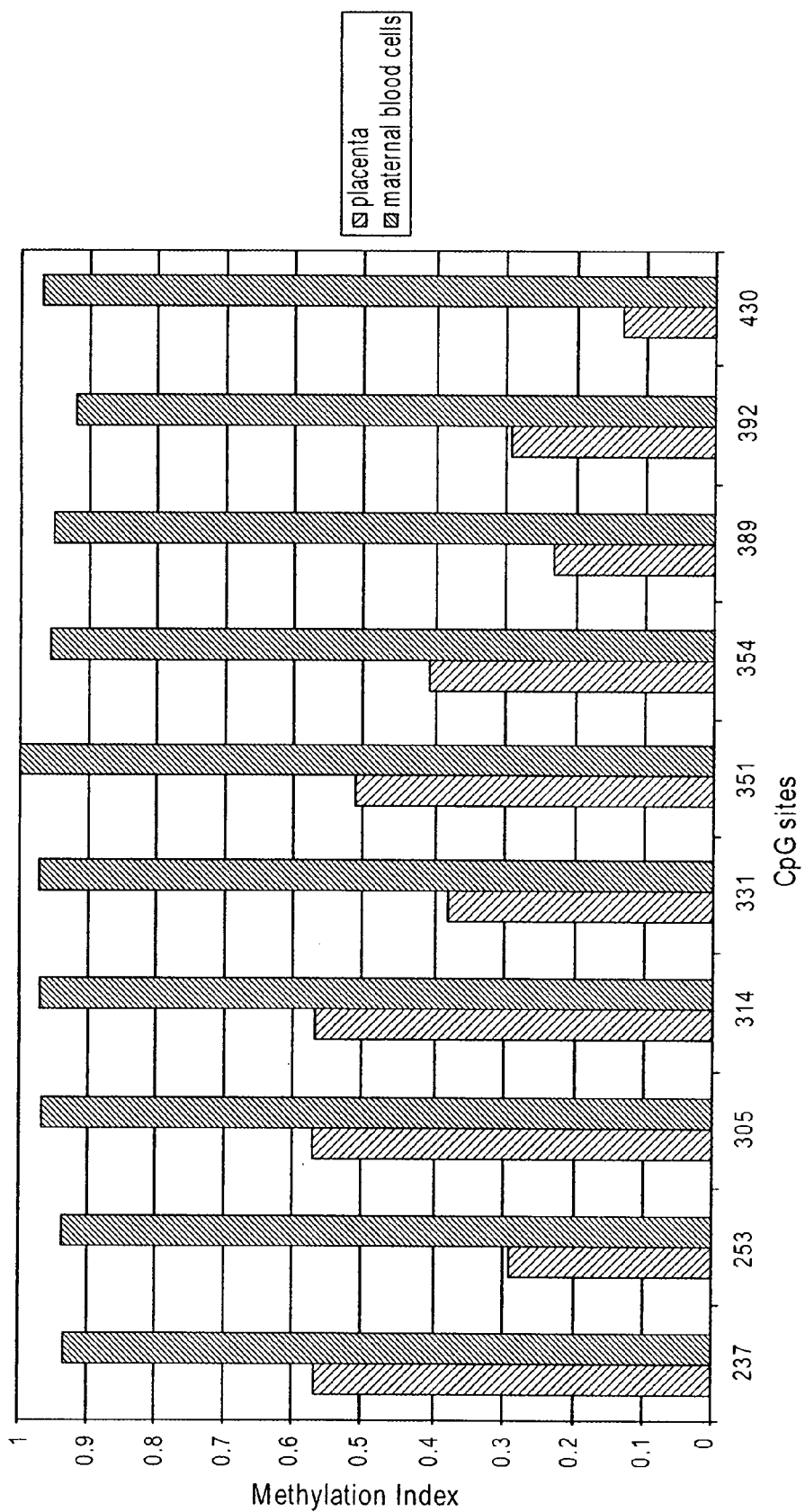
FIG. 2. Box plot of the methylation indices among all of the sequenced clones for the placenta and maternal blood cell samples for each of the studied CpG sites within CGI137 (A). region A and (B). region B. Across the x-axis, the individual CpG sites are designated with their nucleotide positions relative to chr21:46,249,636 (+1) of the Human May 2004 (hg17) assembly of the UCSC Genome Browser.

CGI137 The methylation profile of CGI137 was studied among placental tissues and the corresponding maternal blood cells collected from 5 third-trimester pregnancies. The bisulfite sequencing data for regions A and B of all the 5 cases are shown in FIGS. 1A and 1B, respectively. Each row in the respective panels represents the bisulfite sequencing result for one clone while each column represents an individual CpG dinucleotide within the genomic sequence. The proportion of methylated clones among all of the sequenced clones, the methylation index, at each CpG site was determined for all 5 placental tissue and maternal blood cell samples. The data are summarized in FIGS. 2A and 2B. It can be seen that the placenta is hypomethylated compared with maternal blood cells. Chi-square analysis was performed to compare the distribution of methylated and unmethylated clones between the placental tissues and maternal blood cells at each CpG site. The differences in the methylation indices between the placenta and maternal blood cells are statistically significant for all 21 CpG sites (Chi-square, P<0.0001, Tables 2A and 2B).

TABLE 2A

Summary of bisulfite sequencing data and chi-square analysis comparing the methylation profile of the placental tissues and maternal blood cells at the individual CpG sites within CGI137 Region A. The individual CpG sites are designated by their nucleotide positions relative to chr21: 46,249,636 (+1) of the Human May 2004 (hg17) assembly of the UCSC Genome Browser.

| Samples | Methylation status | Number of clones at designated CpG sites | | | | | |
|---|---|---|---|---|---|---|---|
| | | 430 | 439 | 442 | 472 | 477 | 481 |
| Third trimester placenta | Methylated | 6 | 13 | 9 | 39 | 45 | 27 |
| | Unmethylated | 66 | 59 | 63 | 33 | 27 | 45 |
| Third trimester maternal blood cells | Methylated | 71 | 71 | 68 | 73 | 73 | 74 |
| | Unmethylated | 3 | 3 | 6 | 1 | 1 | 0 |

| Samples | Methylation status | Number of clones at designated CpG sites | | | | |
|---|---|---|---|---|---|---|
| | | 486 | 513 | 541 | 563 | 561 |
| Third trimester placenta | Methylated | 18 | 17 | 17 | 33 | 27 |
| | Unmethylated | 54 | 55 | 55 | 39 | 45 |
| Third trimester maternal blood cells | Methylated | 73 | 69 | 65 | 72 | 73 |
| | Unmethylated | 1 | 5 | 6 | 2 | 1 |

| Comparison | | Chi-square and p-values at designated CpG sites | | | | | |
|---|---|---|---|---|---|---|---|
| | | 430 | 439 | 442 | 472 | 477 | 481 |
| Third trimester placenta vs. Third trimester maternal blood cells | Chi-square p-values | 108.9 <0.0001 | 87.458 <0.0001 | 89.127 <0.0001 | 37.968 <0.0001 | 28.477 <0.0001 | 53.957 <0.0001 |

| Comparison | | Chi-square and p-values at designated CpG sites | | | | |
|---|---|---|---|---|---|---|
| | | 486 | 513 | 541 | 563 | 561 |
| Third trimester placenta vs. Third trimester maternal blood cells | Chi-square p-values | 81.195 <0.0001 | 70.247 <0.0001 | 67.167 <0.0001 | 45.343 <0.0001 | 60.43 <0.0001 |

TABLE 2B

Summary of bisulfite sequencing data and chi-square analysis comparing the methylation profile of the placental tissues and maternal blood cells at the individual CpG sites within CGI137 Region B. The individual CpG sites are designated by their nucleotide positions relative to chr21: 46,249,636 (+1) of the Human May 2004 (hg17) assembly of the UCSC Genome Browser.

| Samples | Methylation status | Number of clones at designated CpG sites | | | | |
|---|---|---|---|---|---|---|
| | | 237 | 253 | 305 | 314 | 331 |
| Third trimester placenta | Methylated | 39 | 20 | 39 | 39 | 25 |
| | Unmethylated | 29 | 48 | 29 | 29 | 42 |
| Third trimester maternal blood cell | Methylated | 55 | 55 | 57 | 57 | 57 |
| | Unmethylated | 4 | 4 | 2 | 2 | 2 |

| Samples | Methylation status | Number of clones at designated CpG sites | | | | |
|---|---|---|---|---|---|---|
| | | 351 | 354 | 389 | 392 | 430 |
| Third trimester placenta | Methylated | 35 | 28 | 16 | 20 | 9 |
| | Unmethylated | 33 | 40 | 52 | 48 | 59 |
| Third trimester maternal blood cell | Methylated | 59 | 56 | 56 | 54 | 57 |
| | Unmethylated | 0 | 3 | 3 | 5 | 2 |

| Comparison | | Chi-square and p-values at designated CpG sites | | | | |
|---|---|---|---|---|---|---|
| | | 237 | 253 | 305 | 314 | 331 |
| Third trimester placenta vs. Third trimester maternal blood cells | Chi-square p-values | 19.307 <0.0001 | 50.587 <0.0001 | 24.301 <0.0001 | 24.301 <0.0001 | 45 <0.0001 |

| Comparison | | Chi-square and p-values at designated CpG sites | | | | |
|---|---|---|---|---|---|---|
| | | 351 | 354 | 389 | 392 | 430 |
| Third trimester placenta vs. | Chi-square | 37.995 | 38.373 | 62.693 | 49.794 | 84.667 |

TABLE 2B-continued

Summary of bisulfite sequencing data and chi-square analysis comparing the methylation profile of the placental tissues and maternal blood cells at the individual CpG sites within CGI137 Region B. The individual CpG sites are designated by their nucleotide positions relative to chr21: 46,249,636 (+1) of the Human May 2004 (hg17) assembly of the UCSC Genome Browser.

| | | | | | | |
|---|---|---|---|---|---|---|
| Third trimester maternal blood cells | p-values | <0.0001 | <0.0001 | <0.0001 | <0.0001 | <0.0001 |

Figure 3A:
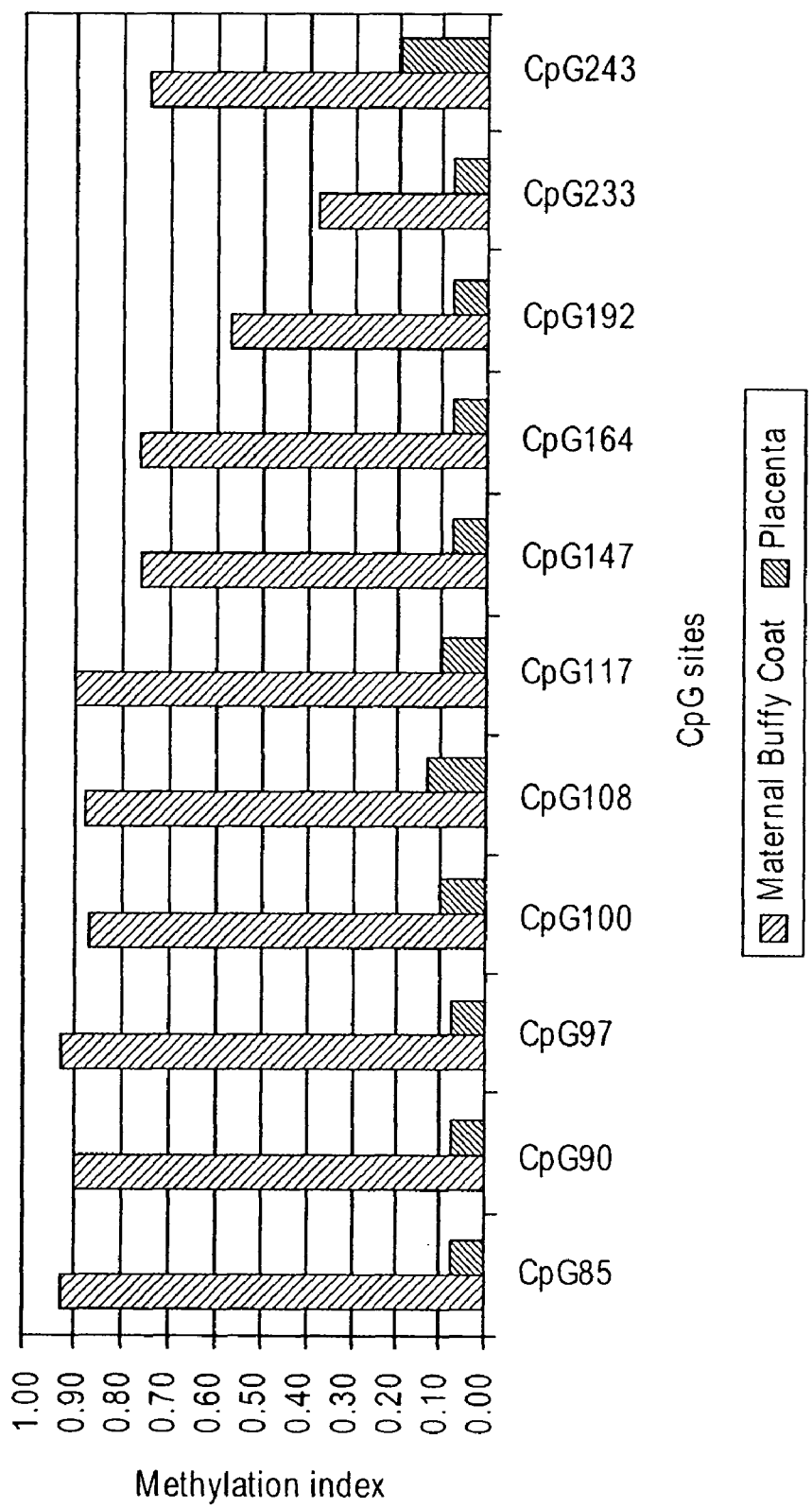
FIG. 3. Box plot of the methylation indices among all of the sequenced clones for the placenta and maternal blood cell samples for each of the studied CpG sites within PDE9A among third-trimester and first-trimester pregnancies for region A (A and B), region B (C and D) and region C (E). For FIGS. 3A and 3B, across the x-axis, the individual CpG sites are designated with their nucleotide positions relative to the reverse strand of chr21: 42,978,424 (+1) of the Human May 2004 (hg17) assembly of the UCSC Genome Browser; and for FIGS. 3C and 3D, relative to the forward strand of chr21: 42,978,718 (+1); for FIG. 3E, relative to the forward strand of chr21:42,978,005 (+1).
Figure 3B:
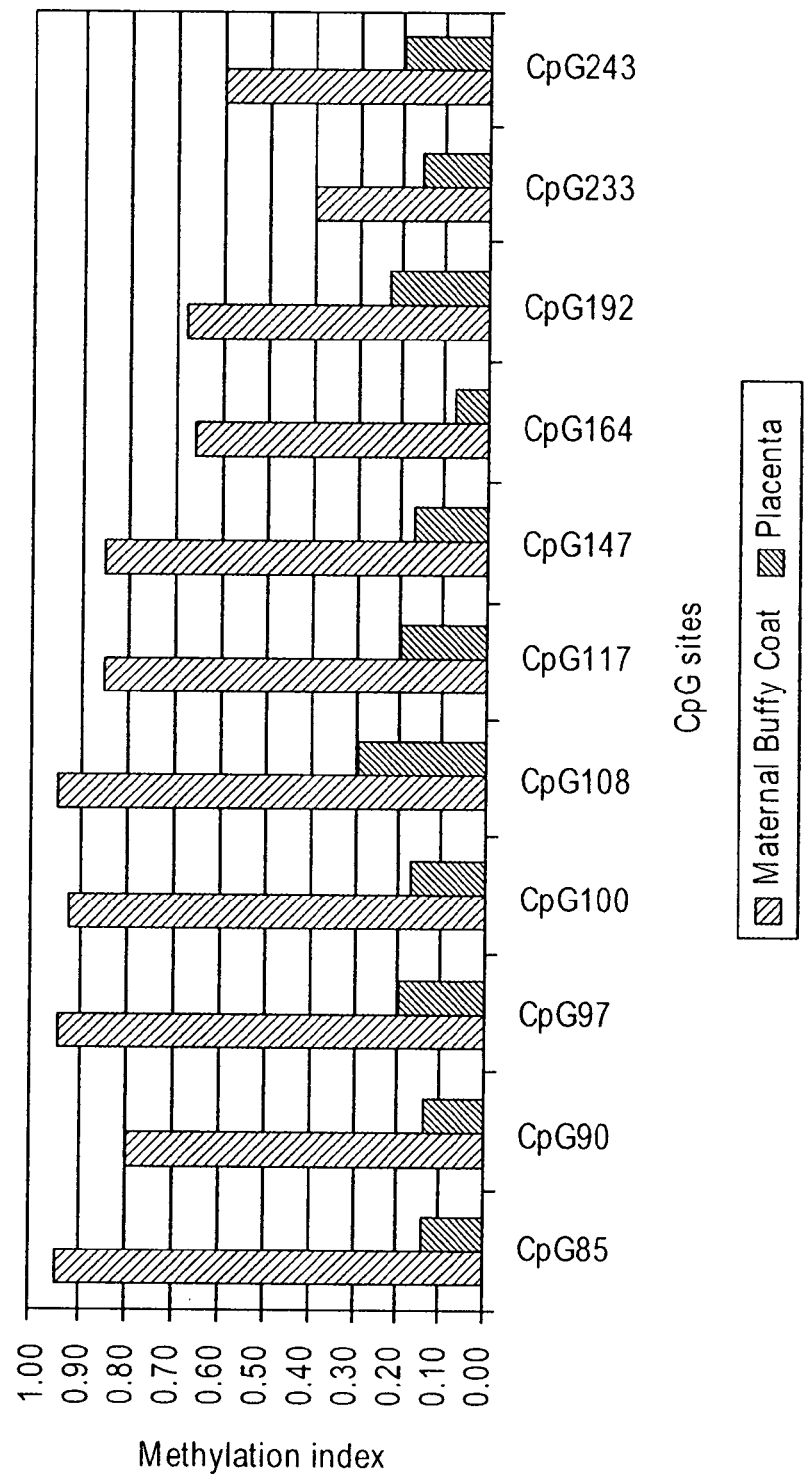
Figure 3C:
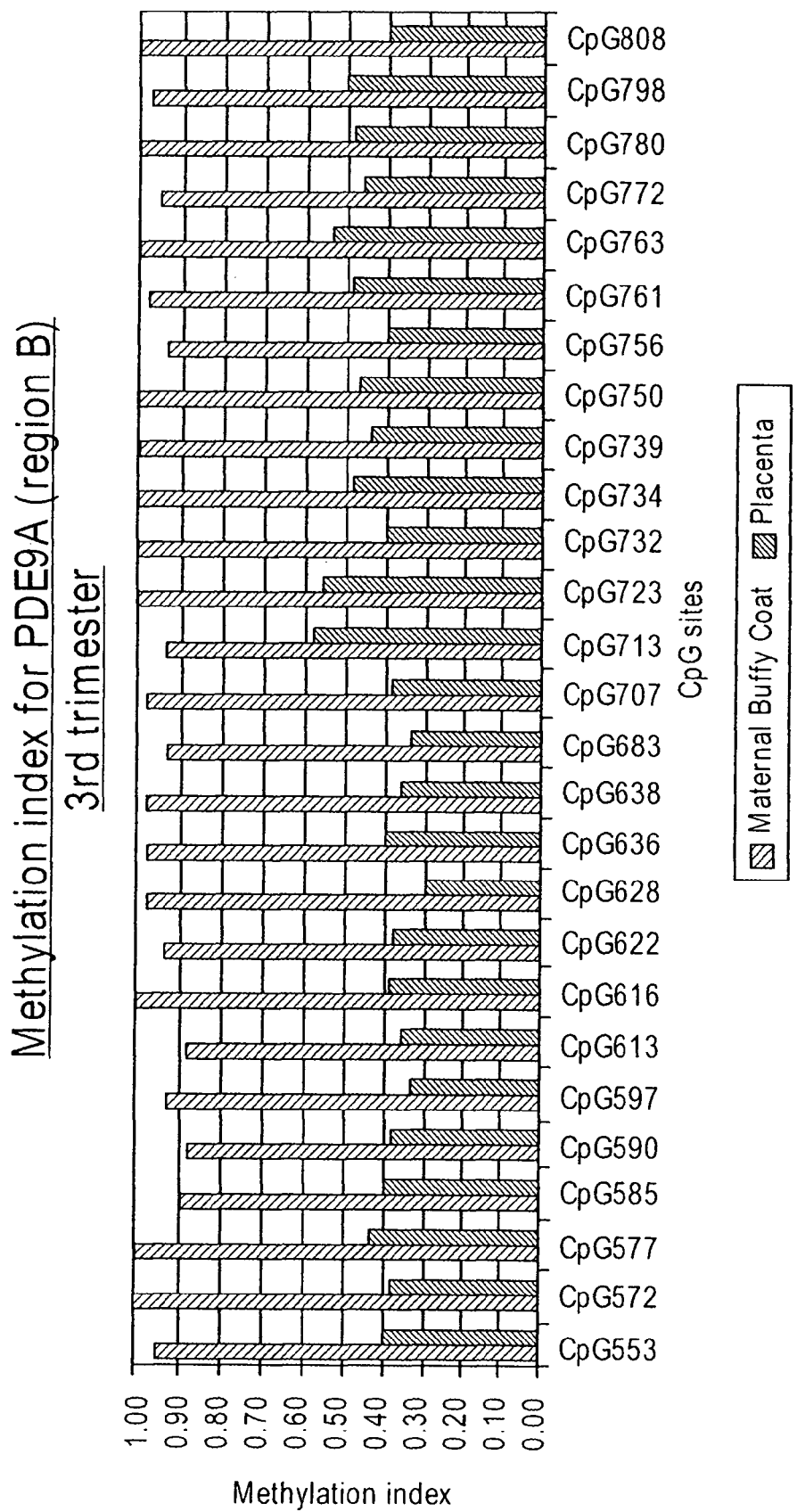
Figure 3D:
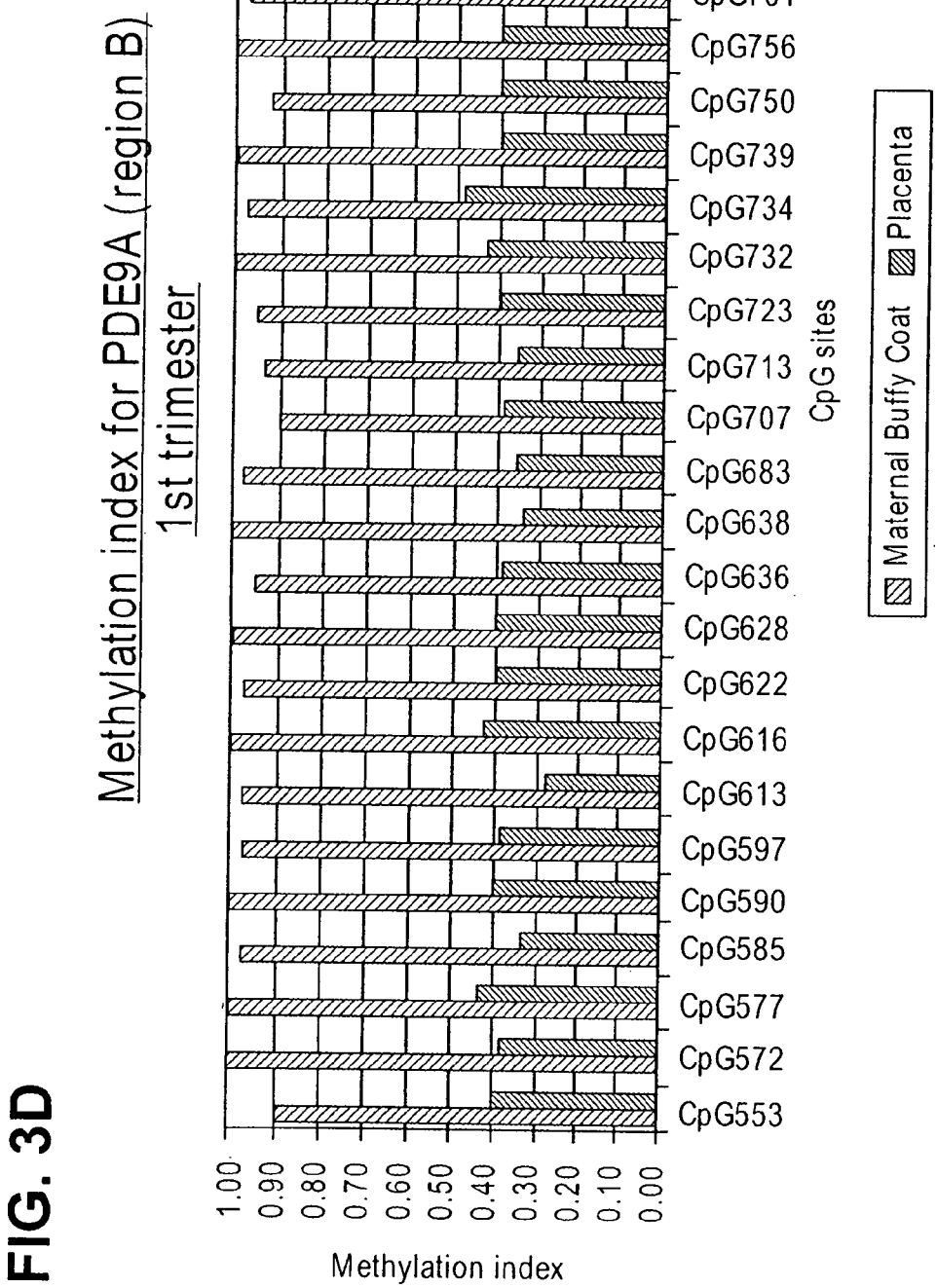

Phosphodiesterase 9A (PDE9A) The methylation profile of PDE9A was studied among placental tissues and the corresponding maternal blood cells collected from 5 third-trimester and 5 first-trimester pregnancies. Cloning and bisulfite sequencing were performed and the methylation indices of the studied CpG sites in the placental tissues and maternal blood cells for the region A amplicon are summarized in FIGS. 3A and 3B. The corresponding data for region B are summarized in FIGS. 3C and 3D. Comparisons between third-trimester placental tissues and maternal blood cells for region C are shown in FIG. 3E. In general, the placenta is hypomethylated when compared to maternal blood cells. Chi-square analysis was performed as described above to assess for statistically significant differences between the two tissues. All but CpG2250 in the third-trimester comparison are statistically significantly different in both the first-and third-trimester pregnancies (Chi-square analysis, Tables 3A to E).

TABLE 3A

Summary of bisulfite sequencing data, methylation indices and chi-square analysis comparing the methylation profile of third-trimester placental tissues and maternal blood cells at the individual CpG sites within PDE9A region A. The individual CpG sites are designated by their nucleotide positions relative to the reverse strand of chr21: 42,978,424 (+1) of the Human May 2004 (hg17) assembly of the UCSC Genome Browser.

| | | CpG85 | CpG90 | CpG97 | CpG100 | CpG108 | CpG117 | CpG147 | CpG164 | CpG192 | CpG233 | CpG243 |
|---|---|---|---|---|---|---|---|---|---|---|---|---|
| Maternal Buffy Coat | C | 37 | 36 | 37 | 35 | 35 | 36 | 30 | 30 | 23 | 15 | 29 |
| | T | 3 | 4 | 3 | 5 | 5 | 4 | 10 | 10 | 17 | 25 | 11 |
| | MethIndx | 0.93 | 0.90 | 0.93 | 0.88 | 0.88 | 0.90 | 0.75 | 0.75 | 0.58 | 0.3 | 0.73 |
| | C + T | 40 | 40 | 40 | 40 | 40 | 40 | 40 | 40 | 40 | 40 | 40 |
| Placenta | C | 3 | 3 | 3 | 4 | 5 | 4 | 3 | 3 | 3 | 3 | 8 |
| | T | 37 | 37 | 37 | 36 | 35 | 36 | 37 | 37 | 37 | 37 | 32 |
| | MethIndx | 0.08 | 0.08 | 0.08 | 0.10 | 0.13 | 0.10 | 0.08 | 0.08 | 0.08 | 0.08 | 0.20 |
| | C + T | 40 | 40 | 40 | 40 | 40 | 40 | 40 | 40 | 40 | 40 | 40 |
| | chi-square | 54.450 | 51.232 | 54.450 | 45.028 | 42.050 | 48.050 | 34.868 | 34.868 | 20.570 | 8.674 | 20.113 |
| | p-value | =<0.001 | =<0.001 | =<0.001 | =<0.001 | =<0.001 | =<0.001 | =<0.001 | =<0.001 | =<0.001 | 0.003 | =<0.001 |

TABLE 3B

Summary of bisulfite sequencing data, methylation indices and chi-square analysis comparing the methylation profile of first-trimester placental tissues and maternal blood cells at the individual CpG sites within PDE9A region A. The individual CpG sites are designated by their nucleotide positions relative to the reverse strand of chr21: 42,978,424 (+1) of the Human May 2004 (hg17) assembly of the UCSC Genome Browser.

| | | CpG85 | CpG90 | CpG97 | CpG100 | CpG108 | CpG117 | CpG147 | CpG164 | CpG192 | CpG233 | CpG243 |
|---|---|---|---|---|---|---|---|---|---|---|---|---|
| Maternal Buffy Coat | C | 38 | 32 | 38 | 37 | 38 | 34 | 34 | 26 | 27 | 16 | 24 |
| | T | 2 | 8 | 2 | 3 | 2 | 6 | 6 | 14 | 13 | 24 | 16 |
| | MethIndx | 0.95 | 0.80 | 0.95 | 0.93 | 0.95 | 0.85 | 0.85 | 0.65 | 0.68 | 0.40 | 0.60 |
| | C + T | 40 | 40 | 40 | 40 | 40 | 40 | 40 | 40 | 40 | 40 | 40 |
| Placenta | C | 6 | 6 | 8 | 7 | 12 | 8 | 7 | 3 | 9 | 6 | 8 |
| | T | 34 | 34 | 32 | 33 | 28 | 32 | 33 | 37 | 31 | 34 | 32 |
| | MethIndx | 0.15 | 0.15 | 0.20 | 0.18 | 0.30 | 0.20 | 0.18 | 0.08 | 0.23 | 0.15 | 0.20 |
| | C + T | 40 | 40 | 40 | 40 | 40 | 40 | 40 | 40 | 40 | 40 | 40 |
| | chi-square | 48.535 | 31.328 | 43.018 | 42.475 | 33.333 | 31.328 | 33.821 | 26.180 | 14.596 | 5.078 | 11.719 |
| | p-value | =<0.001 | =<0.001 | =<0.001 | =<0.001 | =<0.001 | =<0.001 | =<0.001 | =<0.001 | =<0.001 | 0.024 | =<0.001 |

TABLE 3C

Summary of bisulfite sequencing data, methylation indices and chi-square analysis comparing the methylation profile of third-trimester placental tissues and maternal blood cells at the individual CpG sites within PDE9A region B. The individual CpG sites are designated by their nucleotide positions relative to chr21: 42,978,718 (+1) of the Human May 2004 (hg17) assembly of the UCSC Genome Browser.

| | | CpG553 | CpG572 | CpG577 | CpG585 | CpG590 | CpG597 | CpG613 | CpG616 | CpG622 | CpG628 | CpG636 |
|---|---|---|---|---|---|---|---|---|---|---|---|---|
| Maternal Buffy Coat | C | 38 | 40 | 40 | 36 | 35 | 37 | 35 | 40 | 37 | 39 | 39 |
| | T | 2 | 0 | 0 | 4 | 5 | 3 | 5 | 0 | 3 | 1 | 1 |
| | MethIndx | 0.95 | 1.00 | 1.00 | 0.90 | 0.88 | 0.93 | 0.88 | 1.00 | 0.93 | 0.98 | 0.98 |
| | C + T | 40 | 40 | 40 | 40 | 40 | 40 | 40 | 40 | 40 | 40 | 40 |

TABLE 3C-continued

Summary of bisulfite sequencing data, methylation indices and chi-square analysis comparing the methylation profile of third-trimester placental tissues and maternal blood cells at the individual CpG sites within PDE9A region B. The individual CpG sites are designated by their nucleotide positions relative to chr21: 42,978,718 (+1) of the Human May 2004 (hg17) assembly of the UCSC Genome Browser.

|  |  |  |  |  |  |  |  |  |  |  |  |
|---|---|---|---|---|---|---|---|---|---|---|---|
| Placenta | C | 16 | 15 | 17 | 16 | 15 | 13 | 14 | 15 | 15 | 12 | 16 |
|  | T | 24 | 25 | 23 | 24 | 25 | 27 | 26 | 25 | 25 | 28 | 24 |
|  | MethIndx | 0.40 | 0.38 | 0.43 | 0.40 | 0.38 | 0.33 | 0.35 | 0.38 | 0.38 | 0.30 | 0.40 |
|  | C + T | 40 | 40 | 40 | 40 | 40 | 40 | 40 | 40 | 40 | 40 | 40 |
|  | chi-square | 25.128 | 33.513 | 29.535 | 19.835 | 19.253 | 28.213 | 21.066 | 33.513 | 24.231 | 36.565 | 28.16 |
|  | p-value | =<0.001 | =<0.001 | =<0.001 | =<0.001 | =<0.001 | =<0.001 | =<0.001 | =<0.0014 | =<0.001 | =<0.001 | =<0.001 |

|  |  | CpG638 | CpG683 | CpG707 | CpG713 | CpG723 | CpG732 | CpG734 | CpG739 | CpG750 | CpG756 |
|---|---|---|---|---|---|---|---|---|---|---|---|
| Maternal | C | 39 | 37 | 39 | 37 | 40 | 40 | 40 | 40 | 40 | 37 |
| Buffy | T | 1 | 3 | 1 | 3 | 0 | 0 | 0 | 0 | 0 | 3 |
| Coat | MethIndx | 0.98 | 0.93 | 0.98 | 0.93 | 1.00 | 1.00 | 1.00 | 1.00 | 1.00 | 0.93 |
|  | C + T | 40 | 40 | 40 | 40 | 40 | 40 | 40 | 40 | 40 | 40 |
| Placenta | C | 14 | 13 | 15 | 23 | 22 | 16 | 19 | 17 | 18 | 16 |
|  | T | 26 | 27 | 25 | 17 | 18 | 24 | 21 | 23 | 22 | 24 |
|  | MethIndx | 0.35 | 0.33 | 0.38 | 0.58 | 0.55 | 0.40 | 0.48 | 0.43 | 0.45 | 0.40 |
|  | C + T | 40 | 40 | 40 | 40 | 40 | 40 | 40 | 40 | 40 | 40 |
|  | chi-square | 32.201 | 28.213 | 30.142 | 11.267 | 20.717 | 31.488 | 25.827 | 29.535 | 27.649 | 22.362 |
|  | p-value | =<0.001 | =<0.001 | =<0.001 | =<0.001 | =<0.001 | =<0.001 | =<0.001 | =<0.001 | =<0.001 | =<0.001 |

|  |  | CpG761 | CpG763 | CpG772 | CpG780 | CpG798 | CpG808 | CpG820 | CpG828 |
|---|---|---|---|---|---|---|---|---|---|
| Maternal | C | 39 | 40 | 38 | 40 | 39 | 40 | 38 | 2 |
| Buffy | T | 1 | 0 | 2 | 0 | 1 | 0 | 2 | 38 |
| Coat | MethIndx | 0.98 | 1.00 | 0.95 | 1.00 | 0.98 | 1.00 | 0.95 | 0.05 |
|  | C + T | 40 | 40 | 40 | 40 | 40 | 40 | 40 | 40 |
| Placenta | C | 19 | 21 | 18 | 19 | 20 | 16 | 14 | 2 |
|  | T | 21 | 19 | 22 | 21 | 20 | 24 | 26 | 38 |
|  | MethIndx | 0.48 | 0.53 | 0.45 | 0.48 | 0.50 | 0.40 | 0.35 | 0.05 |
|  | C + T | 40 | 40 | 40 | 40 | 40 | 40 | 40 | 40 |
|  | chi-square | 22.633 | 22.364 | 21.488 | 25.827 | 20.92 | 31.488 | 29.066 | 0.263 |
|  | p-value | =<0.001 | =<0.001 | =<0.001 | =<0.001 | =<0.001 | =<0.001 | =<0.001 | 0.608 |

TABLE 3D

Summary of bisulfite sequencing data, methylation indices and chi-square analysis comparing the methylation profile of first-trimester placental tissues and maternal blood cells at the individual CpG sites within PDE9A region B. The individual CpG sites are designated by their nucleotide positions relative to chr21: 42,978,718 (+1) of the Human May 2004 (hg17) assembly of the UCSC Genome Browser.

|  |  | CpG553 | CpG572 | CpG577 | CpG585 | CpG590 | CpG597 | CpG613 | CpG616 | CpG622 | CpG628 |
|---|---|---|---|---|---|---|---|---|---|---|---|
| Maternal | C | 36 | 40 | 40 | 39 | 40 | 39 | 39 | 40 | 39 | 40 |
| Buffy | T | 4 | 0 | 0 | 1 | 0 | 1 | 1 | 0 | 1 | 0 |
| Coat | MethIndx | 0.90 | 1.00 | 1.00 | 0.98 | 1.00 | 0.98 | 0.98 | 1.00 | 0.98 | 1.00 |
|  | C + T | 40 | 40 | 40 | 40 | 40 | 40 | 40 | 40 | 40 | 40 |
| Placenta | C | 16 | 16 | 17 | 13 | 16 | 15 | 11 | 17 | 16 | 16 |
|  | T | 24 | 24 | 23 | 27 | 24 | 25 | 29 | 23 | 24 | 24 |
|  | MethIndx | 0.40 | 0.40 | 0.43 | 0.33 | 0.40 | 0.38 | 0.28 | 0.43 | 0.40 | 0.40 |
|  | C + T | 40 | 40 | 40 | 40 | 40 | 40 | 40 | 40 | 40 | 40 |
|  | Chi-Square | 19.835 | 31.488 | 29.535 | 34.341 | 31.488 | 30.142 | 38.88 | 29.535 | 28.16 | 31.488 |
|  | p-value | =<0.001 | =<0.001 | =<0.001 | =<0.001 | =<0.001 | =<0.001 | =<0.001 | =<0.001 | =<0.001 | =<0.001 |

|  |  | CpG636 | CpG638 | CpG683 | CpG707 | CpG713 | CpG723 | CpG732 | CpG734 | CpG739 |
|---|---|---|---|---|---|---|---|---|---|---|
| Maternal | C | 38 | 40 | 39 | 36 | 37 | 38 | 40 | 39 | 40 |
| Buffy | T | 2 | 0 | 1 | 4 | 3 | 2 | 0 | 1 | 0 |
| Coat | MethIndx | 0.95 | 1.00 | 0.98 | 0.90 | 0.93 | 0.95 | 1.00 | 0.98 | 1.00 |
|  | C + T | 40 | 40 | 40 | 40 | 40 | 40 | 40 | 40 | 40 |
| Placenta | C | 15 | 13 | 14 | 15 | 14 | 16 | 17 | 16 | 16 |
|  | T | 25 | 27 | 26 | 25 | 26 | 24 | 23 | 24 | 24 |
|  | MethIndx | 0.38 | 0.33 | 0.35 | 0.38 | 0.35 | 0.40 | 0.43 | 0.40 | 0.40 |
|  | C + T | 40 | 40 | 40 | 40 | 40 | 40 | 40 | 40 | 40 |
|  | Chi-Square | 27.058 | 37.792 | 32.201 | 21.636 | 26.18 | 25.128 | 29.535 | 28.16 | 31.488 |
|  | p-value | =<0.001 | =<0.001 | =<0.001 | =<0.001 | =<0.001 | =<0.001 | =<0.001 | =<0.001 | =<0.001 |

|  |  | CpG750 | CpG756 | CpG761 | CpG763 | CpG772 | CpG780 | CpG798 | CpG808 |
|---|---|---|---|---|---|---|---|---|---|
| Maternal | C | 37 | 40 | 39 | 40 | 40 | 38 | 38 | 39 |
| Buffy | T | 3 | 0 | 1 | 0 | 0 | 2 | 2 | 1 |
| Coat | MethIndx | 0.93 | 1.00 | 0.98 | 1.00 | 1.00 | 0.95 | 0.95 | 0.98 |
|  | C + T | 40 | 40 | 40 | 40 | 40 | 40 | 40 | 40 |

TABLE 3D-continued

Summary of bisulfite sequencing data, methylation indices and chi-square analysis comparing the methylation profile of first-trimester placental tissues and maternal blood cells at the individual CpG sites within PDE9A region B. The individual CpG sites are designated by their nucleotide positions relative to chr21: 42,978,718 (+1) of the Human May 2004 (hg17) assembly of the UCSC Genome Browser.

| | | | | | | | | | |
|---|---|---|---|---|---|---|---|---|---|
| Placenta | C | 16 | 16 | 13 | 17 | 17 | 18 | 16 | 15 |
| | T | 24 | 24 | 27 | 23 | 23 | 22 | 24 | 25 |
| | MethIndx | 0.40 | 0.40 | 0.33 | 0.43 | 0.43 | 0.45 | 0.40 | 0.38 |
| | C + T | 40 | 40 | 40 | 40 | 40 | 40 | 40 | 40 |
| | Chi-Square | 22.362 | 31.488 | 34.341 | 29.535 | 29.535 | 21.488 | 25.128 | 30.142 |
| | p-value | =<0.001 | =<0.001 | =<0.001 | =<0.001 | =<0.001 | =<0.001 | =<0.001 | =<0.001 |

TABLE 3E

Summary of bisulfite sequencing data, methylation indices and chi-square analysis comparing the methylation profile of third-trimester placental tissues and maternal blood cells at the individual CpG sites within PDE9A region C. The individual CpG sites are designated by their nucleotide positions relative to chr21: 42,978,005 (+1) of the Human May 2004 (hg17) assembly of the UCSC Genome Browser.

| | | CpG2150 | CpG2200 | CpG2250 | CpG2344 | CpG2408 | CpG2440 |
|---|---|---|---|---|---|---|---|
| Maternal | C | 36 | 39 | 34 | 39 | 37 | 39 |
| Buffy | T | 4 | 1 | 6 | 1 | 3 | 1 |
| Coat | MethIndx | 0.90 | 0.98 | 0.85 | 0.98 | 0.93 | 0.98 |
| | C + T | 40 | 40 | 40 | 40 | 40 | 40 |
| Placenta | C | 32 | 26 | 28 | 22 | 20 | 27 |
| | T | 8 | 14 | 12 | 18 | 20 | 13 |
| | MethIndx | 0.80 | 0.65 | 0.70 | 0.55 | 0.50 | 0.68 |
| | C + T | 40 | 40 | 40 | 40 | 40 | 40 |
| | chi-square | 0.882 | 11.815 | 1.792 | 17.670 | 15.622 | 10.476 |
| | p-value | 0.348 | =<0.001 | 0.181 | =<0.001 | =<0.001 | 0.001 |

Figure 4A:
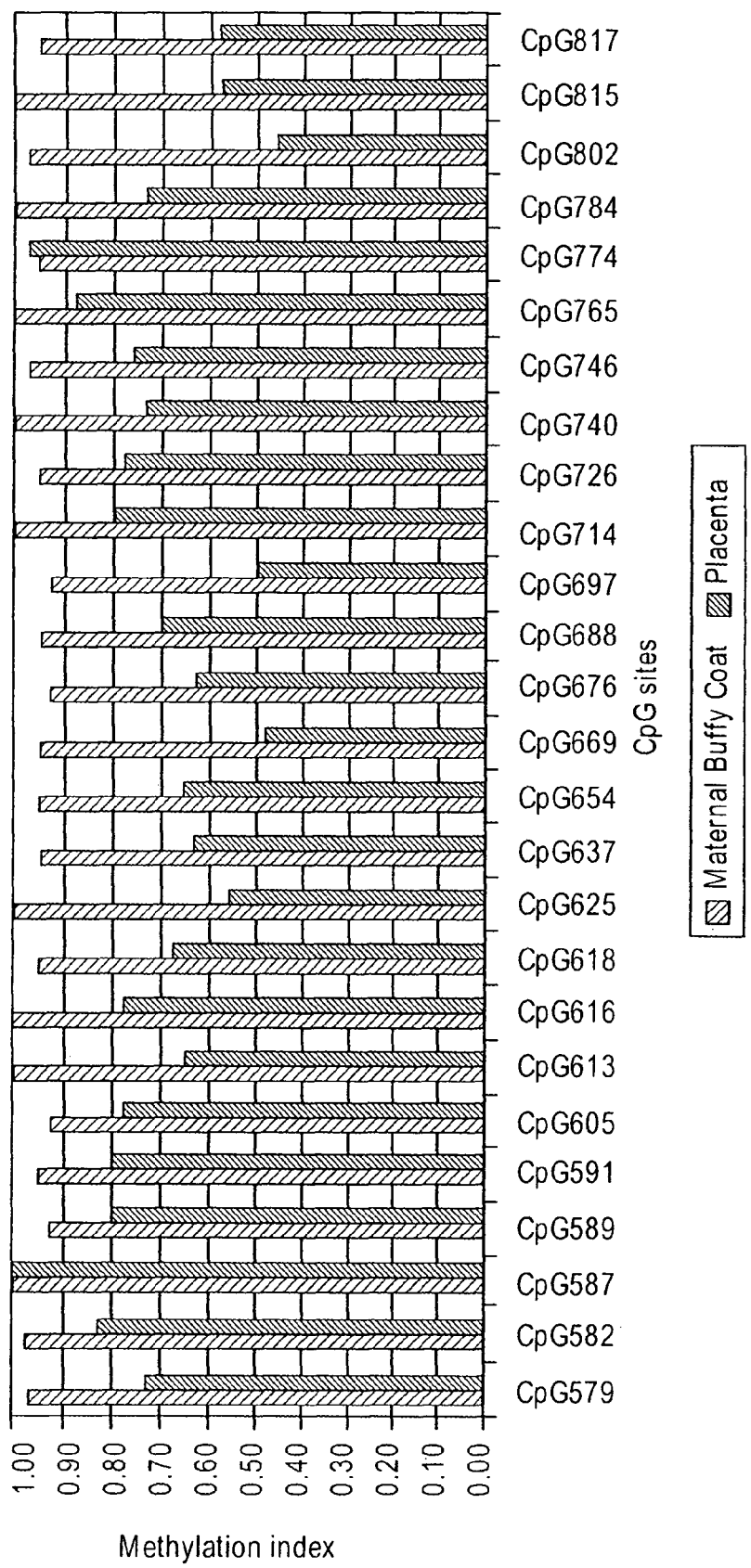
FIG. 4. Box plot of the methylation indices among all of the sequenced clones for the placenta and maternal blood cell samples for each of the studied CpG sites within region A of PPP1R2P2 among (A). third-trimester and (B). first-trimester pregnancies, and (C), within region B of PPP1R2P2 among third-trimester pregnancies. Across the x-axis, the individual CpG sites are designated with their nucleotide positions relative to chr21:36,180,493 (+1) of the Human May 2004 (hg17) assembly of the UCSC Genome Browser.
Figure 4B:
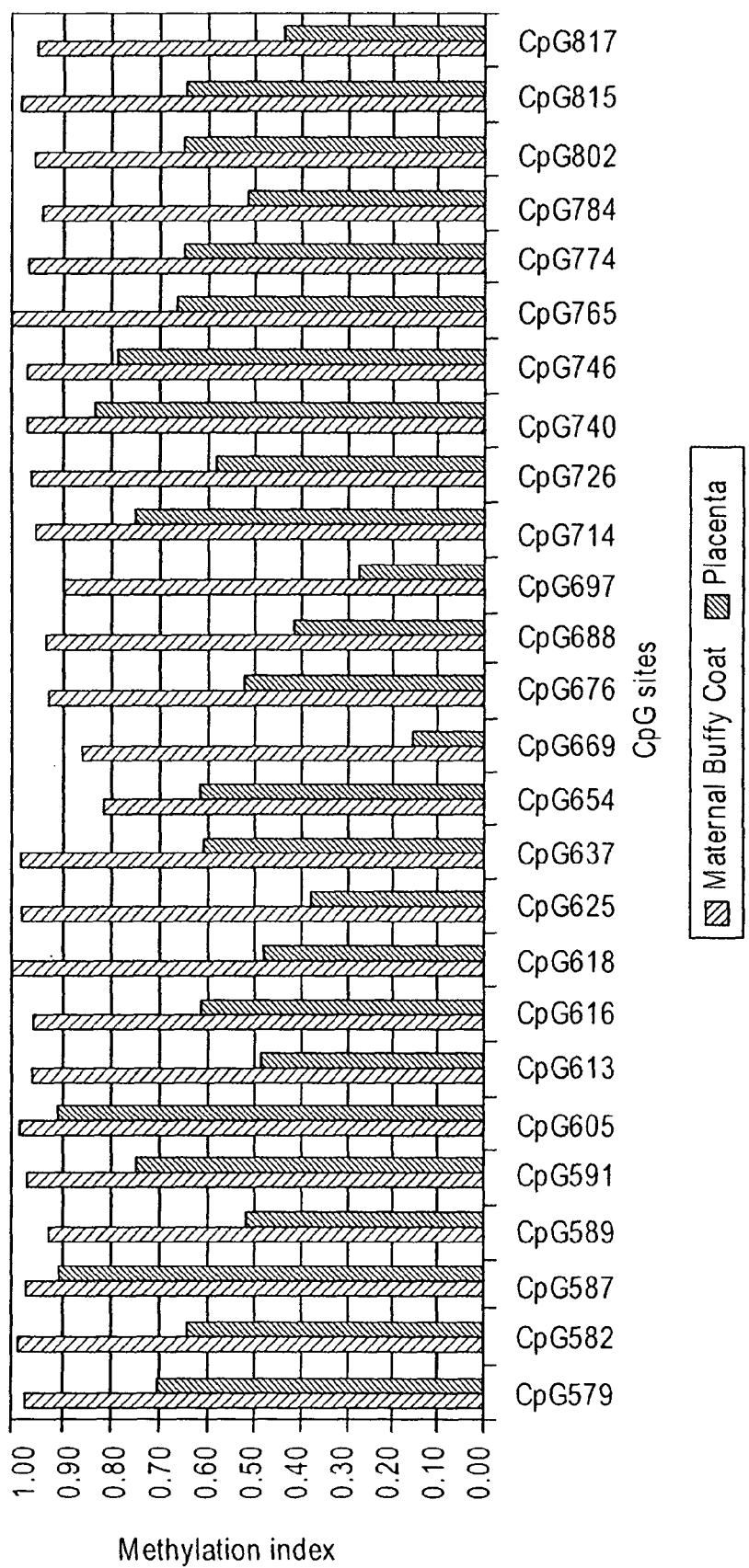
Figure 4C:
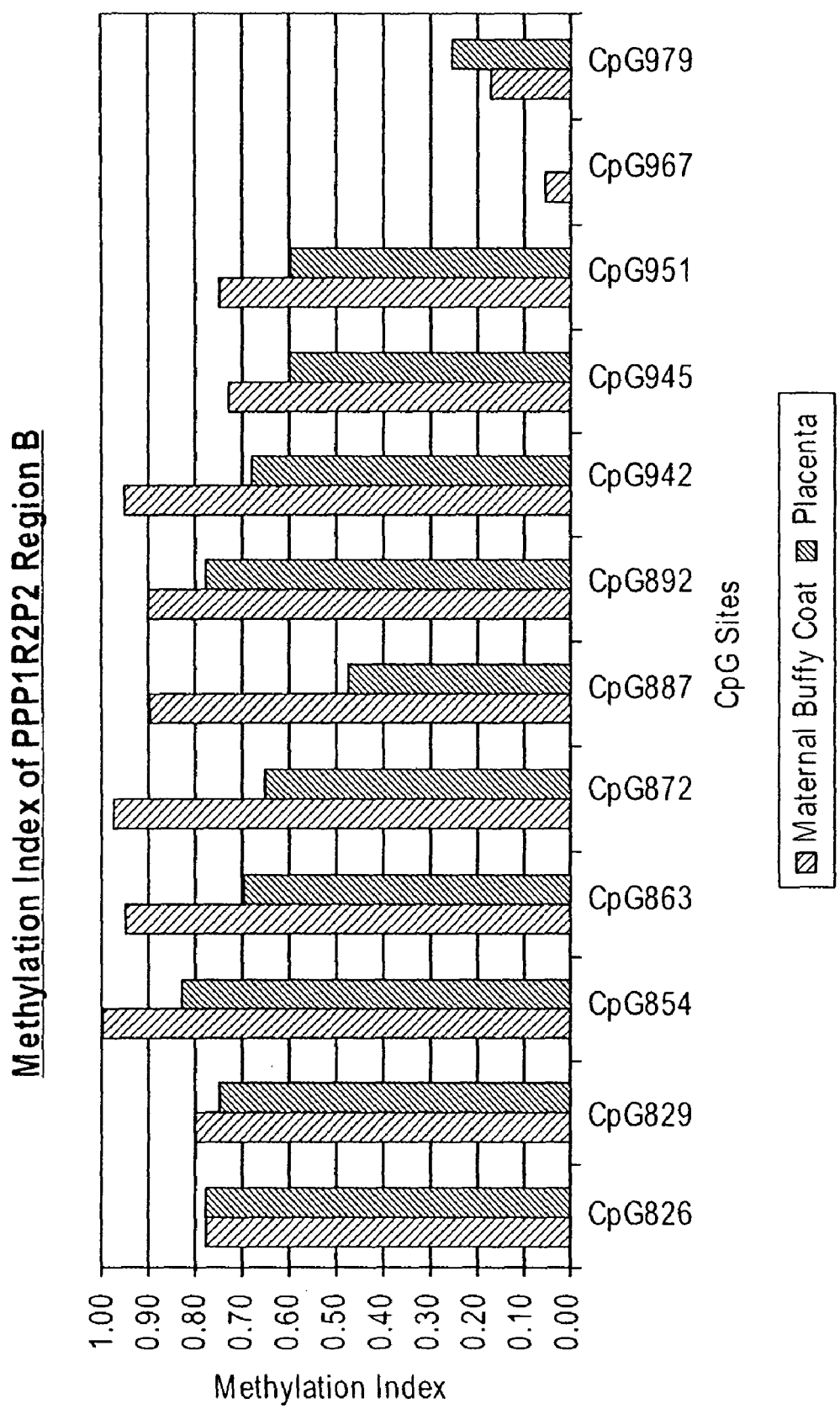

Homo sapiens protein phosphatase 1, regulatory (inhibitor) subunit 2pseudogene 2 (PPP1R2P2) The methylation profile of PPP1R2P2 region A was studied among placental tissues and the corresponding maternal blood cells collected from 5 third-trimester and 5 first-trimester pregnancies. Cloning and bisulfite sequencing were performed and the methylation indices of the studied CpG sites for region A in the placental tissues and maternal blood cells are summarized in FIGS. 4A and 4B. In general, the placenta is hypomethylated when compared to maternal blood cells. Chi-square analysis was performed as described above to assess for statistically significant differences between the two tissues. Among the studied CpG sites, 23 are statistically significantly different in the third-trimester pregnancies and 23 are statistically significantly different in the first-trimester pregnancies (Chi-square analysis, Tables 4A and 4B). In addition, the methylation profile of the CpG sites in PPP1R2P2 region B were also analysed by cloning and bisulfite sequencing in placental tissues and the corresponding maternal blood cells collected from 5 third-trimester pregnancies. For most CpG sites in region B, the placental tissue is hypomethylated compared to the maternal blood cells. The methylation indices in region B are summarized in FIG. 4C. Chi-square analysis was performed as described above to assess for statistically significant differences between the two tissues. Among the 12 studied CpG sites, 5 are statistically significantly different (Chi-square analysis, Tables 4C).

TABLE 4A

Summary of bisulfite sequencing data, methylation indices and chi-square analysis comparing the methylation profile of third-trimester placental tissues and maternal blood cells at the individual CpG sites within PPP1R2P2 region A. The individual CpG sites are designated by their nucleotide positions relative to chr21: 36,180,493 (+1) of the Human May 2004 (hg17) assembly of the UCSC Genome Browser.

| | | CpG579 | CpG582 | CpG587 | CpG589 | CpG591 | CpG605 | CpG613 | CpG616 | CpG618 | CpG625 | CpG637 |
|---|---|---|---|---|---|---|---|---|---|---|---|---|
| Buffy | C | 61 | 61 | 60 | 58 | 60 | 54 | 62 | 62 | 60 | 62 | 60 |
| coat | T | 1 | 1 | 2 | 4 | 2 | 8 | 0 | 0 | 2 | 0 | 2 |
| | MethIndx | 0.98 | 0.98 | 0.97 | 0.94 | 0.97 | 0.87 | 1.00 | 1.00 | 0.97 | 1.00 | 0.97 |
| | C + T | 62 | 62 | 62 | 62 | 62 | 62 | 62 | 62 | 62 | 62 | 62 |
| Placenta | C | 46 | 47 | 61 | 47 | 46 | 46 | 40 | 45 | 34 | 33 | 32 |
| | T | 16 | 15 | 1 | 15 | 16 | 16 | 22 | 17 | 26 | 29 | 30 |
| | MethIndx | 0.74 | 0.76 | 0.93 | 0.76 | 0.74 | 0.74 | 0.65 | 0.73 | 0.55 | 0.53 | 0.52 |
| | C + T | 62 | 62 | 62 | 62 | 62 | 62 | 62 | 62 | 62 | 62 | 62 |
| | Chi-Square | 13.361 | 12.127 | 1.11E−14 | 6.216 | 0.983 | 2.532 | 24.369 | 17.451 | 27.482 | 35.287 | 30.705 |
| | p-value | =<0.001 | =<0.001 | 1.000 | 0.013 | =<0.001 | 0.112 | =<0.001 | =<0.001 | =<0.0011 | =<0.001 | =<0.0011 |

| | | CpG654 | CpG669 | CpG676 | CpG688 | CpG697 | CpG714 | CpG726 | CpG740 | CpG746 |
|---|---|---|---|---|---|---|---|---|---|---|
| Buffy | C | 60 | 57 | 54 | 59 | 58 | 60 | 55 | 60 | 61 |
| coat | T | 2 | 5 | 8 | 3 | 4 | 2 | 7 | 2 | 1 |

TABLE 4A-continued

Summary of bisulfite sequencing data, methylation indices and chi-square analysis comparing the methylation profile of third-trimester placental tissues and maternal blood cells at the individual CpG sites within PPP1R2P2 region A. The individual CpG sites are designated by their nucleotide positions relative to chr21: 36,180,493 (+1) of the Human May 2004 (hg17) assembly of the UCSC Genome Browser.

|          |            |         |         |         |         |         |         |         |         |         |
|----------|------------|---------|---------|---------|---------|---------|---------|---------|---------|---------|
|          | MethIndx   | 0.97    | 0.92    | 0.87    | 0.95    | 0.94    | 0.97    | 0.89    | 0.97    | 0.98    |
|          | C + T      | 62      | 62      | 62      | 62      | 62      | 62      | 62      | 62      | 62      |
| Placenta | C          | 43      | 23      | 36      | 36      | 27      | 49      | 44      | 44      | 49      |
|          | T          | 19      | 39      | 26      | 26      | 35      | 13      | 18      | 18      | 13      |
|          | MethIndx   | 0.69    | 0.37    | 0.58    | 0.58    | 0.44    | 0.79    | 0.71    | 0.71    | 0.79    |
|          | C + T      | 62      | 62      | 62      | 62.     | 62      | 62      | 62      | 62      | 62      |
|          | Chi-Square | 14.676  | 38.363  | 11.711  | 21.784  | 33.665  | 7.584   | 5.01    | 13.413  | 9.743   |
|          | p-value    | =<0.001• | =<0.001 | =<0.001 | =<0.001 | =<0.001 | 0.006   | 0.025   | =<0.001 | 0.002   |

|          |            | CpG765  | CpG774   | CpG784  | CpG802  | CpG815  | CpG817  |
|----------|------------|---------|----------|---------|---------|---------|---------|
| Buffy    | C          | 60      | 58       | 61      | 61      | 62      | 57      |
| coat     | T          | 2       | 4        | 1       |         | 0       | 5       |
|          | MethIndx   | 0.97    | 0.94     | 0.98    | 0.98    | 1.00    | 0.92    |
|          | C + T      | 62      | 62       | 62      | 62      | 62      | 62      |
| Placenta | C          | 51      | 59       | 37      | 29      | 39      | 33      |
|          | T          | 11      | 3        | 25      | 33      | 23      | 29      |
|          | MethIndx   | 0.82    | 0.95     | 0.60    | 0.47    | 0.63    | 0.53    |
|          | C + T      | 62      | 62       | 62      | 62      | 62      | 62      |
|          | Chi-Square | 5.5     | 1.38E−14 | 25.744  | 38.9421 | 25.836  | 21.437  |
|          | p-value    | 0.019   | 1.000    | =<0.001 | =<0.001 | =<0.001 | =<0.001 |

TABLE 4B

Summary of bisulfite sequencing data, methylation indices and chi-square analysis comparing the methylation profile of first-trimester placental tissues and maternal blood cells at the individual CpG sites within PPP1R2P2 region A. The individual CpG sites are designated by their nucleotide positions relative to chr21: 36,180,493 (+1) of the Human May 2004 (hg17) assembly of the UCSC Genome Browser.

|          |            | CpG579  | CpG582  | CpG587  | CpG589  | CpG591  | CpG605  | CpG613  | CpG616  | CpG618  | CpG625  |
|----------|------------|---------|---------|---------|---------|---------|---------|---------|---------|---------|---------|
| Buffy    | C          | 53      | 53      | 53      | 51      | 52      | 53      | 51      | 51      | 54      | 53      |
| coat     | T          | 1       | 1       | 1       | 3       | 2       | 1       | 3       | 3       | 0       | 1       |
|          | MethIndx   | 0.9815  | 0.9815  | 0.981   | 0.9444  | 0.963   | 0.981   | 0.9444  | 0.9444  | 1       | 0.9815  |
|          | C + T      | 54      | 54      | 54      | 54      | 54      | 54      | 54      | 54      | 54      | 54      |
| Placenta | C          | 39      | 35      | 49      | 29      | 40      | 49      | 24      | 33      | 27      | 20      |
|          | T          | 15      | 19      | 5       | 25      | 14      | 5       | 30      | 21      | 27      | 34      |
|          | MethIndx   | 0.7222  | 0.6481  | 0.907   | 0.537   | 0.741   | 0.907   | 0.4444  | 0.6111  | 0.5     | 0.3704  |
|          | C + T      | 54      | 54      | 54      | 54      | 54      | 54      | 54      | 54      | 54      | 54      |
|          | Chi-square | 12.399  | 17.734  | 1.588   | 21.263  | 8.878   | 1.588   | 29.498  | 15.482  | 33.383  | 43.285  |
|          | p-Value    | =<0.001 | =<0.001 | 0.208   | =<0.001 | 0.003   | 0.208   | =<0.001 | =<0.001 | =<0.001 | =<0.001 |

|          |            | CpG637  | CpG654 | CpG669  | CpG676  | CpG688  | CpG697  | CpG714  | CpG726  | CpG740  |
|----------|------------|---------|--------|---------|---------|---------|---------|---------|---------|---------|
| Buffy    | C          | 53      | 44     | 45      | 50      | 49      | 48      | 52      | 53      | 52      |
| coat     | T          | 1       | 10     | 9       | 4       | 5       | 6       | 2       | 1       | 2       |
|          | MethIndx   | 0.9815  | 0.815  | 0.8333  | 1.9259  | 0.9074  | 0.8889  | 0.963   | 0.9815  | 0.963   |
|          | C + T      | 54      | 54     | 54      | 54      | 54      | 54      | 54      | 54      | 54      |
| Placenta | C          | 32      | 35     | 10      | 27      | 20      | 13      | 40      | 29      | 43      |
|          | T          | 22      | 19     | 44      | 27      | 34      | 41      | 14      | 25      | 11      |
|          | MethIndx   | 0.5926  | 0.648  | 0.1852  | 0.5     | 0.3704  | 0.2407  | 0.741   | 0.537   | 0.796   |
|          | C + T      | 54      | 54     | 54      | 54      | 54      | 54      | 54      | 64      | 54      |
|          | Chi-square | 22.097  | 3.017  | 42.83   | 21.899  | 31.465  | 43.547  | 8.878   | 26.797  | 5.597   |
|          | p-Value    | =<0.001 | 0.082  | =<0.001 | =<0.001 | =<0.001 | =<0.001 | 0.003   | =<0.001 | 0.018   |

|          |            | CpG746  | CpG765  | CpG774  | CpG784  | CpG802  | CpG815  | CpG817  |
|----------|------------|---------|---------|---------|---------|---------|---------|---------|
|          | Buffy C    | 53      | 54      | 52      | 51      | 51      | 54      | 51      |
|          | coat  T    | 1       | 0       | 2       | 3       | 3       | 0       | 3       |
|          | MethIndx   | 0.981   | 1       | 0.963   | 0.9444  | 0.9444  | 1       | 0.9444  |
|          | C + T      | 54      | 54      | 54      | 54      | 54      | 54      | 54      |
|          | Placenta C | 42      | 35      | 33      | 27      | 33      | 32      | 22      |
|          | T          | 12      | 19      | 21      | 27      | 21      | 22      | 32      |
|          | MethIndx   | 0.778   | 0.6481  | 0.6111  | 0.5     | 0.6111  | 0.5926  | 0.4074  |
|          | C + T      | 54      | 54      | 54      | 54      | 54      | 54      | 54      |
|          | Chi-square | 8.745   | 20.693  | 17.899  | 24.415  | 15.482  | 25.173  | 33.14   |
|          | p-Value    | 0.003   | =<0.001 | =<0.001 | =<0.001 | =<0.001 | =<0.001 | =<0.001 |

TABLE 4C

Summary of bisulfite sequencing data, methylation indices and chi-square analysis comparing the methylation profile of first-trimester placental tissues and maternal blood cells at the individual CpG sites within PPP1R2P2 region B. The individual CpG sites are designated by their nucleotide positions relative to chr21: 36,180,493 (+1) of the Human May 2004 (hg17) assembly of the UCSC Genome Browser.

|  |  | CpG826 | CpG829 | CpG854 | CpG863 | CpG872 | CpG887 | CpG892 | CpG942 | CpG945 | CpG951 | CpG967 | CpG979 |
|---|---|---|---|---|---|---|---|---|---|---|---|---|---|
| Maternal | C | 31 | 32 | 40 | 38 | 39 | 36 | 36 | 38 | 29 | 30 | 2 | 7 |
| Buffy | T | 9 | 8 | 0 | 2 | 1 | 4 | 4 | 2 | 11 | 10 | 38 | 33 |
| Coat | MethIndx | 0.78 | 0.80 | 1.00 | 0.95 | 0.98 | 0.90 | 0.90 | 0.95 | 0.73 | 0.75 | 0.05 | 0.18 |
|  | C + T | 40 | 40 | 40 | 40 | 40 | 40 | 40 | 40 | 40 | 40 | 40 | 40 |
| Placenta | C | 31 | 30 | 33 | 28 | 26 | 19 | 31 | 27 | 24 | 24 | 0 | 10 |
|  | T | 9 | 10 | 7 | 12 | 14 | 21 | 9 | 13 | 16 | 16 | 40 | 30 |
|  | MethIndx | 0.78 | 0.75 | 0.83 | 0.70 | 0.65 | 0.48 | 0.78 | 0.68 | 0.60 | 0.60 | 0.00 | 0.25 |
|  | C + T | 40 | 40 | 40 | 40 | 40 | 40 | 40 | 40 | 40 | 40 | 40 | 40 |
|  | chi-square | 0.072 | 0.072 | 5.636 | 7.013 | 11.815 | 14.895 | 1.470 | 8.205 | 0.894 | 1.425 | 0.513 | 0.299 |
|  | p-value | 0.789 | 0.789 | 0.018 | 0.008 | =<0.001 | =<0.001 | 0.225 | 0.004 | 0.344 | 0.233 | 0.474 | 0.585 |

Figure 5A:
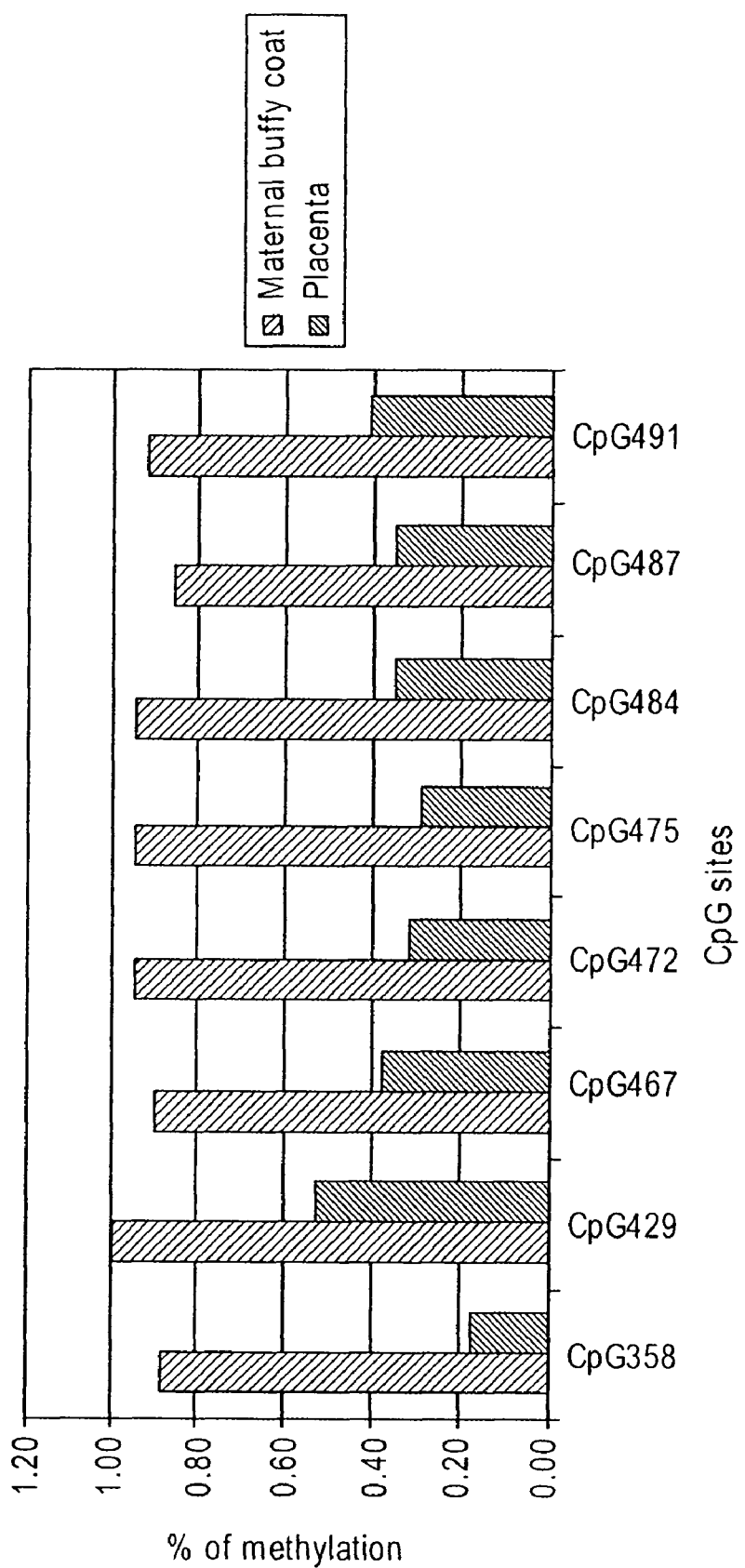
FIG. 5. Box plot of the methylation indices among all of the sequenced clones for the placenta and maternal blood cell samples for each of the studied CpG sites within Similarity to Fem1A (C. elegans) (A), region A and (B). region B. Across the x-axis, the individual CpG sites are designated with their nucleotide positions relative to chr21: 14,056,070 (+1) of the Human May 2004 (hg17) assembly of the UCSC Genome Browser.
Figure 5B:
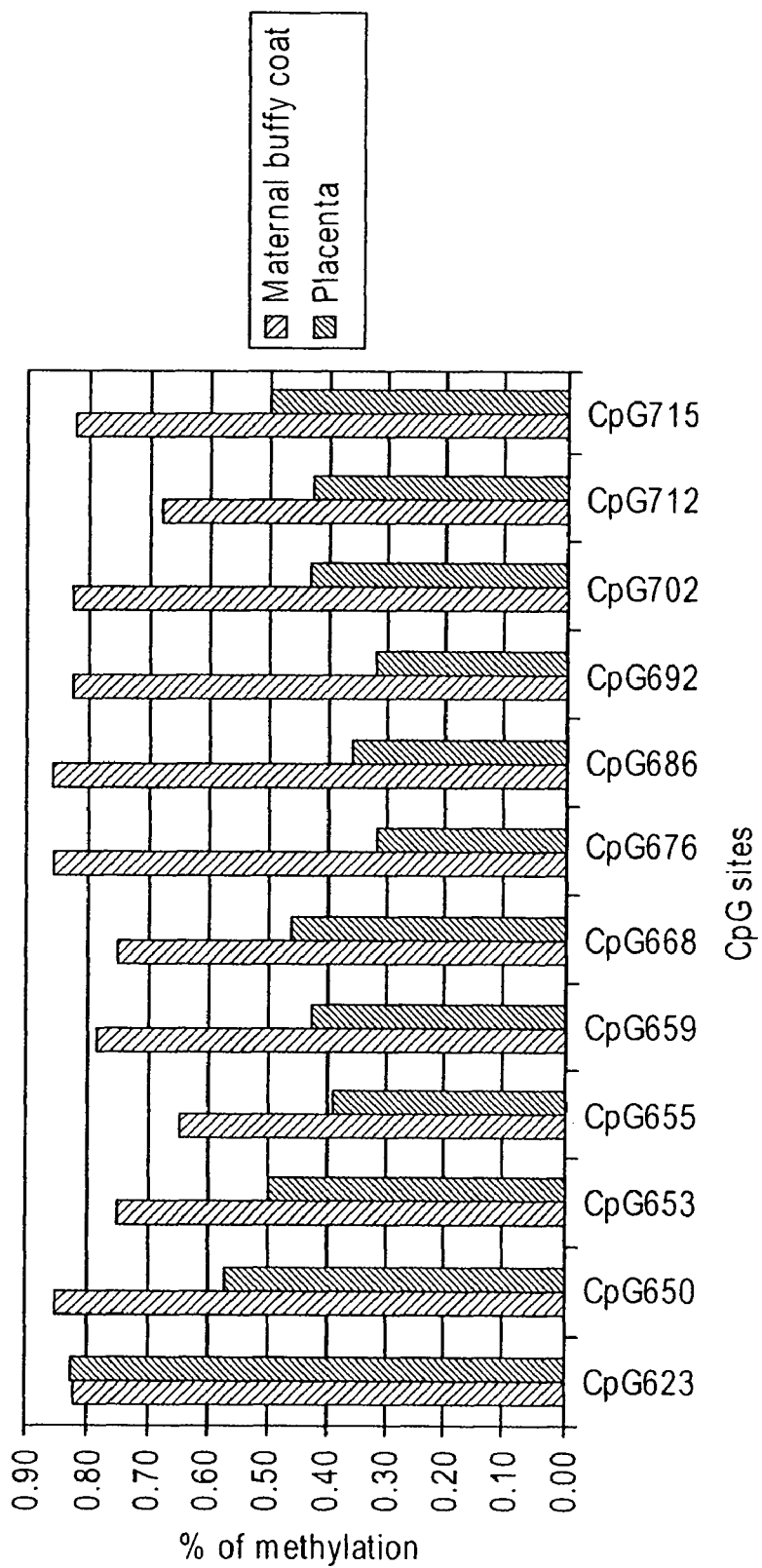

Similarity to Fem1A (*Caenorhabditis elegans* (*C. elegans*)) The methylation profile of Similarity to Fem1A (*C. elegans*) was studied among placental tissues and the corresponding maternal blood cells collected from 5 third-trimester pregnancies. Cloning and bisulfite sequencing were performed and the methylation indices of the studied CpG sites in the placental tissues and maternal blood cells are summarized in FIGS. 5A and 5B for regions A and B, respectively. In general, the placenta is hypomethylated when compared to maternal blood cells. Chi-square analysis was performed as described above to assess for statistically significant differences between the two tissues. Among the studied CpG sites, 8 are statistically significantly different in region A and 7 are statistically significantly different in region B (Chi-square analysis, Tables 5A and 5B).

TABLE 5A

Summary of bisulfite sequencing data, methylation indices and chi-square analysis comparing the methylation profile of third-trimester placental tissues and maternal blood cells at the individual CpG sites within Similarity to Fem1A (*C. elegans*) region A. The individual CpG sites are designated by their nucleotide positions relative to chr21: 14,056,070 (+1) of the Human May 2004 (hg17) assembly of the UCSC Genome Browser.

|  |  | CpG358 | CpG429 | CpG467 | CpG472 | CpG475 | CpG484 | CpG487 | CpG491 |
|---|---|---|---|---|---|---|---|---|---|
| Buffy | C | 39 | 44 | 40 | 42 | 42 | 42 | 38 | 41 |
| coat | T | 5 | 0 | 4 | 2 | 2 | 2 | 6 | 3 |
|  | MethIndx | 0.89 | 1.00 | 0.91 | 0.95 | 0.95 | 0.95 | 0.86 | 0.93 |
| Placneta | C | 8 | 24 | 17 | 14 | 13 | 16 | 16 | 18 |
|  | T | 36 | 20 | 27 | 30 | 31 | 28 | 28 | 26 |
|  | MethIndx | 0.18 | 0.55 | 0.39 | 0.32 | 0.30 | 0.36 | 0.36 | 0.41 |
|  | Chi-square | 41.1 | 23.359 | 24.104 | 35.799 | 38.012 | 31.609 | 16.97 | 24.893 |
|  | P-value | P = <0.001 | P = <0.001 | P = <0.001 | P = <0.001 | P = <0.001 | P = <0.001 | P = <0.001 | P = <0.001 |

TABLE 5B

Summary of bisulfite sequencing data, methylation indices and chi-square analysis comparing the methylation profile of third-trimester placental tissues and maternal blood cells at the individual CpG sites within Similarity to Fem1A (*C. elegans*) region B. The individual CpG sites are designated by their nucleotide positions relative to chr21: 14,056,070 (+1) of the Human May 2004 (hg17) assembly of the UCSC Genome Browser.

|  |  | CpG623 | CpG650 | CpG653 | CpG655 | CpG659 | CpG668 | CpG676 | CpG686 | CpG692 | CpG709 | CpG712 | CpG715 |
|---|---|---|---|---|---|---|---|---|---|---|---|---|---|
| Buffy | C | 23 | 24 | 21 | 18 | 22 | 21 | 24 | 24 | 23 | 23 | 19 | 23 |
| coat | T | 5 | 4 | 7 | 10 | 6 | 7 | 4 | 4 | 5 | 5 | 9 | 5 |
|  | MethIndx | 0.82 | 0.86 | 0.75 | 0.64 | 0.79 | 0.75 | 0.86 | 0.86 | 0.82 | 0.82 | 0.68 | 0.82 |
| Placenta | C | 23 | 16 | 14 | 11 | 12 | 13 | 9 | 10 | 9 | 12 | 12 | 14 |
|  | T | 5 | 12 | 14 | 17 | 16 | 15 | 19 | 18 | 19 | 16 | 16 | 14 |
|  | MethIndx | 0.82 | 0.57 | 0.50 | 0.39 | 0.43 | 0.46 | 0.32 | 0.36 | 0.32 | 0.43 | 0.43 | 0.50 |
|  | Chi-square | 0.122 | 4.288 | 2.743 | 2.575 | 6.064 | 3.668 | 14.461 | 12.652 | 12.323 | 7.619 | 2.601 | 5.098 |
|  | P-value | 0.727 | 0.038 | 0.098 | 0.109 | 0.014 | 0.055 | P = <0.001 | P = <0.001 | P = <0.001 | 0.006 | 0.107 | 0.024 |

Figure 6:
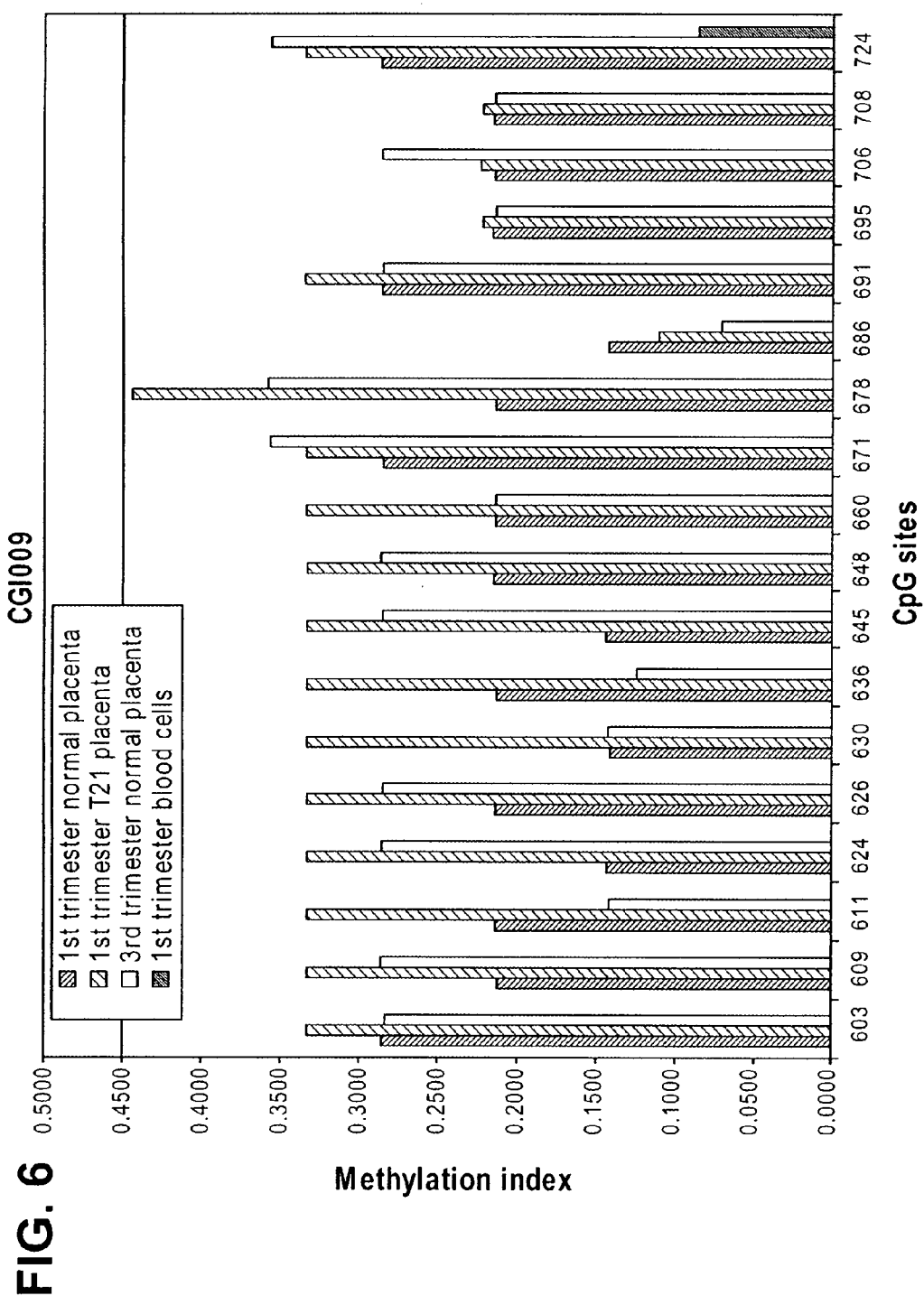
FIG. 6. Box plot of the methylation indices among all of the sequenced clones for the placenta and maternal blood cell samples for each of the studied CpG sites within CGI009. Across the x-axis, the individual CpG sites are designated with their nucleotide positions relative to chr21: 25,855,701 (+1) of the Human May 2004 (hg17) assembly of the UCSC Genome Browser.

CGI009 The methylation profiles of CGI009 from 2 maternal blood cell samples were compared with those of 2 first-trimester and 2 third-trimester placental tissue samples collected from normal pregnancies as well as 2 first-trimester placental tissue samples from pregnancies where the fetus had trisomy 21. Cloning and bisulfite sequencing were performed and the methylation indices of the studied CpG sites in the placental tissues and maternal blood cells are summarized in FIG. 6. In general, the placenta is hypermethylated when compared to maternal blood cells.

Carbonyl reductase 1 (CBR1) The profiles of CBR1 from 2 maternal blood cell samples were compared with those of 2 first-trimester placental tissue samples collected from normal pregnancies as well as 2 first-trimester placental tissue samples from pregnancies where the fetus had trisomy 21. Cloning and bisulfite sequencing were performed and the methylation indices of the studied CpG sites in the placental tissues and maternal blood cells are summarized in FIG. 7. In general, the placenta is hypermethylated when compared to maternal blood cells. Among the 20 studied CpG sites, all are statistically significantly different between the maternal blood cells and first-trimester placental tissues of both normal and trisomy 21 pregnancies (Chi-square analysis, Table 6).

TABLE 6

Summary of bisulfite sequencing data, methylation indices and chi-square analysis comparing the methylation profile of normal and trisomy 21 first-trimester placental tissues and maternal blood cells at the individual CpG sites within CBR1. The individual CpG sites are designated by their nucleotide positions relative to chr21: 36,363,538 (+1) of the Human May 2004 (hg17) assembly of the UCSC Genome Browser.

| | CpG | 474 | 481 | 488 | 520 | 529 | 536 | 539 | 547 | 577 | 582 |
|---|---|---|---|---|---|---|---|---|---|---|---|
| Maternal | #C | 0 | 0 | 0 | 0 | 0 | 0 | 0 | 0 | 0 | 0 |
| buffy coat | #T | 28 | 28 | 28 | 28 | 28 | 28 | 28 | 28 | 28 | 28 |
| 1st trimester | #C | 11 | 11 | 9 | 8 | 6 | 7 | 7 | 5 | 10 | 8 |
| T21 placenta | #T | 15 | 15 | 17 | 18 | 20 | 19 | 19 | 21 | 16 | 18 |
| 1st normal | #C | 8 | 8 | 6 | 7 | 8 | 7 | 8 | 7 | 8 | 6 |
| placenta | #T | 14 | 14 | 16 | 15 | 14 | 15 | 14 | 15 | 14 | 16 |
| 1st trimester T21 placenta | chi-square | 12.383 | 12.383 | 9.272 | 7.823 | 5.12 | 6.439 | 6.439 | 3.866 | 10.791 | 7.823 |
| vs maternal blood cells | P-value | <0.001 | 0.001 | 0.002 | 0.005 | 0.024 | 0.011 | 0.011 | 0.049 | 0.001 | 0.005 |
| 1st trimester normal placenta | chi-square | 9.567 | 9.567 | 6.287 | 7.885 | 9.567 | 7.885 | 9.567 | 7.885 | 9.567 | 6.287 |
| vs maternal blood cells | P-value | 0.002 | 0.002 | 0.012 | 0.005 | 0.002 | 0.005 | 0.002 | 0.005 | 0.002 | 0.012 |
| | CpG | 590 | 599 | 605 | 607 | 614 | 618 | 622 | 633 | 639 | 641 |
| Maternal | #C | 0 | 0 | 0 | 0 | 0 | 0 | 0 | 0 | 1 | 0 |
| buffy coat | #T | 28 | 28 | 28 | 28 | 28 | 28 | 28 | 28 | 27 | 28 |
| 1st trimester | #C | 7 | 10 | 8 | 6 | 7 | 8 | 8 | 7 | 7 | 7 |
| T21 placenta | #T | 19 | 16 | 18 | 20 | 19 | 18 | 18 | 19 | 19 | 19 |
| 1st normal | #C | 7 | 6 | 8 | 8 | 8 | 7 | 7 | 6 | 5 | 8 |
| placenta | #T | 15 | 16 | 14 | 14 | 14 | 15 | 15 | 16 | 17 | 14 |
| 1st trimester T21 placenta | chi-square | 6.439 | 10.791 | 7.823 | 5.12 | 6.439 | 7.823 | 7.823 | 6.439 | 4.122 | 6.439 |
| vs maternal blood cells | P-value | 0.011 | 0.001 | 0.005 | 0.024 | 0.011 | 0.005 | 0.005 | 0.011 | 0.042 | 0.011 |
| 1st trimester normal placenta | chi-square | 7.885 | 6.287 | 9.567 | 9.567 | 9.567 | 7.885 | 7.885 | 6.287 | 2.659 | 9.567 |
| vs maternal blood cells | P-value | 0.005 | 0.012 | 0.002 | 0.002 | 0.002 | 0.005 | 0.005 | 0.012 | 0.103 | 0.002 |
| Methylation Index | | 474 | 481 | 488 | 520 | 529 | 536 | 539 | 547 | 577 | 582 |
| 1st trimester normal placenta | | 0.3636 | 0.3636 | 0.2727 | 0.3182 | 0.3636 | 0.3182 | 0.3636 | 0.3182 | 0.3636 | 0.2727 |
| 1st trimester T21 placenta | | 0.4231 | 0.4231 | 0.3462 | 0.3077 | 0.2308 | 0.2692 | 0.2692 | 0.1923 | 0.3846 | 0.3077 |
| 1st trimester maternal blood cells | | 0 | 0 | 0 | 0 | 0 | 0 | 0 | 0 | 0 | 0 |
| Methylation Index | | 590 | 599 | 605 | 607 | 614 | 618 | 622 | 633 | 639 | 641 |
| 1st trimester normal placenta | | 0.3182 | 0.2727 | 0.3636 | 0.3636 | 0.3636 | 0.3182 | 0.3182 | 0.2727 | 0.2273 | 0.3636 |
| 1st trimester T21 placenta | | 0.2692 | 0.3846 | 0.3077 | 0.2308 | 0.2692 | 0.3077 | 0.3077 | 0.2692 | 0.2692 | 0.2692 |
| 1st trimester maternal blood cells | | 0 | 0 | 0 | 0 | 0 | 0 | 0 | 0 | 0.0357 | 0 |

Down syndrome cell adhesion molecule (DSCAM) The methylation profiles of DSCAM from 2 maternal blood cell samples were compared with those of 2 first-trimester and 2 third-trimester placental tissue samples collected from normal pregnancies as well as 2 first-trimester placental tissue samples from pregnancies where the fetus had trisomy 21.

Cloning and bisulfite sequencing were performed and the methylation indices of the studied CpG sites in the placental tissues and maternal blood cells are summarized in FIG. 8. In general, the placenta is hypermethylated when compared to maternal blood cells. Among the 27 studied CpG sites, all are statistically significantly different between the maternal blood cells and first-trimester placental tissues of both normal and trisomy 21 pregnancies (Chi-square analysis, Table 7).

TABLE 7

Summary of bisulfite sequencing data, methylation indices and chi-square analysis comparing the methylation profiles of normal and trisomy 21 first-trimester placental tissues and maternal blood cells at the individual CpG sites within DSCAM. The individual CpG sites are designated by their nucleotide positions relative to chr21: 41,139,872 (+1) of the Human May 2004 (hg17) assembly of the UCSC Genome Browser.

| | CpG | 810 | 814 | 817 | 819 | 826 | 831 | 835 | 848 | 851 | 870 |
|---|---|---|---|---|---|---|---|---|---|---|---|
| Maternal | #C | 2 | 1 | 1 | 1 | 1 | 2 | 2 | 1 | 2 | 0 |
| buffy coat | #T | 24 | 25 | 25 | 25 | 25 | 24 | 24 | 25 | 24 | 26 |
| T21 placenta | #C | 9 | 9 | 9 | 10 | 9 | 9 | 10 | 10 | 9 | 10 |
| | #T | 5 | 5 | 5 | 4 | 5 | 5 | 4 | 4 | 5 | 4 |
| 3rd normal | #C | 4 | 3 | 3 | 3 | 3 | 4 | 4 | 1 | 5 | 5 |
| placenta | #T | 20 | 21 | 21 | 21 | 21 | 20 | 20 | 23 | 19 | 19 |
| 1st normal | #C | 8 | 8 | 8 | 8 | 10 | 8 | 8 | 8 | 8 | 8 |
| placenta | #T | 10 | 10 | 10 | 10 | 8 | 10 | 10 | 10 | 10 | 10 |
| 1st trimester normal placenta | chisq | 6.222 | 8.424 | 8.424 | 8.424 | 12.536 | 6.222 | 6.222 | 8.424 | 6.222 | 11.294 |
| vs maternal blood cells | P | 0.013 | 0.004 | 0.004 | 0.004 | <0.001 | 0.013 | 0.013 | 0.004 | 0.013 | 0.001 |
| 3rd trimester normal placenta | chi-square | 0.292 | 0.366 | 0.366 | 0.366 | 0.366 | 0.292 | 0.292 | 0.442 | 0.865 | 3.926 |
| vs maternal blood cells | P-value | 0.589 | 0.545 | 0.545 | 0.545 | 0.545 | 0.589 | 0.589 | 0.506 | 0.352 | 0.048 |
| 1st trimester T21 placenta | chi-square | 11.918 | 14.652 | 14.652 | 17.595 | 14.652 | 11.918 | 14.699 | 17.595 | 11.918 | 21.099 |
| vs maternal blood cells | P-value | <0.001 | <0.001 | <0.001 | <0.001 | <0.001 | <0.001 | <0.001 | <0.001 | <0.001 | 0.001 |

| | CpG | 878 | 895 | 901 | 903 | 907 | 920 | 928 | 931 | 942 |
|---|---|---|---|---|---|---|---|---|---|---|
| Maternal | #C | 1 | 2 | 1 | 0 | 0 | 0 | 1 | 1 | 1 |
| buffy coat | #T | 25 | 24 | 25 | 26 | 26 | 26 | 25 | 25 | 25 |
| T21 placenta | #C | 9 | 9 | 9 | 10 | 10 | 10 | 8 | 9 | 10 |
| | #T | 5 | 5 | 5 | 4 | 4 | 4 | 6 | 5 | 4 |
| 3rd normal | #C | 5 | 3 | 2 | 2 | 3 | 2 | 3 | 2 | 3 |
| placenta | #T | 19 | 21 | 22 | 22 | 21 | 22 | 21 | 22 | 21 |
| 1st normal | #C | 6 | 9 | 8 | 8 | 8 | 7 | 8 | 7 | 7 |
| placenta | #T | 12 | 9 | 10 | 10 | 10 | 11 | 10 | 11 | 11 |
| 1st trimester normal placenta | chisq | 4.885 | 8.023 | 8.424 | 11.294 | 11.294 | 9.293 | 8.424 | 6.583 | 6.583 |
| vs maternal blood cells | P | 0.027 | 0.005 | 0.004 | <0.001 | <0.001 | 0.002 | 0.004 | 0.01 | 0.01 |
| 3rd trimester normal placenta | chi-square | 1.991 | 0.0089 | 0.0051 | 0.608 | 1.596 | 0.608 | 0.366 | 0.0051 | 0.366 |
| vs maternal blood cells | P-value | 0.158 | 0.925 | 0.943 | 0.435 | 0.206 | 0.435 | 0.545 | 0.943 | 0.545 |
| 1st trimester T21 placenta | chi-square | 14.652 | 11.918 | 14.652 | 21.099 | 21.099 | 21.099 | 11.925 | 14.652 | 17.595 |
| vs maternal blood cells | P-value | <0.001 | <0.001 | <0.001 | <0.001 | <0.001 | <0.001 | <0.001 | <0.001 | <0.001 |

| Methylation Index | CpG | 810 | 814 | 817 | 819 | 826 | 831 | 835 | 848 | 851 | 870 |
|---|---|---|---|---|---|---|---|---|---|---|---|
| 1st trimester normal placenta | | 0.4444 | 0.4444 | 0.4444 | 0.4444 | 0.5556 | 0.4444 | 0.4444 | 0.4444 | 0.4444 | 0.4444 |
| 1st trimester T21 placenta | | 0.6429 | 0.6429 | 0.6429 | 0.7143 | 0.6429 | 0.6429 | 0.7143 | 0.7143 | 0.6429 | 0.7143 |
| 3rd trimester normal placenta | | 0.1667 | 0.125 | 0.125 | 0.125 | 0.125 | 0.1667 | 0.1667 | 0.0417 | 0.2083 | 0.2083 |
| 1st trimester blood cells | | 0.0769 | 0.0385 | 0.0385 | 0.0385 | 0.0385 | 0.0769 | 0.0769 | 0.0385 | 0.0769 | 0 |

| Methylation Index | CpG | 878 | 895 | 901 | 903 | 907 | 920 | 928 | 931 | 942 |
|---|---|---|---|---|---|---|---|---|---|---|
| 1st trimester normal placenta | | 0.3333 | 0.5 | 0.4444 | 0.4444 | 0.4444 | 0.3889 | 0.4444 | 0.3889 | 0.3889 |
| 1st trimester T21 placenta | | 0.6429 | 0.6429 | 0.6429 | 0.7143 | 0.7143 | 0.7143 | 0.5714 | 0.6429 | 0.7143 |
| 3rd trimester normal placenta | | 0.2083 | 0.125 | 0.0833 | 0.0833 | 0.125 | 0.0833 | 0.125 | 0.0833 | 0.125 |
| 1st trimester blood cells | | 0.0385 | 0.0769 | 0.0385 | 0 | 0 | 0 | 0.0385 | 0.0385 | 0.0385 |

Chromosome 21 open reading frame 29 (C21orf29) The methylation profiles of C21orf29 from 2 maternal blood cell samples were compared with those of 1 first-trimester and 2 third-trimester placental tissue samples collected from normal pregnancies as well as 2 first-trimester placental tissue samples from pregnancies where the fetus had trisomy 21. Cloning and bisulfite sequencing were performed and the methylation indices of the studied CpG sites in the placental tissues and maternal blood cells are summarized in FIG. 9. In general, the placenta is hypermethylated when compared to maternal blood cells. Among the 16 studied CpG sites, all, 9 and 10 sites are statistically significantly different between the maternal blood cells and first-trimester placental tissues of trisomy 21 pregnancies, first-trimester and third-trimester placental tissues of normal pregnancies, respectively (Chi-square analysis, Table 8).

TABLE 8

Summary of bisulfite sequencing data, methylation indices and chi-square analysis comparing the methylation profile of normal and trisomy 21 first-trimester placental tissues and maternal blood cells at the individual CpG sites within C21orf29. The individual CpG sites are designated by their nucleotide positions relative to chr21: 44,953,288 (+1) of the Human May 2004 (hg17) assembly of the UCSC Genome Browser.

| | CpG | 533 | 540 | 555 | 558 | 601 | 612 | 623 | 637 |
|---|---|---|---|---|---|---|---|---|---|
| 1st trimester normal placenta | #C | 5 | 4 | 6 | 4 | 8 | 4 | 3 | 1 |
| | #T | 3 | 4 | 2 | 4 | 0 | 4 | 5 | 7 |
| 1st trimester T21 placenta | #C | 9 | 10 | 9 | 5 | 12 | 10 | 11 | 12 |
| | #T | 7 | 6 | 7 | 11 | 4 | 6 | 5 | 4 |
| 3rd trimester normal placenta | #C | 5 | 6 | 4 | 2 | 13 | 4 | 14 | 7 |
| | #T | 17 | 16 | 18 | 20 | 9 | 18 | 8 | 15 |
| 1st trimester maternal blood cells | #C | 0 | 1 | 0 | 1 | 2 | 1 | 3 | 2 |
| | #T | 24 | 23 | 24 | 23 | 22 | 23 | 21 | 22 |
| 1st trimester normal placenta vs 1st trimester maternal blood cells | Chi-square | 13.3531 | 6.4000 | 17.5043 | 6.4000 | 19.3939 | 6.4000 | 1.0940 | 0.1226 |
| | p-value | 0.0003 | 0.0114 | 0.0000 | 0.0114 | 0.0000 | 0.0114 | 0.2956 | 0.7262 |
| 1st trimester T21 plaenta vs 1st trimester matenral blood cells | Chi-square | 14.3429 | 13.589 | 14.3429 | 3.6029 | 15.9386 | 13.589 | 10.994 | 15.939 |
| | p-value | 0.00015 | 0.0002 | 0.00015 | 0.0577 | 6.5E−05 | 0.0002 | 0.0009 | 7E−05 |
| 3rd trimester normal placenta vs 1st trimester maternal blood cells | Chi-square | 3.99865 | 3.1277 | 2.76351 | 0.9379 | 11.2461 | 1.1054 | 10.781 | 2.6688 |
| | p-value | 0.04554 | 0.077 | 0.09644 | 0.0061 | 0.0008 | 0.2931 | 0.001 | 0.1023 |

| | CpG | 639 | 643 | 656 | 669 | 672 | 674 | 682 | 685 |
|---|---|---|---|---|---|---|---|---|---|
| 1st trimester normal placenta | #C | 1 | 4 | 3 | 1 | 1 | 2 | 3 | 1 |
| | #T | 7 | 4 | 5 | 7 | 7 | 6 | 5 | 7 |
| 1st trimester T21 placenta | #C | 7 | 12 | 12 | 11 | 7 | 8 | 8 | 8 |
| | #T | 9 | 4 | 4 | 5 | 9 | 8 | 8 | 8 |
| 3rd trimester normal placenta | #C | 8 | 11 | 5 | 2 | 1 | 2 | 1 | 4 |
| | #T | 14 | 11 | 17 | 20 | 21 | 20 | 21 | 18 |
| 1st trimester maternal blood cells | #C | 1 | 2 | 0 | 1 | 2 | 1 | 0 | 1 |
| | #T | 23 | 22 | 24 | 23 | 22 | 23 | 24 | 23 |
| 1st trimester normal placenta vs 1st trimester maternal blood cells | Chi-square | N/A | 4.3761 | 6.0077 | N/A | 0.1226 | 1.1034 | 6.0077 | N/A |
| | p-value | N/A | 0.0364 | 0.0142 | N/A | 0.7262 | 0.2935 | 0.0142 | N/A |
| 1st trimester T21 plaenta vs 1st trimester maternal blood cells | Chi-square | 7.0898 | 15.939 | 22.267 | 16.116 | 5.0239 | 9.086 | 12.038 | 9.086 |
| | p-value | 0.0078 | 7E−05 | 2E−06 | 6E−05 | 0.025 | 0.0026 | 0.0005 | 0.0026 |
| 3rd trimester normal placenta vs 1st trimester maternal blood cells | Chi-square | 5.6535 | 7.8813 | 3.9987 | 0.9379 | 0.0061 | 0.0061 | 0.0019 | 1.1054 |
| | p-value | 0.0174 | 0.005 | 0.0455 | 0.0061 | 0.9379 | 0.9379 | 0.9649 | 0.2931 |

| Methylation Index | CpG | 533 | 540 | 555 | 558 | 601 | 612 | 623 | 637 |
|---|---|---|---|---|---|---|---|---|---|
| 1st trimester normal placenta | | 0.6250 | 0.5000 | 0.7500 | 0.5000 | 1.0000 | 0.5000 | 0.3750 | 0.1250 |
| 1st trimester T21 placenta | | 0.5625 | 0.6250 | 0.5625 | 0.3125 | 0.7500 | 0.6250 | 0.6875 | 0.7500 |
| 3rd trimester normal placenta | | 0.2273 | 0.2727 | 0.1818 | 0.0909 | 0.5909 | 0.1818 | 0.6364 | 0.3182 |
| 1st trimester maternal blood cells | | 0.0000 | 0.0417 | 0.0000 | 0.0417 | 0.0833 | 0.0417 | 0.1250 | 0.0833 |

| Methylation Index | CpG | 639 | 643 | 656 | 669 | 672 | 674 | 682 | 685 |
|---|---|---|---|---|---|---|---|---|---|
| 1st trimester normal placenta | | 0.1250 | 0.5000 | 0.3750 | 0.1250 | 0.1250 | 0.2500 | 0.3750 | 0.1250 |
| 1st trimester T21 placenta | | 0.4375 | 0.7500 | 0.7500 | 0.6875 | 0.4375 | 0.5000 | 0.5000 | 0.5000 |
| 3rd trimester normal placenta | | 0.3636 | 0.5000 | 0.2273 | 0.0909 | 0.0455 | 0.0909 | 0.0455 | 0.1818 |
| 1st trimester maternal blood cells | | 0.0417 | 0.0833 | 0.0000 | 0.0417 | 0.0833 | 0.0417 | 0.0000 | 0.0417 |

Genetic loci that showed no differential methylation pattern between placental tissues and maternal blood cells Differential methylation between placental tissues and maternal blood cells was not universally observed for all studied loci. The methylation profile of CGI111 was studied among placental tissues and the corresponding maternal blood cells collected from 4 third-trimester pregnancies. Cloning and bisulfite sequencing were performed and the results are shown in FIG. 10. Clones from both the maternal blood cells and placental tissues were predominantly unmethylated.

Similarly, the methylation profile between maternal blood cells and placental tissues of 5 third-trimester pregnancies were not significantly different for CGI121 except at the CpG site 1603 (FIG. 11 and Table 9).

TABLE 9

Summary of bisulfite sequencing data, methylation indices and chi-square analysis comparing the methylation profile of first-trimester placental tissues and maternal blood cells at the individual CpG sites within CGI121. The individual CpG sites are designated by their nucleotide positions relative to chr21: 45,262,112 (+1) of the Human May 2004 (hg17) assembly of the UCSC Genome Browser.

|  |  | CpG 1477 | CpG 1480 | CpG 1483 | CpG 1505 | CpG 1512 | CpG 1514 | CpG 1518 | CpG 1528 | CpG 1533 | CpG 1553 | CpG 1560 |
|---|---|---|---|---|---|---|---|---|---|---|---|---|
| Buffy coat | C | 3 | 1 | 3 | 5 | 8 | 8 | 10 | 9 | 6 | 8 | 3 |
|  | T | 19 | 21 | 19 | 17 | 14 | 14 | 12 | 13 | 16 | 14 | 19 |
|  | MethIndx | 0.14 | 0.05 | 0.14 | 0.23 | 0.36 | 0.36 | 0.45 | 0.41 | 0.27 | 0.36 | 0.14 |
|  | C + T | 22 | 22 | 22 | 22 | 22 | 22 | 22 | 22 | 22 | 22 | 22 |
| Placenta | C | 7 | 5 | 7 | 9 | 14 | 15 | 14 | 9 | 6 | 13 | 4 |
|  | T | 15 | 17 | 15 | 13 | 8 | 7 | 8 | 13 | 16 | 9 | 18 |
|  | MethIndx | 0.32 | 023 | 032 | 0.41 | 0.64 | 0.68 | 0.64 | 0.41 | 0.27 | 0.59 | 0.18 |
|  | C + T | 22 | 22 | 22 | 22 | 22 | 22 | 22 | 22 | 22 | 22 | 22 |
|  | Chi-square | 1.165 | 1.737 | 1.165 | 0.943 | 2.273 | 3.280 | 0.825 | 0.094 | 0.115 | 1.458 | 6E−16 |
|  | p-value | 0.280 | 0.188 | 0.280 | 0.332 | 0.132 | 0.070 | 0.364 | 0.759 | 0.735 | 0.227 | 1.000 |

|  |  | CpG 1567 | CpG 1581 | CpG 1603 | CpG 1610 | CpG 1616 | CpG 1619 | CpG 1643 | CpG 1648 | CpG 1656 | CpG 1659 |
|---|---|---|---|---|---|---|---|---|---|---|---|
| Buffy coat | C | 5 | 8 | 3 | 10 | 7 | 10 | 14 | 14 | 13 | 17 |
|  | T | 17 | 14 | 19 | 12 | 15 | 12 | 8 | 8 | 9 | 5 |
|  | MethIndx | 0.23 | 0.36 | 0.14 | 0.45 | 0.32 | 0.45 | 0.64 | 0.64 | 0.59 | 0.77 |
|  | C + T | 22 | 22 | 22 | 22 | 22 | 22 | 22 | 22 | 22 | 22 |
| Placenta | C | 3 | 9 | 11 | 11 | 9 | 6 | 10 | 14 | 14 | 11 |
|  | T | 19 | 13 | 11 | 11 | 13 | 16 | 12 | 8 | 8 | 11 |
|  | MethIndx | 0.14 | 0.41 | 0.50 | 0.50 | 0.41 | 0.27 | 0.45 | 0.64 | 0.64 | 0.5 |
|  | C + T | 22 | 22 | 22 | 22 | 22 | 22 | 22 | 22 | 22 | 22 |
|  | Chi-square | 0.153 | 0.096 | 5.133 | 0.091 | 0.098 | 0.884 | 0.825 | 0.098 | 0.096 | 2.455 |
|  | p-value | 0.696 | 0.757 | 0.023 | 0.763 | 0.754 | 0.347 | 0.364 | 0.754 | 0.757 | 0.117 |

On the other hand, for KIAA0656, Heat shock transcription factor 2 binding protein (HSF2BP) and COL6A1, the studied placental tissues and maternal blood cells were both predominantly methylated with no significant differences between the methylation index.

Example 2

The CG-containing genomic sequences with differential methylation profile between placental tissues and maternal blood cells are useful as fetal epigenetic markers for maternal blood detection. In order to distinguish the fetal-derived DNA molecules from those that are maternally-derived in maternal blood, assays should target the detection of the placental-specific epigenetic form of each differentially methylated locus. An assay has been developed to target the placental-specific form of CGI137 (FIG. 1), namely the unmethylated molecules, and assessed its specificity.

Materials and Methods

Sample processing and DNA extraction. A third-trimester placental tissue sample and corresponding maternal blood sample were collected from a subject undergoing delivery by elective cesarean section. Maternal blood (10 mL) was collected into EDTA tubes prior to as well as after the delivery. The blood samples were centrifuged at 1600×g for 10 min at 4° C. The buffy coat portion was obtained after careful removal of plasma and stored separately at −20 ° C. The plasma was further centrifuged at 16,000×g for 10 min and 1.6 mL plasma was transferred to clean polypropylene tubes with care not to disturb the underlying cell pellet. Placental tissue biopsies were rinsed in phosphate buffered saline and stored in plain polypropylene tubes at −80° C. DNA was extracted from the placental tissues using the QIAamp DNA Mini Kit (Qiagen, Hilden, Germany). DNA from the maternal plasma and buffy coat was extracted by the QIAamp DNA Blood Mini Kit (Qiagen, Hilden, Germany) according to the manufacturer's instructions. For each placental and buffy coat DNA sample, 1 μg DNA was subjected to bisulfite conversion, which converts unmethylated cytosine residues to uracil but leaves methylated cytosine residues unchanged, by the Methylamp™ DNA Modification Kit (Epigentek Inc., New York, N.Y.) according to manufacturer's instructions. DNA extracted from 1.6 mL plasma was also subjected to bisulfite conversion. Additional aliquots of mixed bisulfite-converted DNA were also prepared comprised of mixtures of the buffy coat and placental DNA preparations in the ratios of 95:5.

Homogeneous MassEXTEND assay As placental tissues are hypomethylated with respect to maternal blood cells at CGI137 (FIGS. 1 and 2), an assay targeting the detection of the unmethylated form of CGI137 was designed. The assay is based on the MassARRAY (Sequenom, San Diego, Calif.) platform. Methylation specific primers are designed for the specific amplification of the unmethylated form of CGI137. An illustration of the location of the primers is shown in FIG. 12 and the primer sequences are listed in Table 10. The forward primer spans the CpG sites 472, 477, 481 and 486.

The reverse primer spans the CpG sites 553 and 561. The amplicon spans between coordinates: 2742998-2743130 for the GenBank Accession: NT_011515. A primer extension assay (FIG. 12) based on the homogeneous MassEXTEND (hME) protocol is designed to interrogate the methylation status of the CpG site 541. Basically, the primer extension primer spans up to the nucleotide 3' to the CpG site 541 (Table 10). An unmethylated molecule would be extended by one nucleotide with the incorporation of a dd(2',3'-dideoxynucleoside)ATP, while a methylated molecule would be extended by two nucleotides with the incorporation of a dGTP followed by a ddATP. The unmethylated and methylated molecules are subsequently detected and resolved by their mass differences on a MassARRAY™ Analyzer Compact (Sequenom) mass spectrometry.

TABLE 10

Primer sequences of the hME assay targeting the unmethylated form of CGI137.

| Primer | Sequence (5' to 3') (SEQ ID NO:) |
|---|---|
| Forward primer | TGTTATAGGTAGGGATATGTTTTGTTTGACGT (3) |
| Reverse primer | TCTCTACCTACAATTCTATAAAAAACACTTATCCA (48) |
| Extension primer | ATCCCCAACATTTTCCC (49) |

Three μL of bisulfite-converted DNA from the placental (equivalent to 150 ng DNA before bisulfite conversion), maternal buffy coat samples and mixtures as well as ten μL of bisulfite-converted plasma DNA (equivalent to DNA extracted from 1.6 mL maternal plasma) were amplified for each 25 μL PCR reaction. Each reaction contained 1×PCR buffer (Applied Biosystems, Foster City, Calif.) with 2.0 mM MgCl$_2$ (Applied Biosystems), 200 μM each of dATP, dGTP and dCTP, 400 μM of dUTP (Applied Biosystems), 200 nM each of forward and reverse primers (Integrated DNA Technologies, Coralville, IA) and 1 U of AmpliTaq Gold® DNA Polymerase (Applied Biosystems). The PCR reaction was initiated at 95° C. for 10 min, followed by denaturation at 94° C. for 30 sec, annealing at 60° C. for 40 sec, extension at 72° C. for 40 sec for 40 cycles, and a final incubation at 72° C. for 5 mm.

PCR products were subjected to shrimp alkaline phosphatase treatment to dephosphorylate any remaining dNTPs and prevent their incorporation in the subsequent primer extension assay. For each 25 μL PCR reaction, 0.34 μL of hME buffer (Sequenom), 0.6 μL of shrimp alkaline phosphatase (Sequenom) and 3.06 μL of water were added. The reaction mixture was incubated at 37° C. for 40 min, followed by heat inactivation at 85° C. for 5 min.

For the primer extension reaction, 4 μL of base extension reaction cocktail containing 1500 nM of extension primer (Integrated DNA Technologies), 1.15 U of Thermosequenase (Sequenom) and 64 μM each of ddATP, ddCTP, dTTP and dGTP (Sequenom) were added to 10 μL of the PCR products. The reaction condition was 94° C. for 2 min, followed by 94° C. for 5 sec, 52° C. for 5 sec, and 72° C. for 5 sec for 75 cycles.

The final base extension product was cleaned up with the SpectroCLEAN (Sequenom) resin to remove salts that may interfere with the mass spectrometry analysis. Twenty-four microliters of water and 12 mg of resin were added into each base extension product. The final mixtures were mixed in a rotator for 20 min. After centrifugation at 361 g for 5 min, approximately 10 nL of reaction solution was dispensed onto a 384-format SpectroCHIP (Sequenom) pre-spotted with a matrix of 3-hydroxypicolinic acid by using a SpectroPoint nanodispenser (Sequenom). A MassARRAY™ Analyzer Compact Mass Spectrometer (Sequenom) was used for data acquisition from the SpectroCHIP. Mass spectrometric data were automatically imported into SpectroTYPER (Sequenom) database for analysis.

Results and Conclusion

Figure 13:
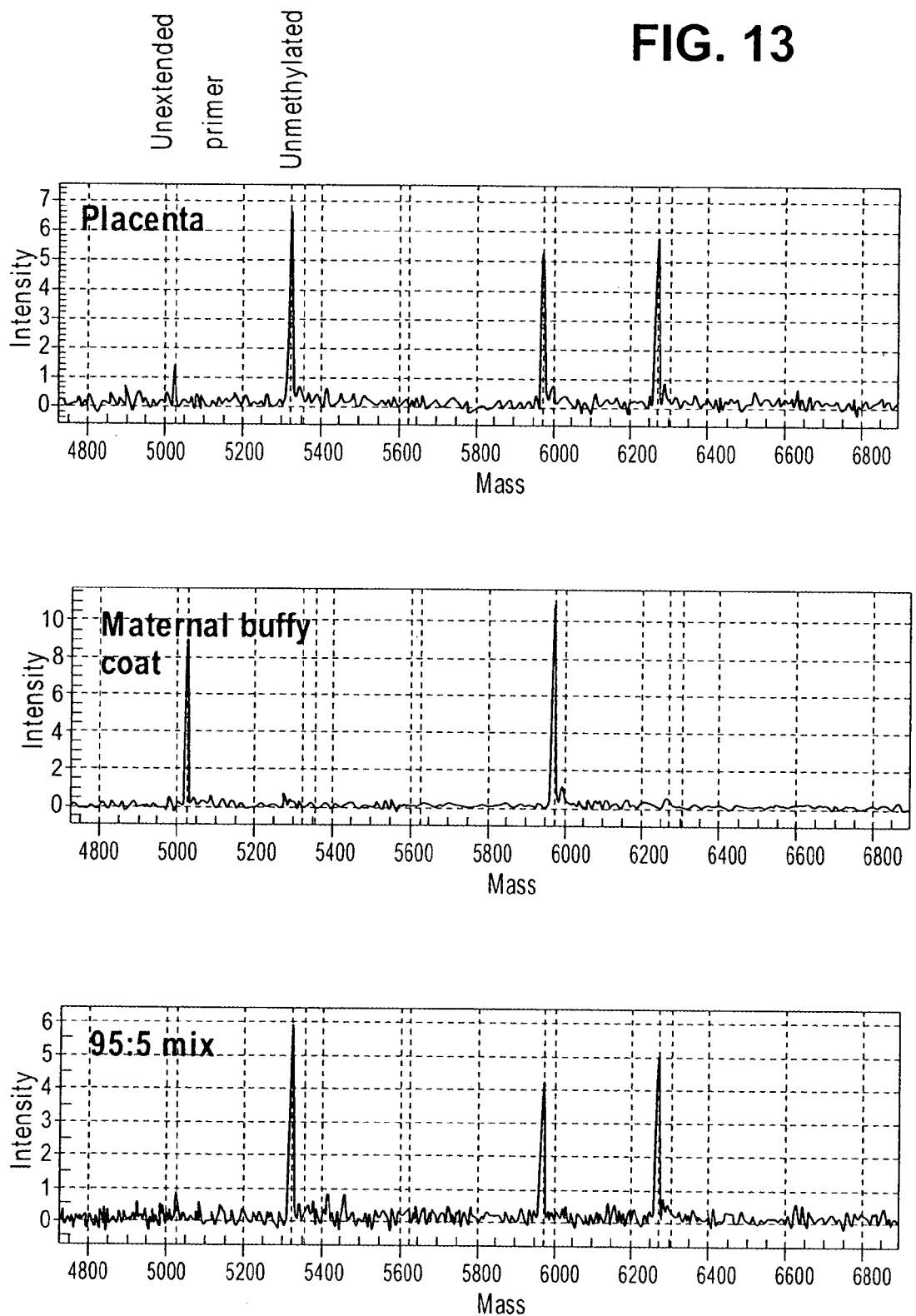
FIG. 13. Mass spectrometric tracings of the homogeneous MassEXTEND assay targeting the unmethylated form of CGI137. Results for the pure placental DNA, maternal buffy coat DNA, 95:5 (maternal buffy coat DNA:placental DNA) mixture, pre-and post-delivery maternal plasma and no template controls (NTC) are shown. For all mass spectra, the x-axis depicts the molecular weight of the detected extension products (shown as sharp peaks), while the y-axis depicts the intensity in arbitrary units. The expected position of the unmethylated molecule is as marked.
Figure 13:
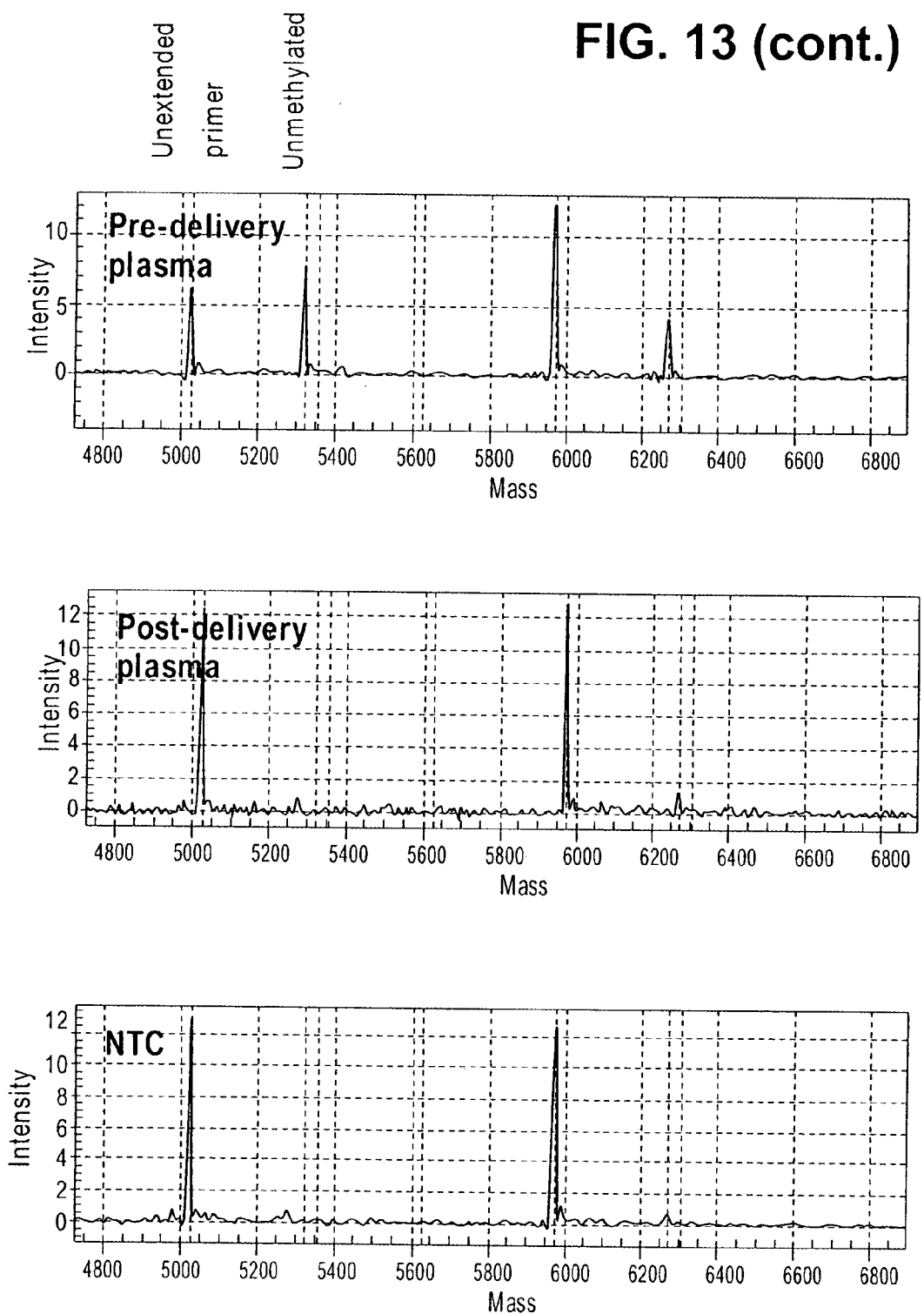

Mass spectra for the MassARRAY analyses are shown in FIG. 13. The primer extension product for the unmethylated form of CGI137 can be detected in the placental and pre-delivery plasma DNA samples as well as the 95:5 mixtures of maternal buffy coat and placental DNA. These data suggest that the assay is sensitive to the detection of the placenta-derived unmethylated form of CGI137 in maternal plasma and DNA mixtures down to a fractional concentration of 5%. No signal was detected post-delivery maternal plasma sample which confirms the pregnancy-specificity of the unmethylated form of CGI137. The lack of signal in the in the maternal buffy coat sample also confirms the specificity of the assay towards the detection of the unmethylated form of CGI137. In summary, due to the differences in the methylation profile of CGI137 between placental tissues and maternal blood cells, sensitive and specific assays could be developed to target the detection of the placenta-derived form of CGI137 among a background of CGI137 methylated molecules derived from maternal blood cells. As the placenta is a tissue source of fetal DNA release into the maternal circulation (Chim et al., supra), in which the latter contains a high background of DNA derived from maternal blood cells (Liu et al., supra), assays targeting placenta-specific epigenetic markers are useful for the detection of fetal-specific nucleic acid molecules in maternal blood.

Example 3

An alternative method, cmbined bisulfite restriction analysis (COBRA) (Xiong and Laird *Nucleic Acids Res* 25: 2532-2534, 1997), was used to assess for the presence of differential methylation of 3 genomic sequences on chromosome 21 (Table 11) between DNA from placentas and maternal blood cells.

TABLE 11

Identity, location, primer sequences and PCR reaction conditions of the
studied genomic sequences on chromosome 21. The respective regions on
genomic contigs (accession number, version, start and end nucleotide
numbers) deposited at GenBank of the National Center for Biotechnology
Information and chromosomal locations (chromosome, start and end
nucleotide numbers) on the Human May 2004 (hg17) assembly of the UCSC
genome browser (genome.ucsc.edu) are shown in the second and third
columns, respectively.

| Sequence name | Region on genomic contig | Chromosomal location | F-primer (5'-3') | SEQ ID NO: | R-primer (5'-3') |
|---|---|---|---|---|---|
| HLCS region A | NT_011512.10: 24015427-24015090 | chr21:37, 275, 090-37, 275, 427 | GGAGTGTTAAATTTG GTTATTTTTGTTTGTTAT | 50 | CRCTACCCTTCTC CACTAACTACTCAAA |
| HLCS region B1 | NT_011512.10: 24015074-24014765 | chr21:37, 274, 765-37, 275, 074 | AGGAGTTAGAYGTT TTAGTTYGTGTGGTT | 52 | CTAAACACCCR AATCCCCAAAA |
| HLCS region B2 | NT_011512.10: 24015063-24014651 | chr21:37, 274, 651-37, 275, 063 | GTTTTAGTTYGTGT GGTTAGAGGTGGT | 54 | CTAAAAAATAAAAAA CAAAATCCAAACAAA |
| CGI009 | NT_011512.10: 12596248-12596458 | chr21:25, 856, 248-25, 856, 458 | AAAAGGYGTTTGG TYGGTTATGAGTTAT | 56 | AAACTAAAAT-CRACRTA CCTACAATACCAAAAA |

| | | PCR conditions | | | | | |
|---|---|---|---|---|---|---|---|
| Sequence name | SEQ ID NO: | MgCl₂ (mM) | Primer (nM) | PCRx Enhancer | HotStar Taq (U) | Annealing temperature (° C.) | Cycle Number |
| HLCS region A | 51 | 3 | 200 | 2x | 0.4 | 58 | 55 |
| HLCS region B1 | 53 | 2.5 | 200 | 2x | 0.4 | 60 | 50 |
| HLCS region B2 | 55 | 3 | 200 | 2x | 0.4 | 58 | 55 |
| CGI009 | 57 | 3 | 200 | 2x | 0.4 | 58 | 50 |

Materials and Methods

Combined bisulfite restriction analysis (COBRA). One µg DNA was subjected to bisulfite conversion by EZ DNA Methylation Kit (Zymo Research, Orange, Calif.) according to manufacturer's instructions. Forty nanograms bisulfite-converted DNA (based on original unconverted DNA input) was then subjected to PCR amplification as was described in Example 1, with some modifications. Reagents supplied in the HotStar Taq DNA Polymerase Kit (Qiagen, Hilden, Germany) were used. Reagent compositions for each PCR are detailed in Table 11. Typically, PCR was performed in a final reaction volume of 20 µl, with MgCl₂, primers, HotStar Taq, 1×PCR Buffer, 50 µM of each dNTP, and 2×PCRx Enhancer (Invitrogen, Carlsbad, Calif.). The thermal profile consisted of an initial denaturation step of 95° C. for 15 min, followed by 50-55 cycles of 95° C. for 20 sec, 58 or 60° C. for 30 sec (Table 11), 72° C. for 1.5 min, and a final extension of 72° C. for 3 min. PCR products were then subjected to restriction enzyme digestion. The restriction enzyme to be used for each respective locus was chosen for its ability to distinguish between the methylated and unmethylated sequence after bisulfite conversion. In essence, restriction sites are only present in either the methylated or unmethylated sequence but not both, so that one of the sequences would be digested while the other would remain intact (Table 12). Restriction enzyme digestions were performed in a final reaction volume of 20 µl, with 5 µl PCR products, 1× appropriate buffer, and 10 U restriction enzyme (or none for mock digestion), under the manufacturer's recommended temperatures for 2 hr. All enzymes were purchased from New England Biolabs (Beverly, Mass.). Digested products were then analyzed by gel electrophoresis.

TABLE 12

Result prediction for COBRA analysis

| Locus name | Enzyme | cutting status | methylation status | products with complete digestion (bp) |
|---|---|---|---|---|
| HLCS region A | BstU I | No cut | un-methylated | 338 |
| | | cut | methylated | 285, 53 |
| HLCS region B1 | BstU I | No cut | un-methylated | 310 |
| | | cut | methylated | 45, 22, 176, 30, 37 |
| HLCS region B2 | BstU I | No cut | un-methylated | 413 |
| | | cut | methylated | 34, 22, 176, 30, 151 |
| CGI009 | BstU I | No cut | un-methylated | 211 |
| | | cut | methylated | 82, 63, 51, 15 |
| CGI132 | BstU I | No cut | un-methylated | 210 |
| | | cut | methylated | 60, 49, 56, 45 |

Cloning and bisulfite sequencing. DNA from the same PCR amplification reaction as described in "Combined bisulfite restriction analysis (COBRA)" session shown above was used for cloning and bisulfite sequencing. To analyze methylation status at the resolution of a single molecule, the PCR product was TA-cloned into a plasmid vector using the pGEM-T Easy Vector System (Promega, Madison, Wis.). The inserts from the positive recombinant clones were analyzed by cycle sequencing using the BigDye Terminator Cycle Sequencing v1.1 kit (Applied Biosystems) as per the manufacturer's instructions. After purification by ethanol precipitation, the samples were resuspended by 10 µl of Hi-Di formamide and run on a 3100 DNA Analyzer (Applied Biosystems).

Results and Conclusion

Figure 14A:
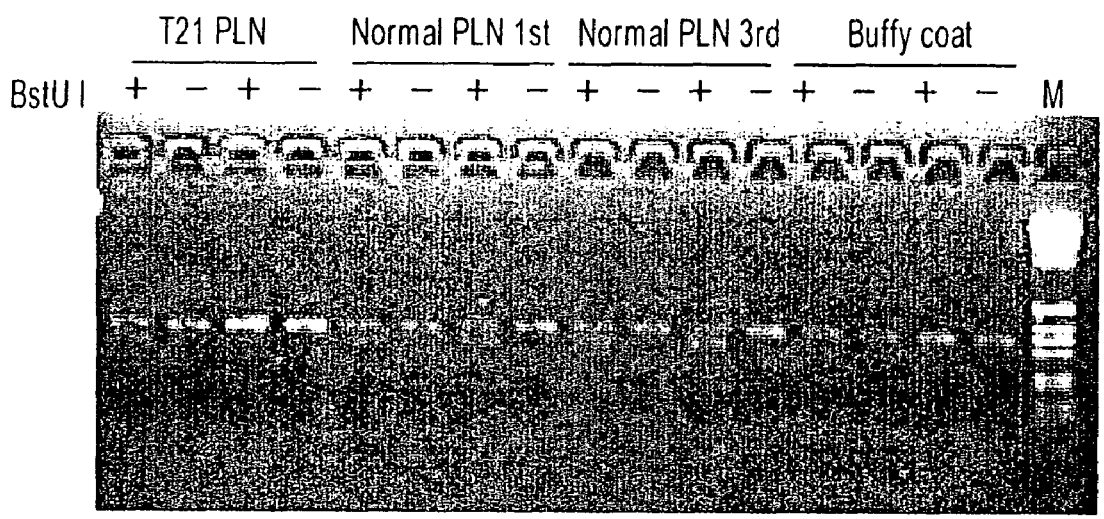
FIG. 14. Combined Bisulfite Restriction Analysis (COBRA) analysis of (A). Holocarboxylase Synthetase region A, (B). region B1 and (C). region B2. Two trisomy 21 placentas (T21 PLN), two $1^{st}$ trimester normal placentas (Normal PLN $1^{st}$), two $3^{rd}$ trimester normal placentas (Normal PLN $3^{rd}$), and two $1^{st}$ trimester maternal blood cells (Buffy coat) were analyzed. PCR products were digested with (+) or without (-) BstU I enzyme. DNA methylation was detected by the appearance of the smaller size digestion products. One kb ladder (Invitrogen Carlsbad, Calif.) (M) was used in gel electrophoresis.
Figure 14B:
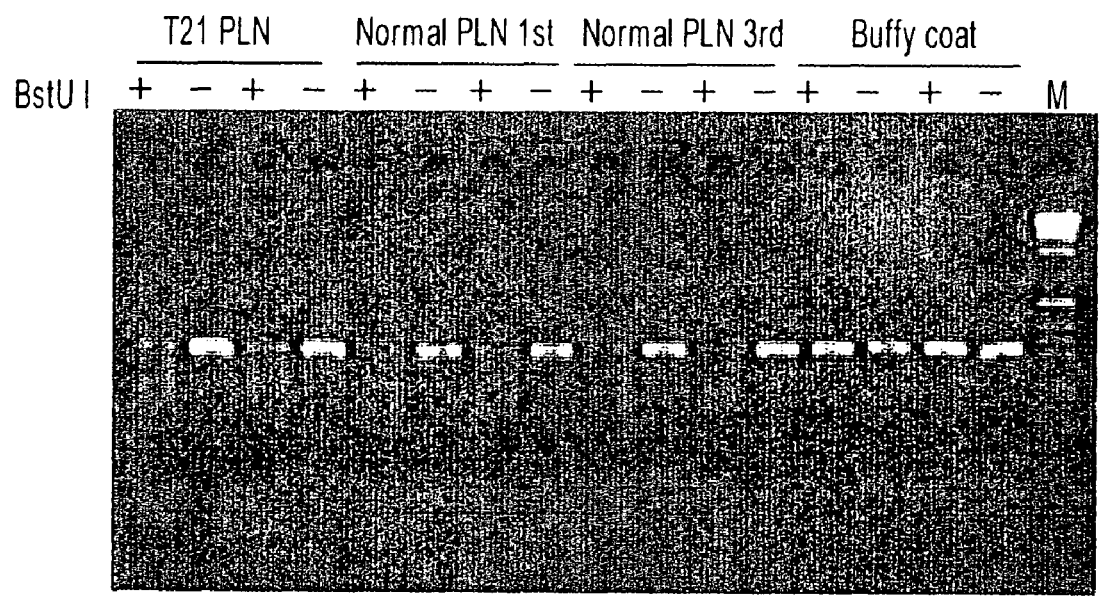
Figure 14C:
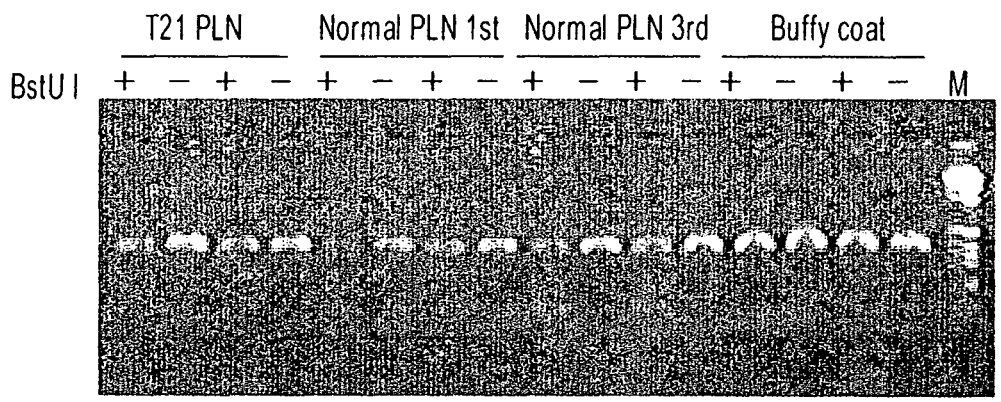
Figure 17:
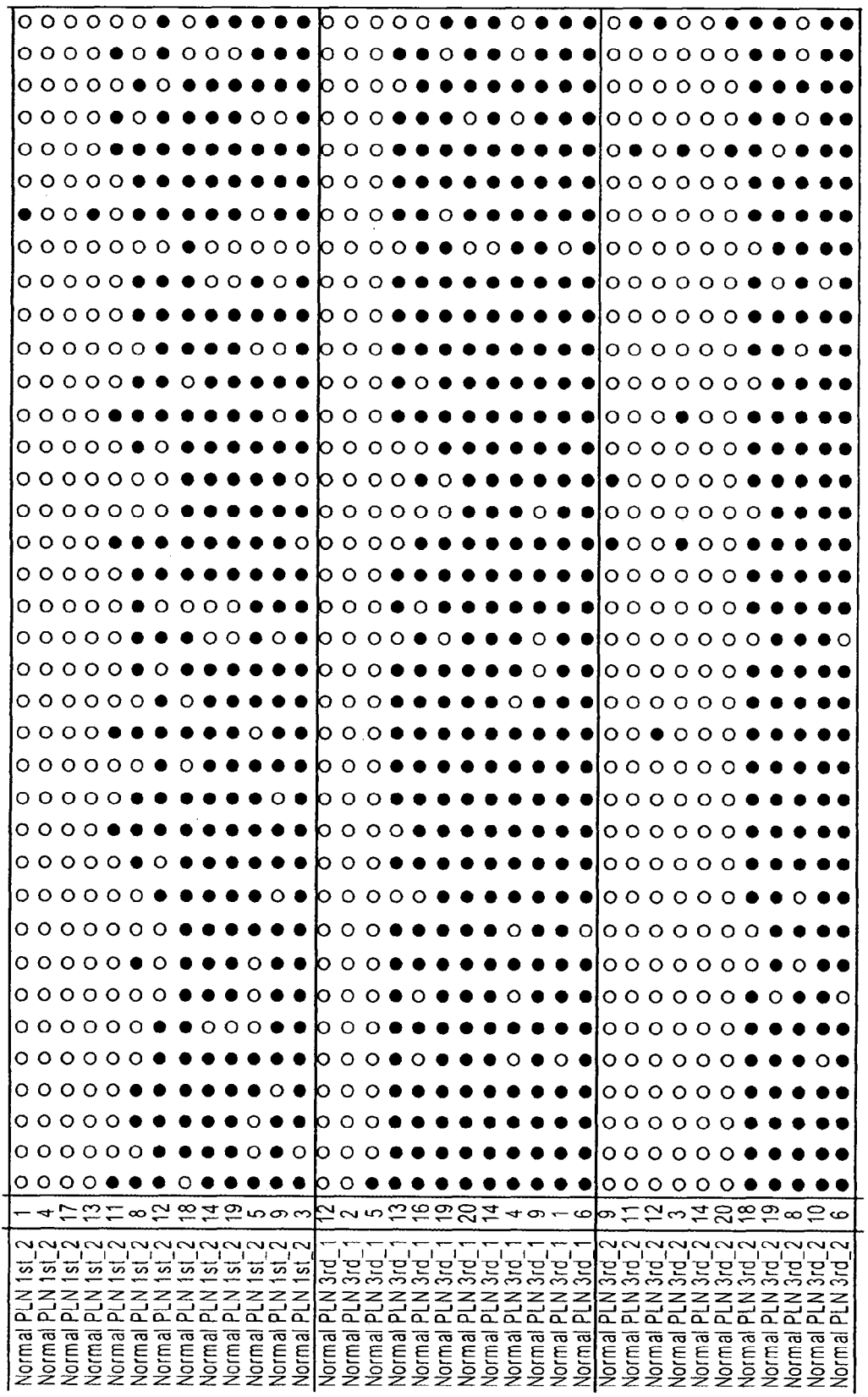
FIG. 17. Cloning and bisulfite sequencing of HLCS region B2 among placental tissues and maternal blood cells. Individual CpG sites are numbered across the first row, with nucleotide positions defined relative to the reverse strand of chr21:37,274,682-37,275,036 of the Human May 2004 (hg17) assembly of the UCSC Genome Browser. Each subsequent row depicts the methylation status across the CpG sites in a single DNA molecule isolated by cloning. Filled and unfilled circles represent methylated and unmethylated CpG sites, respectively. Clones from trisomy 21, normal $1^{st}$ trimester and normal $3^{rd}$ trimester placental tissue samples are labeled with a prefix "T21 PLN," "Normal PLN $1^{st}$" and "Normal PLN $3^{rd}$," respectively, while those from maternal blood cells are labeled with a prefix "Buffy coat." Placenta and maternal blood cells from different pregnant individuals are identified by sample numbers following the prefix.
Figure 17:
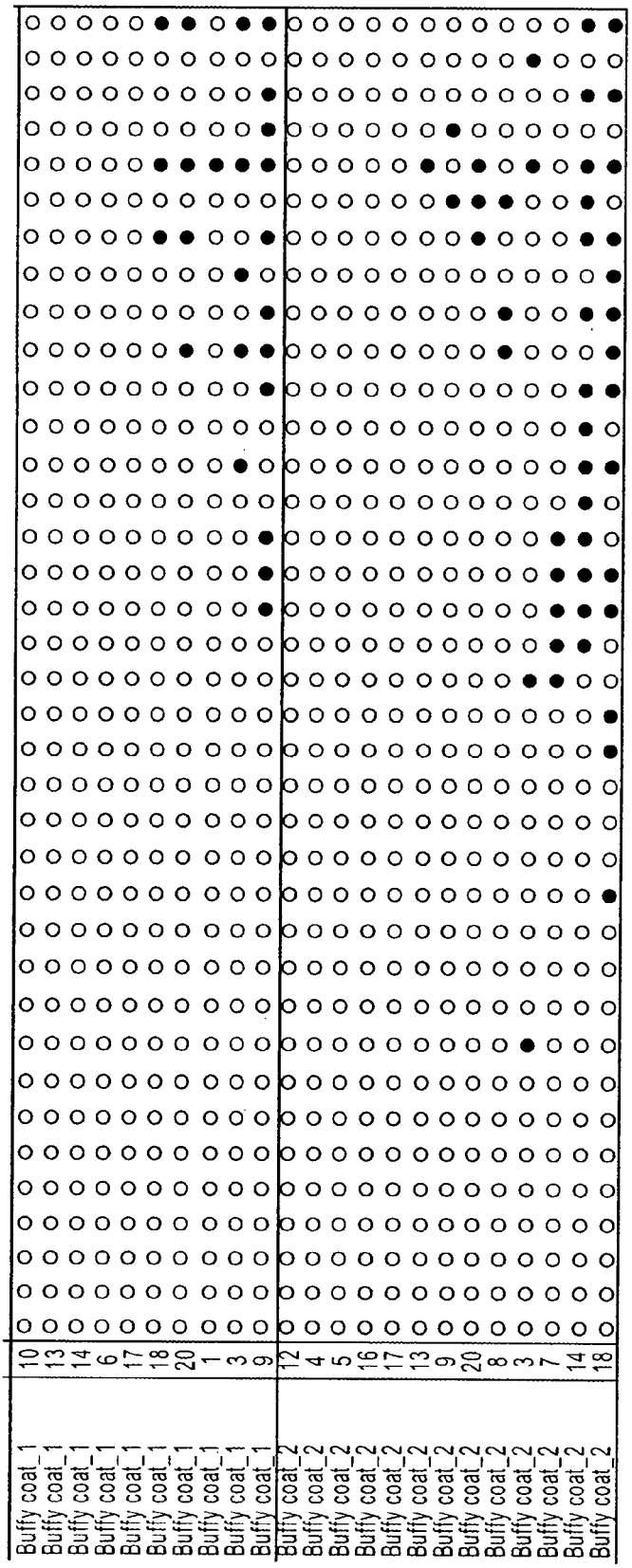

Holocarboxylase Synthetase (HLCS). The methylation profiles of the putative promoter region of HLCS from 2 maternal blood cell samples were compared with those of 2 first-trimester and 2 third-trimester placental tissue samples collected from normal pregnancies, as well as 2 first-trimester placental tissue samples from trisomy 21 pregnancies. COBRA assay was performed and the gel electrophoresis data for region A, region B1, and region B2 are shown in FIGS. 14A, 14B, and 14C, respectively. In general, the placenta is hypermethylated when compared to maternal blood cells. Cloning and bisulfite sequencing experiment was performed on region B2 to further analyze methylation status at the resolution of a single molecule, and the result shown in FIG. 17 confirmed that the methylation in HLCS is placental specific.

Figure 15:
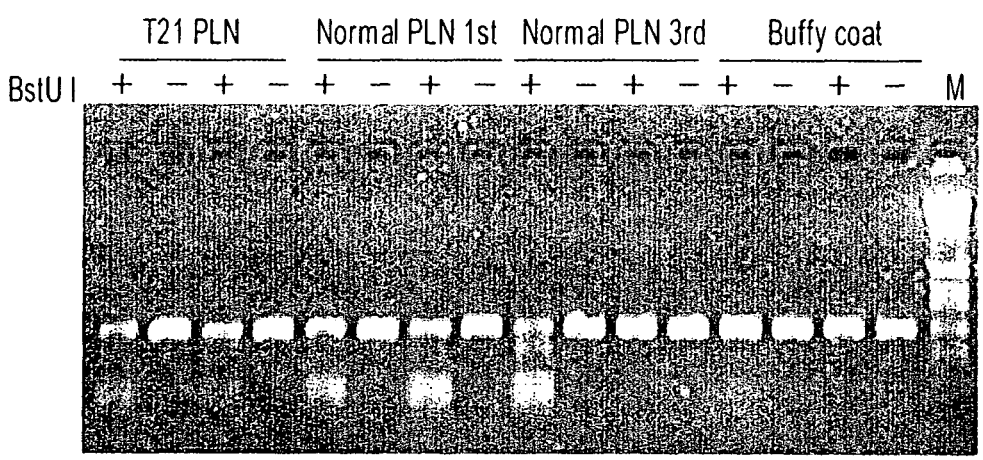
FIG. 15. COBRA analysis of CGI009. Two trisomy 21 placentas (T21 PLN), two $1^{st}$ trimester normal placentas (Normal PLN $1^{st}$), two $3^{rd}$ trimester normal placentas (Normal PLN $3^{rd}$), and two $1^{st}$ trimester maternal blood cells (Buffy coat) were analyzed. PCR products were digested with (+) or without (-) BstU I enzyme. DNA methylation was detected by the appearance of the smaller size digestion products. One kb ladder (Invitrogen Carlsbad, Calif.) (M) was used in gel electrophoresis.

CGI009. The methylation profiles of CGI009 from 2 maternal blood cell samples were compared with those of 2 first-trimester and 2 third-trimester placental tissue samples collected from normal pregnancies, as well as 2 first-trimester placental tissue samples from trisomy 21 pregnancies. COBRA assay was performed and the gel electrophoresis data are shown in FIG. 15. In general, the placenta is hypermethylated when compared to maternal blood cells.

Figure 16:
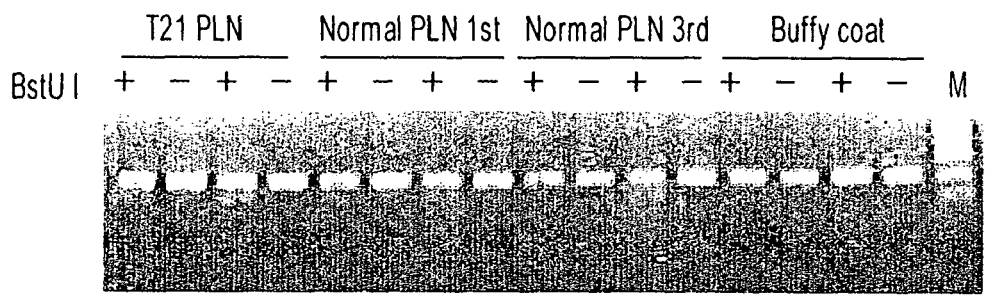
FIG. 16. COBRA analysis of CGI132. Two trisomy 21 placentas (T21 PLN), two $1^{st}$ trimester normal placentas (Normal PLN $1^{st}$), two $3^{rd}$ trimester normal placentas (Normal PLN $3^{rd}$), and two $1^{st}$ trimester maternal blood cells (Buffy coat) were analyzed. PCR products were digested with (+) or without (-) BstU I enzyme. DNA methylation was detected by the appearance of the smaller size digestion products. One kb ladder (Invitrogen Carlsbad, Calif.) (M) was used in gel electrophoresis.

CGI132. The methylation profiles of CGI132 from 2 maternal blood cell samples were compared with those of 2 first-trimester and 2 third-trimester placental tissue samples collected from normal pregnancies, as well as 2 first-trimester placental tissue samples from trisomy 21 pregnancies. COBRA assay was performed and the gel electrophoresis data are shown in FIG. 16. In general, the placenta is hypermethylated when compared to maternal blood cells.

Example 4

Based on the differential methylation feature of the identified markers in placental tissues and maternal blood cells, an alternative method using methylation sensitive restriction enzyme digestion followed by real time quantitative PCR was developed to quantitatively analyze the differential methylation of the genomic sequence of HLCS region B2 (Table 11) between DNA from placentas and maternal blood cells.

Materials and Methods

Methylation sensitive restriction enzyme digestion. DNA was extracted from the placental tissues using the QIAamp DNA Mini Kit (Qiagen, Hilden, Germany). DNA from the maternal buffy coat and plasma was extracted by the QIAamp DNA Blood Mini Kit (Qiagen, Hilden, Germany) according to the manufacturer's instructions. For each placental and buffy coat DNA sample, 100 ng DNA was subjected to methylation sensitive restriction enzyme digestion. Restriction enzyme digestions were performed in a final reaction volume of 50 µl, with DNA, 1× appropriate buffer, and 25 U of Hpa II and 50 U of BstU I (or none for mock digestion), under the manufacturer's recommended temperatures for at least 16 hr. For each maternal plasma sample, 1.6 ml plasma was used for DNA extraction, and was eluted in 50 µl of deionized water, 21 µl of which was subjected to restriction enzyme digestion. Enzyme digestions were performed in a final reaction volume of 30 µl, with DNA, 1× appropriate buffer, and 20 U of Hpa II and 30 U of BstU I (or none for mock digestion), under the manufacturer's recommended temperatures for at least 16 hr. All enzymes were purchased from New England Biolabs (Beverly, Mass.). Digested products were then analyzed by real time quantitative PCR. The selected restriction enzymes only digest the unmethylated DNA but not the methylated DNA. Since the data from Example 3 has shown that HLCS is hypermethylated in placental tissues and hypomethylated in maternal blood cells, we expect a proportion of DNA from placental tissues would remain detectable while most DNA from maternal blood cells would be digested and thus not detectable after restriction enzyme treatment.

Real time quantitative PCR. Real time PCR assay was developed for quantitative analysis of HLCS genomic DNA with and without restriction enzyme digestion. 4 µl of restriction enzyme treated DNA or mock digestion sample was used in the real time PCR assay. Each reaction contains 1× TaqMan Universal PCR Master Mix (Applied Biosystems, Foster City, Calif.), 300 nM of forward primer (5'-CCGTGTGGC-CAGAGGTG-3'; SEQ ID NO:60), 300 nM of reverse primer (5'-TGGGAGCCGGAACCTACC-3'; SEQ ID NO:61), and 100 nM of TaqMan probe (5'-6FAM-TCCCGACCTGGC-CCTTTGCC-TAMRA-3'; SEQ ID NO:62). The thermal profile was 50° C. for 2 min, 95° C. for 10 min, 50 cycles of 95° C. for 15 sec, and 60° C. for 1 min. All reactions were run in duplicate, and the mean quantity was taken. Serially diluted human genomic DNA originally quantified by optical density measurement was used as the quantitative standard for the assay. As the detectable HLCS DNA after restriction enzyme digestion represented the methylated fraction, we expressed the real-time quantitative PCR as a methylation index. The methylation index of a sample is calculated by dividing the HLCS DNA concentration after enzyme digestion with that obtained with mock digestion.

Results and Conclusion

Figure 18:
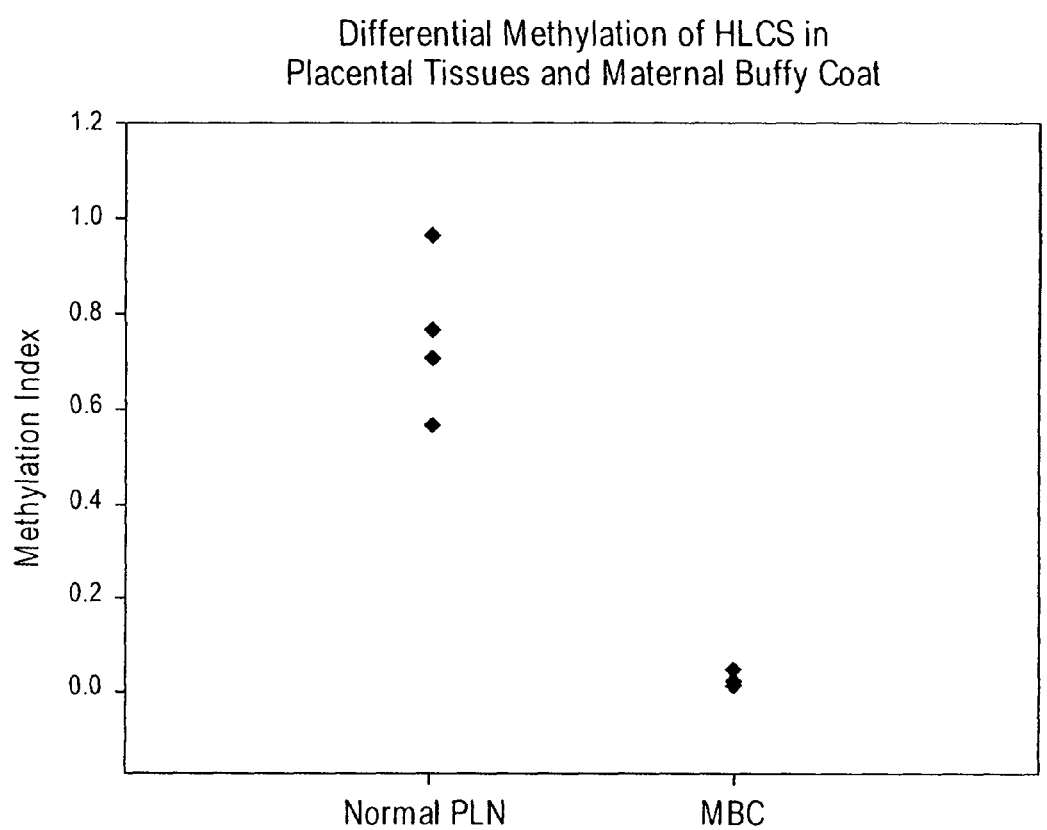
FIG. 18. Quantification of HLCS DNA from placental tissues and maternal buffy coat. Methylation index was defined as the HLCS DNA concentrations after restriction enzyme over total concentrations as determined in the mock digestion control of the same sample. DNA from placental tissues is labeled as "Normal PLN," and that from maternal buffy coat is labeled as "MBC."

The methylation profiles of the putative promoter region of HLCS from 8 maternal blood cell samples were compared with those from 2 first-trimester and 2 third-trimester placental tissue samples collected from normal pregnancies. Restriction enzyme digestion followed by real time PCR analysis was performed and the results are shown in FIG. 18. DNA from all maternal blood cell samples were mostly digested by restriction enzymes, resulting in methylation indices approaching 0; while that from placental tissues were partially digested, resulting in methylation indices ranging from 0.567 to 0.966.

Figure 19A:
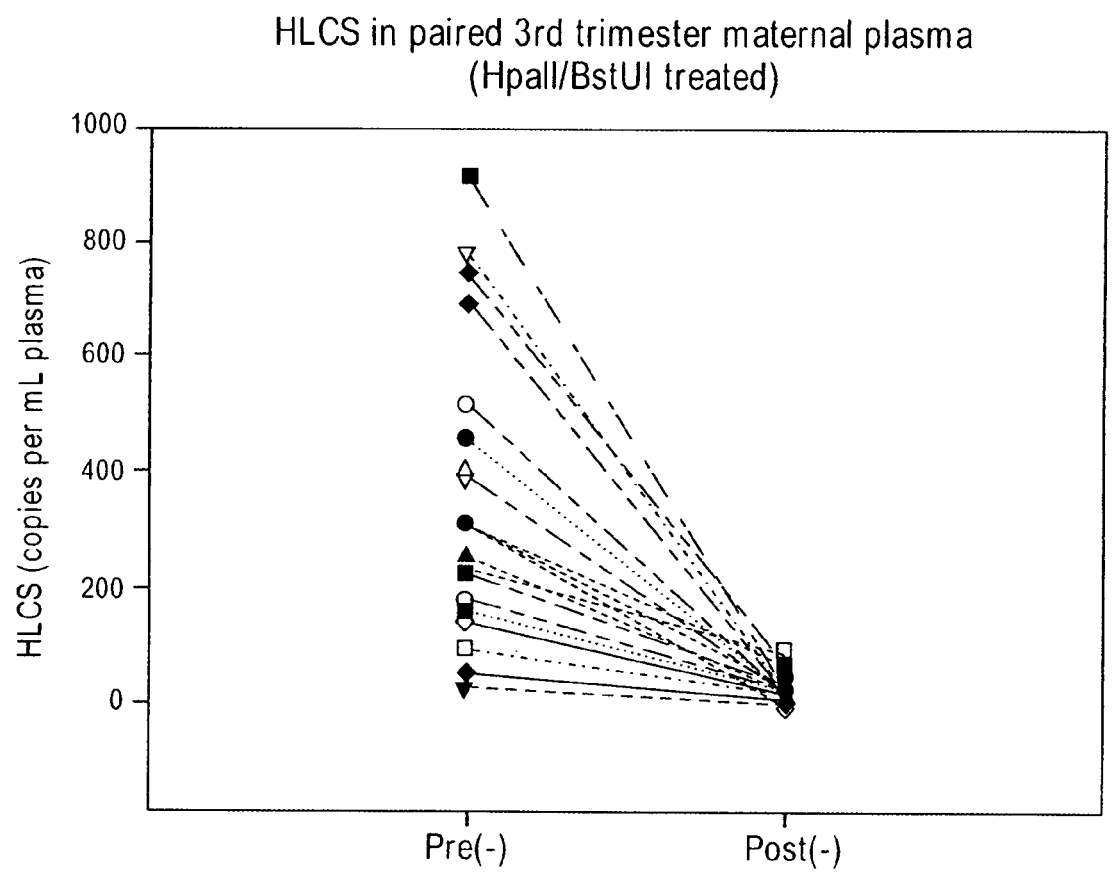
FIG. 19. Fetal-specific HLCS detection in $3^{rd}$ trimester maternal plasma. HLCS signals were detected in maternal plasma samples with (FIG. 19A) or without (FIG. 19B) methylation sensitive restriction enzyme treatment. Pre-delivery plasma samples are labeled as "Pre," while post-delivery plasma samples are labeled as "Post." Restriction enzymes Hpa II and BstU I were used in digestion reactions, and are labeled as "(+)" in the plot. Mock digestions without enzyme treatment are labeled as "(-)".
Figure 19B:
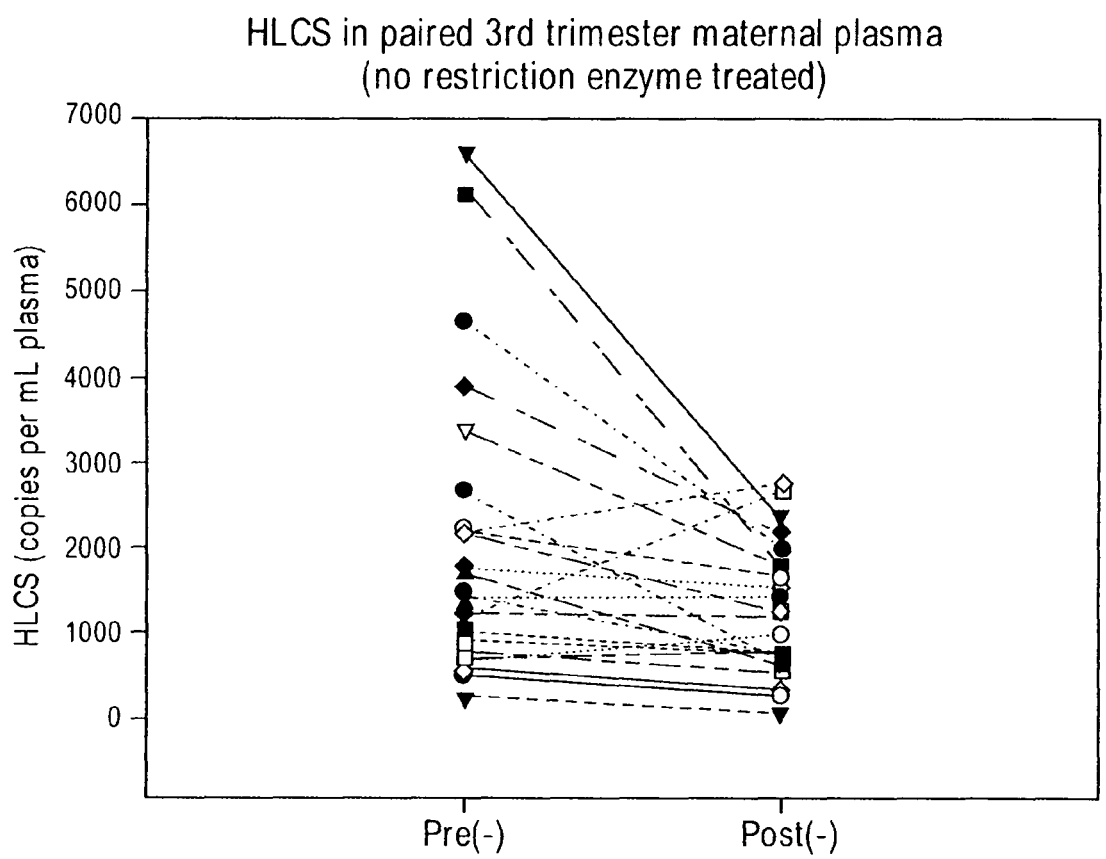

Previous data suggest that placenta is the predominant tissue source of fetal DNA while maternal blood cells are the main contributor of the background maternal DNA that are detectable in maternal plasma. We believe that the placental-specific (with reference to maternal blood cells) fraction of HLCS DNA, namely the methylated or non-digestable fraction can be detected in maternal plasma and is pregnancy-specific. Paired pre-and post-delivery $3^{rd}$ trimester plasma samples from 25 normal pregnant individuals were recruited. Restriction enzyme digestion followed by real time PCR assay was performed and the results are presented in FIG. 19. The HLCS signal is shown to be positively detected in the enzyme digested pre-delivery $3^{rd}$ trimester plasma samples and reduced after delivery. The median of HLCS concentration in post-delivery plasma samples after enzyme digestion was 8.1% of that the median HLCS concentration in pre-delivery plasma samples after enzyme digestion (FIG. 19A). The clearance pattern from enzyme treated pre-and post-delivery plasma indicates that the detected HLCS signal is pregnancy-specific. On the contrary, the median HLCS DNA concentration in post-delivery maternal plasma with mock restriction enzyme digestion was 83.8% of that in the mock-digested pre-delivery samples (FIG. 19B).

All patents, patent applications, and other publications cited in this application, including published amino acid or polynucleotide sequences, are incorporated by reference in the entirety for all purposes.

What is claimed is:

1. A method for detecting trisomy 21 in a fetus carried by a pregnant woman, comprising the steps of:
    (a) obtaining a biological sample from the woman, wherein the sample is whole blood, serum, or plasma;
    (b) determining the methylation status of a CpG-containing genomic sequence in the sample, wherein the genomic sequence from the fetus and the genomic sequence from the woman are differentially methylated, thereby distinguishing the genomic sequence from the woman and the genomic sequence from the fetus in the sample, wherein the genomic sequence is at least 15 nucleotides in length, comprising at least one cytosine, and is within genomic locus Holocarboxylase Synthetase (HLCS) on chromosome 21;
    (c) determining the amount of the methylated genomic sequence from the fetus; and
    (d) comparing the amount of the methylated genomic sequence from the fetus with a standard control, wherein an increase from the standard control indicates the presence of trisomy 21.

2. The method of claim 1, wherein the genomic sequence from the woman is unmethylated and the genomic sequence from the fetus is methylated.

3. The method of claim 1, wherein step (b) is performed by treating the sample with a reagent that differentially modifies methylated and unmethylated DNA.

4. The method of claim 3, wherein the reagent comprises bisulfite.

5. The method of claim 3, wherein the reagent comprises one or more enzymes that preferentially cleave methylated DNA.

6. The method of claim 3, wherein the reagent comprises one or more enzymes that preferentially cleave unmethylated DNA.

7. The method of claim 1, wherein step (b) is performed by methylation-specific PCR.

8. A method for detecting trisomy 21 in a fetus carried by a pregnant woman, comprising the steps of:
    (a) obtaining DNA in a biological sample from the woman, wherein the sample is whole blood, serum, or plasma;
    (b) treating the DNA from step (a) with bisulfite; and
    (c) performing an amplification reaction using the DNA from step (b) and two primers to amplify a CpG-containing genomic sequence, wherein the genomic sequence is at least 15 nucleotides in length, comprises at least one cytosine, and is within genomic locus Holocarboxylase Synthetase (HLCS) on chromosome 21; and wherein at least one of the two primers binds differentially to the genomic sequence from the fetus; and
    (d) comparing the amount of the amplified portion of the genomic sequence from step (c) with a standard control, wherein an increase from the standard control indicates the presence of trisomy 21.

9. The method of claim 8, wherein the amplification reaction is a polymerase chain reaction (PCR).

10. The method of claim 8, wherein the amplification reaction is a methylation-specific PCR.

11. The method of claim 8, wherein the amplification reaction is a nucleic acid sequence based amplification.

12. The method of claim 8, wherein the amplification reaction is a strand displacement reaction.

13. The method of claim 8, wherein the amplification reaction is a branched DNA amplification reaction.

14. A method for detecting trisomy 21 in a fetus carried by a pregnant woman, comprising the steps of:
    (a) obtaining a biological sample from the woman, wherein the sample is whole blood, serum, or plasma;
    (b) determining the amount of a CpG-containing genomic sequence in the sample, wherein the genomic sequence is at least 15 nucleotides in length, comprises at least one methylated cytosine, and is within genomic locus Holocarboxylase Synthetase (HLCS) on chromosome 21; and
    (c) comparing the amount of the genomic sequence with a standard control, wherein an increase from the standard control indicates the presence of trisomy 21.

15. The method of claim 14, wherein step (b) comprises treating DNA present in the blood sample with a reagent that differentially modifies methylated and unmethylated cytosine.

16. The method of claim 15, wherein the reagent comprises bisulfite.

17. The method of claim 15, wherein the reagent comprises one or more enzymes that preferentially cleave DNA comprising methylated cytosine.

18. The method of claim 15, wherein the reagent comprises one or more enzymes that preferentially cleave DNA comprising unmethylated cytosine.

19. The method of claim 14, wherein step (b) comprises an amplification reaction.

20. The method of claim 19, wherein the amplification reaction is a polymerase chain reaction (PCR).

21. The method of claim 20, wherein the PCR is a methylation-specific PCR.

22. The method of claim 19, wherein the amplification reaction is a nucleic acid sequence based amplification.

23. The method of claim 19, wherein the amplification reaction is a strand displacement reaction.

24. The method of claim 19, wherein the amplification reaction is a branched DNA amplification reaction.

25. The method of claim 14, wherein the amount of the genomic DNA sequence is determined by electrophoresis.

26. The method of claim 14, wherein the amount of the genomic DNA sequence is determined by polynucleotide hybridization.

27. The method of claim 1, 8, or 14, wherein the genomic sequence is a CpG island.

* * * * *

SEQUENCE LISTING

<160> NUMBER OF SEQ ID NOS: 62

<210> SEQ ID NO 1
<211> LENGTH: 180
<212> TYPE: DNA
<213> ORGANISM: Homo sapiens
<220> FEATURE:
<221> NAME/KEY: modified_base
<222> LOCATION: (1)...(180)
<223> OTHER INFORMATION: CGI137 amplified region original DNA
      sequence
<223> OTHER INFORMATION: n = methylated cystosine

<400> SEQUENCE: 1
cttcacctgn ggggacccng gngagcccct caggtgccac aggcagggac angcctngct      60
ngatgngtca caccatgtgg ccaccagagc tgnggaaaa tgctggggac cctgcatttc     120
ngtttcaggt ggngaacaag ngccctcac agaactgcag gtagagangg gccnggggca    180

<210> SEQ ID NO 2
<211> LENGTH: 180
<212> TYPE: DNA
<213> ORGANISM: Artificial Sequence
<220> FEATURE:
<223> OTHER INFORMATION: CGI137 amplified region bisulfite-converted
      DNA sequence
<220> FEATURE:
<221> NAME/KEY: modified_base
<222> LOCATION: (1)...(180)
<223> OTHER INFORMATION: n = methylated cytosine

<400> SEQUENCE: 2
ttttatttgn ggggatttng gngagttttt taggtgttat aggtagggat angtttngtt      60
ngatgngtta tattatgtgg ttattagagt tgnggaaaa tgttggggat tttgtatttt     120
ngttttaggt ggngaataag ngtttttat agaattgtag gtagagacgg gttcgggta    180

<210> SEQ ID NO 3
<211> LENGTH: 32
<212> TYPE: DNA
<213> ORGANISM: Artificial Sequence
<220> FEATURE:
<223> OTHER INFORMATION: homogenous MassEXTEND protocol primer
      extension assay methylation specific CGI137 forward primer

<400> SEQUENCE: 3
tgttataggt agggatatgt tttgtttgac gt                                    32

<210> SEQ ID NO 4
<211> LENGTH: 35
<212> TYPE: DNA
<213> ORGANISM: Artificial Sequence
<220> FEATURE:
<223> OTHER INFORMATION: homogenous MassEXTEND protocol primer
      extension assay methylation specific CGI137 reverse primer

<400> SEQUENCE: 4
agagatggat gttaagatat tttttgtgaa taggt                                 35

<210> SEQ ID NO 5
<211> LENGTH: 20
<212> TYPE: DNA
<213> ORGANISM: Artificial Sequence
<220> FEATURE:
<223> OTHER INFORMATION: homogenous MassEXTEND protocol primer
      extension assay methylation specific CGI137 extension primer -continued

```
<400> SEQUENCE: 5
gttttaggtg gtggataagt                                            20

<210> SEQ ID NO 6
<211> LENGTH: 22
<212> TYPE: DNA
<213> ORGANISM: Artificial Sequence
<220> FEATURE:
<223> OTHER INFORMATION: CGI137 region A F-primer

<400> SEQUENCE: 6
ggttgggttg gaggagggta gt                                         22

<210> SEQ ID NO 7
<211> LENGTH: 25
<212> TYPE: DNA
<213> ORGANISM: Artificial Sequence
<220> FEATURE:
<223> OTHER INFORMATION: CGI137 region A R-primer

<400> SEQUENCE: 7
accccraacc crtctctacc tacaa                                      25

<210> SEQ ID NO 8
<211> LENGTH: 29
<212> TYPE: DNA
<213> ORGANISM: Artificial Sequence
<220> FEATURE:
<223> OTHER INFORMATION: CGI137 region B F-primer

<400> SEQUENCE: 8
aaggggagtt gagatattgt agggtttat                                  29

<210> SEQ ID NO 9
<211> LENGTH: 23
<212> TYPE: DNA
<213> ORGANISM: Artificial Sequence
<220> FEATURE:
<223> OTHER INFORMATION: CGI137 region B R-primer

<400> SEQUENCE: 9
aacacctaaa aaactcrccr aaa                                        23

<210> SEQ ID NO 10
<211> LENGTH: 26
<212> TYPE: DNA
<213> ORGANISM: Artificial Sequence
<220> FEATURE:
<223> OTHER INFORMATION: phosphodiesterase 9A (PDE9A) region A F-
      primer

<400> SEQUENCE: 10
gtttttaggg aggggtatt tygagt                                      26

<210> SEQ ID NO 11
<211> LENGTH: 36
<212> TYPE: DNA
<213> ORGANISM: Artificial Sequence
<220> FEATURE:
<223> OTHER INFORMATION: phosphodiesterase 9A (PDE9A) region A R-
      primer

<400> SEQUENCE: 11
aatctatttt ctatatttca ctatttccaa ataaaa                          36

<210> SEQ ID NO 12
```

```
<211> LENGTH: 36
<212> TYPE: DNA
<213> ORGANISM: Artificial Sequence
<220> FEATURE:
<223> OTHER INFORMATION: phosphodiesterase 9A (PDE9A) region B F-
      primer

<400> SEQUENCE: 12
gtatgtatta attaaatgaa aagatgagtt tgtgat                              36

<210> SEQ ID NO 13
<211> LENGTH: 25
<212> TYPE: DNA
<213> ORGANISM: Artificial Sequence
<220> FEATURE:
<223> OTHER INFORMATION: phosphodiesterase 9A (PDE9A) region B R-
      primer

<400> SEQUENCE: 13
craaaaaccc cttataaaaa accra                                         25

<210> SEQ ID NO 14
<211> LENGTH: 27
<212> TYPE: DNA
<213> ORGANISM: Artificial Sequence
<220> FEATURE:
<223> OTHER INFORMATION: phosphodiesterase 9A (PDE9A) region C F-
      primer

<400> SEQUENCE: 14
ggtggttgtg tgtgtttggt ttttagt                                       27

<210> SEQ ID NO 15
<211> LENGTH: 25
<212> TYPE: DNA
<213> ORGANISM: Artificial Sequence
<220> FEATURE:
<223> OTHER INFORMATION: phosphodiesterase 9A (PDE9A) region C R-
      primer

<400> SEQUENCE: 15
acccaaaaat accccaaacc ataaa                                         25

<210> SEQ ID NO 16
<211> LENGTH: 26
<212> TYPE: DNA
<213> ORGANISM: Artificial Sequence
<220> FEATURE:
<223> OTHER INFORMATION: protein phosphatase 1, regulatory
      (inhibitor) subunit 2 pseudogene 2 (PPP1R2P2) region A
      F-primer

<400> SEQUENCE: 16
aggtttttta gtggggaaaa aatggt                                        26

<210> SEQ ID NO 17
<211> LENGTH: 32
<212> TYPE: DNA
<213> ORGANISM: Artificial Sequence
<220> FEATURE:
<223> OTHER INFORMATION: protein phosphatase 1, regulatory
      (inhibitor) subunit 2 pseudogene 2 (PPP1R2P2)  region A
      R-primer

<400> SEQUENCE: 17
craaacttcc ractcttaac tcaaataac ta                                  32

<210> SEQ ID NO 18
```

```
<211> LENGTH: 32
<212> TYPE: DNA
<213> ORGANISM: Artificial Sequence
<220> FEATURE:
<223> OTHER INFORMATION: protein phosphatase 1, regulatory
      (inhibitor) subunit 2 pseudogene 2 (PPP1R2P2)  region B
      F-primer

<400> SEQUENCE: 18
gattttaygt ygagtagtta ttttgagtta ag                               32

<210> SEQ ID NO 19
<211> LENGTH: 23
<212> TYPE: DNA
<213> ORGANISM: Artificial Sequence
<220> FEATURE:
<223> OTHER INFORMATION: protein phosphatase 1, regulatory
      (inhibitor) subunit 2 pseudogene 2 (PPP1R2P2)  region B
      R-primer

<400> SEQUENCE: 19
aactcctcrt ccacactccc rta                                         23

<210> SEQ ID NO 20
<211> LENGTH: 40
<212> TYPE: DNA
<213> ORGANISM: Artificial Sequence
<220> FEATURE:
<223> OTHER INFORMATION: Similarity to Fem1A (C. elegans) region A
      F-primer

<400> SEQUENCE: 20
aggttaatga tttgtatatt taaaagtttt taggatattt                       40

<210> SEQ ID NO 21
<211> LENGTH: 27
<212> TYPE: DNA
<213> ORGANISM: Artificial Sequence
<220> FEATURE:
<223> OTHER INFORMATION: Similarity to Fem1A (C. elegans) region A
      R-primer

<400> SEQUENCE: 21
accaaatact ccaccacrtc caaataa                                     27

<210> SEQ ID NO 22
<211> LENGTH: 27
<212> TYPE: DNA
<213> ORGANISM: Artificial Sequence
<220> FEATURE:
<223> OTHER INFORMATION: Similarity to Fem1A (C. elegans) region B
      F-primer

<400> SEQUENCE: 22
ayggttattt ggaygtggtg gagtatt                                     27

<210> SEQ ID NO 23
<211> LENGTH: 30
<212> TYPE: DNA
<213> ORGANISM: Artificial Sequence
<220> FEATURE:
<223> OTHER INFORMATION: Similarity to Fem1A (C. elegans) region B
      R-primer

<400> SEQUENCE: 23
ccrattaacc acctccaaat taacctaata                                  30

<210> SEQ ID NO 24
```

```
<211> LENGTH: 29
<212> TYPE: DNA
<213> ORGANISM: Artificial Sequence
<220> FEATURE:
<223> OTHER INFORMATION: CGI009 F-primer

<400> SEQUENCE: 24
aaaaaggygt ttggtyggtt atgagttat                                    29

<210> SEQ ID NO 25
<211> LENGTH: 24
<212> TYPE: DNA
<213> ORGANISM: Artificial Sequence
<220> FEATURE:
<223> OTHER INFORMATION: CGI009 R-primer

<400> SEQUENCE: 25
aaactaaaat cracrtacct acaa                                         24

<210> SEQ ID NO 26
<211> LENGTH: 40
<212> TYPE: DNA
<213> ORGANISM: Artificial Sequence
<220> FEATURE:
<223> OTHER INFORMATION: carbonyl reductase 1 (CBR1) F-primer

<400> SEQUENCE: 26
gttaygtggg tagttaatag ttagtagtta gagattagtt                        40

<210> SEQ ID NO 27
<211> LENGTH: 26
<212> TYPE: DNA
<213> ORGANISM: Artificial Sequence
<220> FEATURE:
<223> OTHER INFORMATION: carbonyl reductase 1 (CBR1) R-primer

<400> SEQUENCE: 27
caaaccrata cccttattac ctccaa                                       26

<210> SEQ ID NO 28
<211> LENGTH: 29
<212> TYPE: DNA
<213> ORGANISM: Artificial Sequence
<220> FEATURE:
<223> OTHER INFORMATION: Down Syndrome cell adhesion molecule
      (DSCAM) F-primer

<400> SEQUENCE: 28
ygygygttgy gtttttgtat atttgtttt                                    29

<210> SEQ ID NO 29
<211> LENGTH: 36
<212> TYPE: DNA
<213> ORGANISM: Artificial Sequence
<220> FEATURE:
<223> OTHER INFORMATION: Down Syndrome cell adhesion molecule
      (DSCAM) R-primer

<400> SEQUENCE: 29
caaaaaaaat taacaaaaaa atccatataa ctaaaa                            36

<210> SEQ ID NO 30
<211> LENGTH: 33
<212> TYPE: DNA
<213> ORGANISM: Artificial Sequence
<220> FEATURE:
<223> OTHER INFORMATION: chromosome 21 open reading frame 29
      (C21orf29) F-primer
```

```
<400> SEQUENCE: 30
agtttggtag ttatttgaat agttaaatga gtt                           33

<210> SEQ ID NO 31
<211> LENGTH: 30
<212> TYPE: DNA
<213> ORGANISM: Artificial Sequence
<220> FEATURE:
<223> OTHER INFORMATION: chromosome 21 open reading frame 29
      (C21orf29) R-primer

<400> SEQUENCE: 31
aactttctca tcctactccc taaatctata                               30

<210> SEQ ID NO 32
<211> LENGTH: 26
<212> TYPE: DNA
<213> ORGANISM: Artificial Sequence
<220> FEATURE:
<223> OTHER INFORMATION: CGI111 F-primer

<400> SEQUENCE: 32 ttttttagg tagttgaaag aaaagg                                    26

<210> SEQ ID NO 33
<211> LENGTH: 20
<212> TYPE: DNA
<213> ORGANISM: Artificial Sequence
<220> FEATURE:
<223> OTHER INFORMATION: CGI111 R-primer

<400> SEQUENCE: 33
cctccctcct caaaataaac                                          20

<210> SEQ ID NO 34
<211> LENGTH: 28
<212> TYPE: DNA
<213> ORGANISM: Artificial Sequence
<220> FEATURE:
<223> OTHER INFORMATION: CGI121 F-primer

<400> SEQUENCE: 34
tttttagata ttttttgggt ttaaggtt                                 28

<210> SEQ ID NO 35
<211> LENGTH: 21
<212> TYPE: DNA
<213> ORGANISM: Artificial Sequence
<220> FEATURE:
<223> OTHER INFORMATION: CGI121 R-primer

<400> SEQUENCE: 35
aaatccacct acccaaacac c                                        21

<210> SEQ ID NO 36
<211> LENGTH: 31
<212> TYPE: DNA
<213> ORGANISM: Artificial Sequence
<220> FEATURE:
<223> OTHER INFORMATION: KIAA0656 region A F-primer

<400> SEQUENCE: 36
ttggtggtyg ygaagtgttt tgttagtat t                              31

<210> SEQ ID NO 37
```

```
<211> LENGTH: 30
<212> TYPE: DNA
<213> ORGANISM: Artificial Sequence
<220> FEATURE:
<223> OTHER INFORMATION: KIAA0656 region A R-primer

<400> SEQUENCE: 37
acctctcaaa ccraataaac ctaacaaaac                                        30

<210> SEQ ID NO 38
<211> LENGTH: 30
<212> TYPE: DNA
<213> ORGANISM: Artificial Sequence
<220> FEATURE:
<223> OTHER INFORMATION: KIAA0656 region B F-primer

<400> SEQUENCE: 38
gygygygttt aayggttttg ttaggtttat                                        30

<210> SEQ ID NO 39
<211> LENGTH: 30
<212> TYPE: DNA
<213> ORGANISM: Artificial Sequence
<220> FEATURE:
<223> OTHER INFORMATION: KIAA0656 region B R-primer

<400> SEQUENCE: 39
cataataata acttctcaaa cccccaatca                                        30

<210> SEQ ID NO 40
<211> LENGTH: 37
<212> TYPE: DNA
<213> ORGANISM: Artificial Sequence
<220> FEATURE:
<223> OTHER INFORMATION: heat shock transcription factor 2 binding
      protein (HSF2BP) region A F-primer

<400> SEQUENCE: 40
tayggagtag agaagagagt gattatttat tttaygt                                37

<210> SEQ ID NO 41
<211> LENGTH: 24
<212> TYPE: DNA
<213> ORGANISM: Artificial Sequence
<220> FEATURE:
<223> OTHER INFORMATION: heat shock transcription factor 2 binding
      protein (HSF2BP) region A R-primer

<400> SEQUENCE: 41
cracaacrac cataaacraa acra                                              24

<210> SEQ ID NO 42
<211> LENGTH: 28
<212> TYPE: DNA
<213> ORGANISM: Artificial Sequence
<220> FEATURE:
<223> OTHER INFORMATION: heat shock transcription factor 2 binding
      protein (HSF2BP) region B F-primer

<400> SEQUENCE: 42
gtttaaatay gttggygtyg gttagggt                                          28

<210> SEQ ID NO 43
<211> LENGTH: 35
<212> TYPE: DNA
<213> ORGANISM: Artificial Sequence
<220> FEATURE:
<223> OTHER INFORMATION: heat shock transcription factor 2 binding
``` protein (HSF2BP) region B R-primer

<400> SEQUENCE: 43
ttacatcaaa aactaacttt ccttctactt tacaa                35

<210> SEQ ID NO 44
<211> LENGTH: 26
<212> TYPE: DNA
<213> ORGANISM: Artificial Sequence
<220> FEATURE:
<223> OTHER INFORMATION: COL6A1 region A F-primer

<400> SEQUENCE: 44
gttyggtygg gaggttttgt gatatt                        26

<210> SEQ ID NO 45
<211> LENGTH: 33
<212> TYPE: DNA
<213> ORGANISM: Artificial Sequence
<220> FEATURE:
<223> OTHER INFORMATION: COL6A1 region A R-primer

<400> SEQUENCE: 45
aactacraaa craaataaac aaccrttaac ata                 33

<210> SEQ ID NO 46
<211> LENGTH: 30
<212> TYPE: DNA
<213> ORGANISM: Artificial Sequence
<220> FEATURE:
<223> OTHER INFORMATION: COL6A1 region B F-primer

<400> SEQUENCE: 46
tyggtttatt gyggttgtat tattagggtt                    30

<210> SEQ ID NO 47
<211> LENGTH: 26
<212> TYPE: DNA
<213> ORGANISM: Artificial Sequence
<220> FEATURE:
<223> OTHER INFORMATION: COL6A1 region B R-primer

<400> SEQUENCE: 47
tccataacat cgacgacact aaccaa                        26

<210> SEQ ID NO 48
<211> LENGTH: 35
<212> TYPE: DNA
<213> ORGANISM: Artificial Sequence
<220> FEATURE:
<223> OTHER INFORMATION: homogenous MassEXTEND protocol primer
      extension assay methylation specific CGI137 reverse primer

<400> SEQUENCE: 48
tctctaccta caattctata aaaaacactt atcca               35

<210> SEQ ID NO 49
<211> LENGTH: 17
<212> TYPE: DNA
<213> ORGANISM: Artificial Sequence
<220> FEATURE:
<223> OTHER INFORMATION: homogenous MassEXTEND protocol primer
      extension assay methylation specific CGI137 extension primer

<400> SEQUENCE: 49
atccccaaca ttttccc                                  17

```
<210> SEQ ID NO 50
<211> LENGTH: 33
<212> TYPE: DNA
<213> ORGANISM: Artificial Sequence
<220> FEATURE:
<223> OTHER INFORMATION: holocarboxylase synthetase (HLCS) region A
      F-primer

<400> SEQUENCE: 50
ggagtgttaa atttggttat ttttgtttgt tat                                    33

<210> SEQ ID NO 51
<211> LENGTH: 28
<212> TYPE: DNA
<213> ORGANISM: Artificial Sequence
<220> FEATURE:
<223> OTHER INFORMATION: holocarboxylase synthetase (HLCS) region A
      R-primer

<400> SEQUENCE: 51
crctaccctt ctccactaac tactcaaa                                          28

<210> SEQ ID NO 52
<211> LENGTH: 29
<212> TYPE: DNA
<213> ORGANISM: Artificial Sequence
<220> FEATURE:
<223> OTHER INFORMATION: holocarboxylase synthetase (HLCS) region B1
      F-primer

<400> SEQUENCE: 52
aggagttaga ygttttagtt ygtgtggtt                                         29

<210> SEQ ID NO 53
<211> LENGTH: 22
<212> TYPE: DNA
<213> ORGANISM: Artificial Sequence
<220> FEATURE:
<223> OTHER INFORMATION: holocarboxylase synthetase (HLCS) region B1
      R-primer

<400> SEQUENCE: 53
ctaaacaccc raatcccaa aa                                                 22

<210> SEQ ID NO 54
<211> LENGTH: 27
<212> TYPE: DNA
<213> ORGANISM: Artificial Sequence
<220> FEATURE:
<223> OTHER INFORMATION: holocarboxylase synthetase (HLCS) region B2
      F-primer

<400> SEQUENCE: 54
gttttagtty gtgtggttag aggtggt                                           27

<210> SEQ ID NO 55
<211> LENGTH: 31
<212> TYPE: DNA
<213> ORGANISM: Artificial Sequence
<220> FEATURE:
<223> OTHER INFORMATION: holocarboxylase synthetase (HLCS) region B2
      R-primer

<400> SEQUENCE: 55
ctaaaaaata aaaacaaaa tccaaaacaa a                                       31

<210> SEQ ID NO 56
```

-continued

```
<211> LENGTH: 28
<212> TYPE: DNA
<213> ORGANISM: Artificial Sequence
<220> FEATURE:
<223> OTHER INFORMATION: CGI009 F-primer

<400> SEQUENCE: 56
aaaaggygtt tggtyggtta tgagttat                                          28

<210> SEQ ID NO 57
<211> LENGTH: 33
<212> TYPE: DNA
<213> ORGANISM: Artificial Sequence
<220> FEATURE:
<223> OTHER INFORMATION: CGI009 R-primer

<400> SEQUENCE: 57
aaactaaaat cracrtacct acaataccaa aaa                                    33

<210> SEQ ID NO 58
<211> LENGTH: 24
<212> TYPE: DNA
<213> ORGANISM: Artificial Sequence
<220> FEATURE:
<223> OTHER INFORMATION: CGI132 F-primer

<400> SEQUENCE: 58
ttgygggtta yggggattta gttt                                              24

<210> SEQ ID NO 59
<211> LENGTH: 24
<212> TYPE: DNA
<213> ORGANISM: Artificial Sequence
<220> FEATURE:
<223> OTHER INFORMATION: CGI132 R-primer

<400> SEQUENCE: 59
craaaacraa craaccaaac ctaa                                              24

<210> SEQ ID NO 60
<211> LENGTH: 17
<212> TYPE: DNA
<213> ORGANISM: Artificial Sequence
<220> FEATURE:
<223> OTHER INFORMATION: holocarboxylase synthetase (HLCS) real
      time quantitative PCR forward primer

<400> SEQUENCE: 60
ccgtgtggcc agaggtg                                                      17

<210> SEQ ID NO 61
<211> LENGTH: 18
<212> TYPE: DNA
<213> ORGANISM: Artificial Sequence
<220> FEATURE:
<223> OTHER INFORMATION: holocarboxylase synthetase (HLCS) real
      time quantitative PCR reverse primer

<400> SEQUENCE: 61
tgggagccgg aacctacc                                                     18

<210> SEQ ID NO 62
<211> LENGTH: 20
<212> TYPE: DNA
<213> ORGANISM: Artificial Sequence
<220> FEATURE:
<223> OTHER INFORMATION: real time quantitative PCR TaqMan probe
<220> FEATURE:
```

```
<221> NAME/KEY: modified_base
<222> LOCATION: (1)...(1)
<223> OTHER INFORMATION: n = t modified by 6FAM
<220> FEATURE:
<221> NAME/KEY: modified_base
<222> LOCATION: (20)...(20)
<223> OTHER INFORMATION: n = c modified by TAMRA

<400> SEQUENCE: 62
ncccgacctg gccctttgcn                                              20
```